(12) United States Patent
Chuang et al.

(10) Patent No.: US 11,998,613 B2
(45) Date of Patent: Jun. 4, 2024

(54) ANTIBODY-DRUG CONJUGATES CONTAINING AN ANTI-MESOTHELIN ANTIBODY AND USES THEREOF

(71) Applicant: DEVELOPMENT CENTER FOR BIOTECHNOLOGY, Taipei (TW)

(72) Inventors: Shih-Hsien Chuang, Taipei (TW); Wei-Ting Sun, Taipei (TW); Ying-Shuan Lailee, Taipei (TW); Chun-Liang Lai, Taipei (TW); Wun-Huei Lin, Taipei (TW); Win-Yin Wei, Taipei (TW); Shih-Chong Tsai, Taipei (TW); Cheng-Chou Yu, Taipei (TW); Chao-Yang Huang, Taipei (TW)

(73) Assignee: DEVELOPMENT CENTER FOR BIOTECHNOLOGY, Taipei (TW)

( * ) Notice: Subject to any disclaimer, the term of this patent is extended or adjusted under 35 U.S.C. 154(b) by 104 days.

(21) Appl. No.: 17/339,747

(22) Filed: Jun. 4, 2021

(65) Prior Publication Data
US 2021/0386866 A1     Dec. 16, 2021

Related U.S. Application Data

(60) Provisional application No. 63/035,175, filed on Jun. 5, 2020.

(51) Int. Cl.
*A61K 47/68*   (2017.01)
*A61K 47/54*   (2017.01)
*A61P 35/00*   (2006.01)

(52) U.S. Cl.
CPC ........ *A61K 47/6851* (2017.08); *A61K 47/545* (2017.08); *A61K 47/6803* (2017.08);
(Continued)

(58) Field of Classification Search
CPC .............. A61K 47/6851; A61K 47/545; A61K 47/6803; A61K 47/6817; A61K 47/6889; A61K 35/00
See application file for complete search history.

(56) References Cited

U.S. PATENT DOCUMENTS

| | | |
|---|---|---|
| 6,809,184 B1 | 10/2004 | Pastan et al. |
| 7,368,110 B2 | 5/2008 | Pastan et al. |

(Continued)

FOREIGN PATENT DOCUMENTS

| | | |
|---|---|---|
| CN | 110507824 A | 11/2019 |
| TW | 201835331 A | 10/2018 |

(Continued)

OTHER PUBLICATIONS

Agarwal P, Bertozzi CR. Bioconjug Chem. Feb. 18, 2015;26(2):176-92. doi: 10.1021/bc5004982. Epub Jan. 30, 2015. PMID: 25494884; PMCID: PMC4335810. (Year: 2015).*

(Continued)

*Primary Examiner* — Adam Weidner
*Assistant Examiner* — Laura Ann Essex
(74) *Attorney, Agent, or Firm* — LADAS & PARRY LLP

(57) ABSTRACT

The present disclosure provides an immunoconjugate includes an antibody comprising an antigen-binding fragment that specifically binds to an epitope in mesothelin, N-glycan binding domain and an N-glycan; a linker linking to the N-glycan; and a payload A and a payload B conjugated to the linker, respectively; wherein the payload A and the payload B are the same or different. A pharmaceutical composition comprises the immunoconjugate and a method for treating cancer are also provided in the disclosure.

15 Claims, 16 Drawing Sheets

Specification includes a Sequence Listing.

(52) U.S. Cl.
CPC ...... *A61K 47/6817* (2017.08); *A61K 47/6889* (2017.08); *A61P 35/00* (2018.01)

(56) References Cited

U.S. PATENT DOCUMENTS

| | | |
|---|---|---|
| 2015/0031624 A1 | 1/2015 | Feldman et al. |
| 2019/0194686 A1 | 6/2019 | Lu et al. |
| 2020/0087697 A1 | 3/2020 | Tsai et al. |

FOREIGN PATENT DOCUMENTS

| | | | |
|---|---|---|---|
| WO | WO-2010136492 A2 * | 12/2010 | ........... A61K 39/395 |
| WO | WO-2014182532 A1 * | 11/2014 | ....... A61K 47/48423 |
| WO | 2016/201240 A1 | 12/2016 | |
| WO | 2018/126092 A1 | 7/2018 | |
| WO | WO-2020102739 A1 * | 5/2020 | ......... C07K 16/2875 |
| WO | WO-2020108530 A1 * | 6/2020 | ......... A61K 39/3955 |

OTHER PUBLICATIONS

Yamazoe S, Hogan JM, West SM, Deng XA, Kotapati S, Shao X, Holder P, Lamba V, Huber M, Qiang C, Gangwar S, Rao C, Dollinger G, Rajpal A, Strop P. Bioconjug Chem. Apr. 15, 2020;31(4):1199-1208. doi: 10.1021/acs.bioconjchem.0c00146. Epub Mar. 27, 2020. PMID: 32178516. (Year: 2020).*

Maderna A, Doroski M, Subramanyam C, Porte A, Leverett CA, Vetelino BC, Chen Z, Risley H, Parris K, Pandit J, Varghese AH, Shanker S, Song C, Sukuru SC, Farley KA, Wagenaar MM, Shapiro MJ, Musto S, Lam MH, Loganzo F, O'Donnell CJ. J Med Chem. Dec. 26, 2014;57(24):10527-43. doi: 10.1021/jm501649k. (Year: 2014).*

English translation of WO2020108530, accessed on Feb. 8, 2023 (Year: 2020).*

Fukunaga A, Maeta S, Reema B, Nakakido M, Tsumoto K. Biochem Biophys Rep. Jul. 14, 2018;15:81-85. doi: 10.1016/j.bbrep.2018.07.005. PMID: 30073208. (Year: 2018).*

Office Action with Search Report dated Jun. 6, 2022.
English translation to Search Report dated Jun. 6, 2022.
CN110507824 A English Translation.
International Search Report and Written Opinion issued in the corresponding PCT Application No. PCT/US2021/035972 dated Dec. 20, 2021.

* cited by examiner

Primary Alignment of VL Segments

```
Kabat      1     5    10    15    20        CDR-1        35    40
SS1        DIELTQSPAIMSASPGEKVTMTC[             ]WYQQKS
VKI        DIQMTQSPSSLSASVGDRVTITC[             ]WYQQKP Kabat           45      CDR-2       60    65    70    75    80    85
SS1        GTSPKRWIY[          ]GVPGRFSGSGSGNSYSLTISSVEAEDDATY
VKI        GKAPKLLIY[          ]GVPSRFSGSGSGTDFTLTISSLQPEDFATY Kabat            CDR-3           100  104
SS1        YC[            ]FGAGTKLEIKR  SEQ ID NO: 8
VKI        YC[            ]FGQGTKVEIKR  SEQ ID NO: 13
```

SS1 : Musmus IGKV4-59*01
Human template(4d5): V kappa I

Primary Alignment of VH Segments

```
Kabat      1     5    10    15    20    25    CDR-1       35    40
SS1        QVQLQQSGPELEKPGASVKISCKAS[         ]WVKQSHGKS
VHIII      EVQLVESGGGLVQPGGSLRLSCAAS[         ]WVRQAPGKG Kabat           45      CDR-2       65    70    75    80 82A B C
SS1        LEWIG[               ]KATLTVDKSSSTAYMDLLSLTS
VHIII      LEWVA[               ]RFTISRDDSKNTLYLQMNSLRA
          EG Kabat      85   90 93 94    CDR-3         105   110
SS1        EDSAVYFCAR[            ]WGQGTTVTVSS  SEQ ID NO: 7
VHIII      EDTAVYYCAR[            ]WGQGTLVTVSS  SEQ ID NO: 14
```

SS1 : Musmus IGHV1-31*01 F
Human template(4d5): VH III

Figure 1A

Primary Alignment of VL Segments

```
Kabat       1    5    10   15   20        CDR-1         35   40
SS1         DIELTQSPAIMSASPGEKVTMTC [               ] WYQQKS
3-11        EIVLTQSPATLSLSPGERATLSC [               ] WYQQKP
HU Kabat            45        CDR-2        60   65   70   75   80   85
SS1         GTSPKRWIY [          ] GVPGRFSGSGSGNSYSLTISSVEAEDDATY
3-11        GQAPRLLIY [          ] GIPARFSGSGSGTDFTLTISSLEPEDFAVY Kabat            CDR-3         100  104
SS1         YC [           ] FGAGTKLEIKR  SEQ ID NO: 8
3-11        YC [           ] FGQGTKVEIKR  SEQ ID NO: 15
```

SS1 : Musmus IGKV4-59*01
Human template(4d5): IGVK3-11*01F

Primary Alignment of V$_H$ Segments

```
Kabat       1    5    10   15   20   25    CDR-1       35   40
SS1         QVQLQQSGPELEKPGASVKISCKAS [           ] WVKQSHGKS
1-2         QVQLVQSGAEVKKPGASVKVSCKAS [           ] WVRQAPGQG Kabat            45        CDR-2        60   70   75      80 82A B C
SS1         LEWIG [                   ] KATLTVDKSSSTAYMDLLSLTS
1-2         LEWMG [                   ] RVTMTRDTSISTAYMELSRLRS Kabat        85   90  93A      CDR-3         105  110
SS1         EDSAVYFCAR [           ] WGQGTTVTVSS  SEQ ID NO: 7
1-2         DDTAVYYCAR [           ] WGQGTLVTVSS  SEQ ID NO: 16
```

SS1 : Musmus IGHV1-31*01 F
Human template: IGHV1-2*02F

Figure 1B

ANTIBODY-DRUG CONJUGATES CONTAINING AN ANTI-MESOTHELIN ANTIBODY AND USES THEREOF

FIELD OF THE INVENTION

The present disclosure relates to an anti-mesothelin antibody-drug conjugate, wherein the glycoprotein comprised therein comprises one or more tri-mannosyl cores. The present disclosure also relates to a method of treating a disease, such as cancer, in a subject in need thereof comprising administering the anti-mesothelin antibody-drug conjugate to the subject.

BACKGROUND OF THE INVENTION

An antibody-drug conjugate (ADC) typically comprises an anticancer drug (e.g. a cytotoxin) coupled to an antibody that specifically targets a marker, e.g., a tumor marker. Antibodies track these markers down in the body and attach themselves to the surface of cancer cells. The binding between the antibody and the target marker (antigen) triggers a signal in the tumor cell, which then internalizes the ADC. After the ADC is internalized, the cytotoxic drug may be released and kills the cancer cell. Due to the specific targeting, side effects of the drug may be lowered.

Mesothelin (MSLN) is a tumor differentiation antigen that is over expressed in several human tumors, including mesothelioma, pancreatic cancer, ovarian cancer, pancreatic adenocarcinoma, lung adenocarcinoma, cholangiocarcinoma, extrahepatic biliary cancer, lung cancer, and epithelioid mesothelioma. Therefore, mesothelin is a promising diagnostic/therapeutic target.

Although many antibodies against mesothelin are developing, such as SS1P (an anti-mesothelin immunotoxin composed of a targeting antibody fragment genetically fused to a truncated fragment of *Pseudomonas* exotoxin A), Anetumab (a monoclonal antibody), and Anetumab Ravtansin (an antibody-drug conjugate), there remains a need for improved therapeutic agents using anti-mesothelin antibodies.

SUMMARY OF THE INVENTION

The present disclosure relates to antibody-drug conjugates containing an anti-mesothelin antibody and their uses in therapy.

One aspect of the disclosure relates to immunoconjugates. An immunoconjugate in accordance with one embodiment of the disclosure includes:

an antibody comprising an antigen-binding fragment that specifically binds to an epitope in mesothelin, an N-glycan binding domain and an N-glycan having a structure of formula (1);

formula (1)

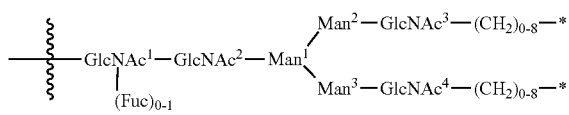

wherein "*" represents a bond or a protecting group; a linker linking to each of the "*" in the N-glycan when "*" presents the bond; and a payload A and a payload B independently conjugated to the linkers; wherein the payload A and the payload B are the same or different.

In some embodiments of the disclosure, the antibody is a monoclonal antibody, a humanized antibody, a human antibody, an antibody Fab fragment, $F(ab')_2$, Fv fragment or Fc fragment from a cleaved antibody, a scFv-Fc fragment, a minibody, a diabody, or a scFv.

In some embodiments of the disclosure, the antigen-binding fragment comprises complementarity determining regions (CDRs) of a heavy chain variable region and complementarity determining regions of a light chain variable region, wherein the complementarity determining regions of the heavy chain variable region comprise CDRH1, CDRH2 and CDRH3 regions, and the complementarity determining regions of the light chain variable region comprise CDRL1, CDRL2 and CDRL3 regions; wherein the CDRH1 region comprises the amino acid sequence of SEQ ID NO: 1; the CDRH2 region comprises the amino acid sequence of SEQ ID NO: 2; the CDRH3 region comprises the amino acid sequence of SEQ ID NO: 3; the CDRL1 region comprises the amino acid sequence of SEQ ID NO: 4; the CDRL2 region comprises the amino acid sequence of SEQ ID NO: 5; and the CDRL3 region comprises the amino acid sequence of SEQ ID NO: 6. In one embodiment of the disclosure, the antibody comprises a heavy chain variable region comprising the amino acid sequence of SEQ ID NO: 7, and a light chain variable region comprising the amino acid sequence of SEQ ID NO: 8. In one embodiment of the disclosure, the antibody comprises a heavy chain variable region comprising the amino acid sequence of SEQ ID NO: 9, and a light chain variable region comprising the amino acid sequence of SEQ ID NO: 10. In one embodiment of the disclosure, the antibody comprises a heavy chain variable region comprising the amino acid sequence of SEQ ID NO: 11, and a light chain variable region comprising the amino acid sequence of SEQ ID NO: 12.

In some embodiments of the disclosure, the antibody comprises a heavy chain constant region, and the N-glycan binding domain is located in the heavy chain constant region.

In some embodiments of the disclosure, the antibody comprises two N-glycans.

Certain embodiments of the effective amount of the immuneconjugate of the present disclosure are those ranging from about about 0.01 mg/kg to 800 mg/kg, 0.05 mg/kg to 600 mg/kg, 0.1 mg/kg to 500 mg/kg, 0.5 mg/kg to 400 mg/kg, 1 mg/kg to 300 mg/kg, 5 mg/kg to 200 mg/kg, 10 mg/kg to 100 mg/kg, 15 mg/kg to 80 mg/kg, 20 mg/kg to 60 mg/kg, 25 mg/kg to 50 mg/kg.

In some embodiments of the disclosure, the linker is selected from the group consisting of a linear or branched alkyl, cycloalkyl, alkenyl, cycloalkenyl, alkynyl, aryl, heteroaryl, alkoxy, acyl, alkylamine, arylamine group having 2 to 20 carbon atoms, ether, ester, amide, carbamate, carbonate, formula (3) to formula (7), disulfide containing linker, acid labile linker, photolabile linker, peptidase labile linker, and esterase labile linker, or combinations thereof.

In some embodiments of the disclosure, the payload A and the payload B are independently selected from a therapeutic agent and a label.

Examples of the therapeutic agent include, but are not limited to antimetabolites, alkylating agents, alkylating-like agents, DNA minor groove alkylating agents, anthracyclines, antibiotics, calicheamicins, antimitotic agents, topoisomerase inhibitors, proteasome inhibitors, radioisotopes, and isotope-chelating agents. Examples of specific compounds of the therapeutic agent include, but are not limited to monomethyl auristatin E (MMAE), monomethyl auristatin F (MMAF), maytansinoids, duocarmycin-hydroxy benzamide azaindole (DUBA), diethylenetriamine-N,N,N',N",N"-pentaacetate (DTPA), exatecan, and Dxd2.

Examples of the label include, but are not limited to a fluorescent label, a chromophoric label, an electron-dense label, a chemiluminescent label, a radioactive label, an enzymatic label, and a positron emitter.

An example of the protecting group is azide.

One aspect of the disclosure relates to a pharmaceutical composition comprising the immunoconjugate described above and a pharmaceutically acceptable carrier.

One aspect of the disclosure relates to a method for treating cancers. A method in accordance with one embodiment of the disclosure may comprise administering to a subject in need of cancer treatment a therapeutically effective amount of the immunoconjugate described above.

In some embodiments of the disclosure, the cancer is a mesothelin-expressing cancer. Examples of the cancer include, but are not limited to ovarian cancer, mesothelioma, pancreatic cancer, non-small-cell lung cancer, esophageal cancer, gastric cancer, biliary cancer, colorectal cancer, endometrial cancer, and breast cancer.

One skilled in the art would appreciate that a therapeutically effective amount depends on many factors, such as patient conditions, age, disease states, routs of administration, etc., and that such effective amount may be determined based on these factors in routine practice without undue experimentation.

Other aspect of the disclosure will become apparent with the following description.

BRIEF DESCRIPTION OF THE DRAWINGS

FIGS. 1A and 1B show the sequence alignment of anti-mesothelin antibodies.

DETAILED DESCRIPTION OF THE INVENTION

Figure 2:
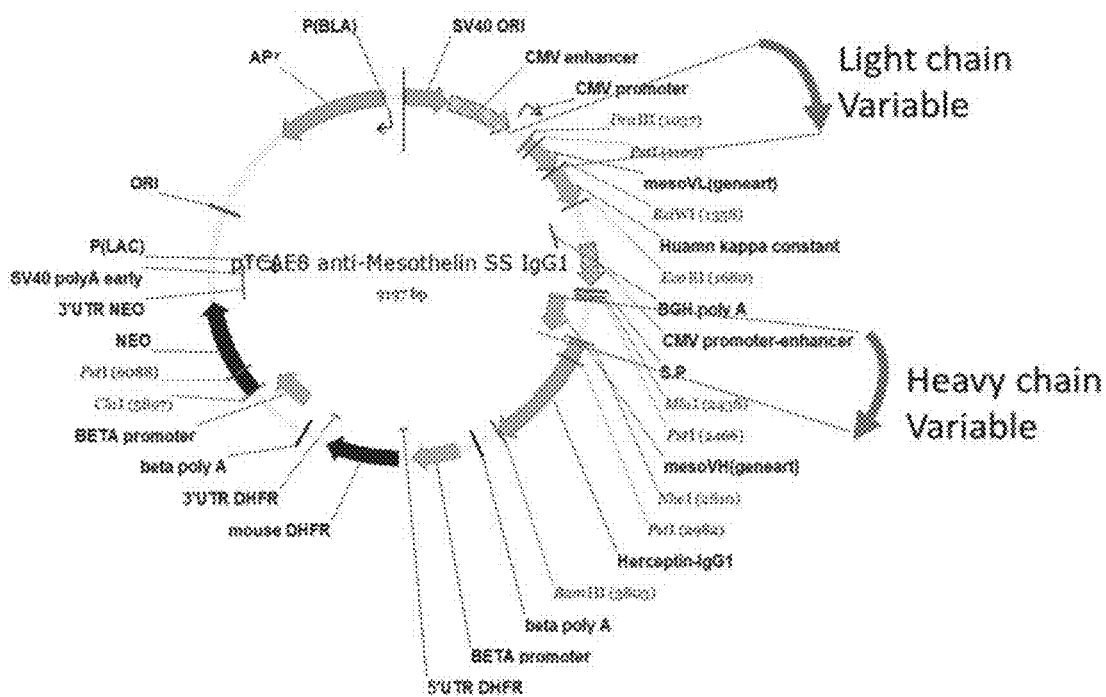
FIG. 2 shows the vector construct expressing the mouse variable region, humanized editions of IMGT and 4D5 variable regions.

It should be noted that as used herein and in the appended claims, the singular forms "a," "an," and "the" include plural reference unless the context clearly dictates otherwise. As well, the terms "a" (or "an"), "one or more" and "at least one" can be used interchangeably herein. It is also to be noted that the terms "comprising," "including," and "having" can be used interchangeably.

Unless defined otherwise, all scientific or technical terms used herein have the same meaning as those understood by persons of ordinary skill in the art to which the present invention belongs. Any method and material similar or equivalent to those described herein can be understood and used by those of ordinary skill in the art to practice the present invention.

It must be noted that, as used in the specification and the appended claims, the singular forms "a," "an" and "the" include plural referents unless the context clearly dictates otherwise. Thus, unless otherwise required by context, singular terms shall include the plural and plural terms shall include the singular.

The term "and/or" is used to refer to both things or either one of the two mentioned.

As used herein, the term "immunoconjugate" refers to a polypeptide molecule that includes at least one effector moiety such as payloads A and B and an antibody. In certain embodiments, the immunoconjugate comprises not more than one effector moiety. Particular immunoconjugates according to the invention essentially consist of one effector moiety and an antibody joined by one or more linkers.

The term "antibody", as used herein, means any antigen-binding molecule or molecular complex comprising at least one complementarity determining region (CDR) that specifically binds to or interacts with a particular antigen (e.g., mesothelin). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_{H1}$, $C_{H2}$ and $C_{H3}$. Each light chain comprises a light chain variable region (abbreviated herein as LCVR or $V_L$) and a light chain constant region. The light chain constant region comprises one domain ($C_{L1}$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the disclosure, the FRs of the anti-α-toxin antibody (or antigen-binding portion thereof) may be identical to the human germline sequences, or may be naturally or artificially modified. An amino acid consensus sequence may be defined based on a side-by-side analysis of two or more CDRs.

The term "monoclonal antibody" as used herein is not limited to antibodies produced through hybridoma technology. A monoclonal antibody is derived from a single clone, including any eukaryotic, prokaryotic, or phage clone, by any means available or known in the art.

"Humanized" forms of non-human antibodies are chimeric immunoglobulins that contain minimal sequences derived from non-human immunoglobulin. In general, a humanized antibody will comprise substantially all of at least one, and typically two, variable domains, in which all or substantially all of the CDR regions correspond to those of a non-human immunoglobulin and all or substantially all of the FR regions are those of a human immunoglobulin sequence.

As used herein, the term "complementarity determining region" (CDR) refers to the non-contiguous antigen combining sites found within the variable region of both heavy and light chain polypeptides. CDRs have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other.

The term "antigen-binding fragment" of an antibody, and the like, as used herein, includes any naturally occurring, enzymatically obtainable, synthetic, or genetically engineered polypeptide or glycoprotein that specifically binds an antigen to form a complex.

As used herein, the term "mesothelin" refers to the 40-kDa protein, mesothelin, which is anchored at the cell membrane by a glycosylphosphatidyl inositol (GPI) linkage and an amino-terminal 31-kDa shed fragment, called megkaryocyte potentiating factor (MPF). Both fragments contain N-glycosylation sites. Preferably, the term refers to a human mesothelin, and naturally cleaved portions thereof, e.g., as expressed on a cell membrane, e.g., a cancer cell membrane. Particularly, a fragment of mesothelin contains N-terminal region of mesothelin.

As used herein, the term "epitope" refers to the site on the antigen to which an antibody binds.

As used herein, the term "N-glycan" refers to an N-linked oligosaccharide, e.g., one that is attached by an asparagine-N-acetylglucosamine linkage to an asparagine residue of a polypeptide. N-glycans have a common pentasaccharide core of $Man_3GlcNAc_2$ ("Man" refers to mannose; "Glc" refers to glucose; and "NAc" refers to N-acetyl; GlcNAc refers to N-acetylglucosamine). The term "trimannose core" used with respect to the N-glycan also refers to the structure $Man_3GlcNAc_2$ ("$Man_3$"). N-glycans differ with respect to the number of branches (antennae) comprising peripheral sugars (e.g., fucose and sialic acid) that are added to the $Man_3$ core structure.

As used herein, the term "pharmaceutical composition" refers to a formulation or preparation comprising an active ingredient having biological or pharmacological activity and a pharmaceutically acceptable carrier. The pharmaceutical composition may be in the form of solutions, suspensions, tablets, powder, pellets, beads, granules, microspheres, capsule, pills and so forth.

The terms "treatment," "treating," and "treat" generally refer to obtaining a desired pharmacological and/or physiological effect. The effect may be preventive in terms of completely or partially preventing a disease, disorder, or symptom thereof, and may be therapeutic in terms of a partial or complete cure for a disease, disorder, and/or symptoms attributed thereto. "Treatment" used herein covers any treatment of a disease in a mammal, preferably a human, and includes (1) suppressing development of a disease, disorder, or symptom thereof in a subject or (2) relieving or ameliorating the disease, disorder, or symptom thereof in a subject.

As used herein, the term "subject" is any animal that can benefit from the administration of a compound or composition as disclosed herein. In some embodiments, the subject is a mammal, for example, a human, a primate, a dog, a cat, a horse, a cow, a pig, a rodent, such as for example a rat or mouse. Typically, the mammal is a human.

The term "effective amount" of an active ingredient as provided herein means a sufficient amount of the ingredient to provide the desired regulation of a desired function. As will be pointed out below, the exact amount required will vary from subject to subject, depending on the disease state, physical conditions, age, sex, species and weight of the subject, the specific identity and formulation of the composition, etc. Dosage regimens may be adjusted to induce the optimum therapeutic response. For example, several divided doses may be administered daily or the dose may be proportionally reduced as indicated by the exigencies of the therapeutic situation. Thus, it is not possible to specify an exact "effective amount." However, an appropriate effective amount can be determined by one of ordinary skill in the art using only routine experimentation.

The term "pharmaceutically acceptable" as used herein refers to compounds, materials, compositions, and/or dosage forms which are, within the scope of sound medical judgment, suitable for use in contact with the tissues of a subject (either a human or non-human animal) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation. Suitable carriers, excipients, etc. can be found in standard pharmaceutical texts.

The immunoconjugate of the present disclosure may be formulated with a "carrier." As used herein, "carrier"

includes any solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. For example, the pharmaceutical combinations can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, lotion, gel, ointment, or a controlled-release patch or spray applied to the skin; (4) intravaginally or intrarectally, for example, as a pessary, cream, suppository or foam; (5) sublingually; (6) ocularly; (7) transdermally; (8) transmucosally; or (9) nasally.

Antibody-drug conjugates (ADCs) are a class of therapeutics, in which a drug (or payload) is attached to an antibody or an antigen-binding fragment thereof. The antibody in an ADC binds to a selected target (typically, a target on a cell), thereby bring the drug to the vicinity of the target, resulting in highly selective therapeutic effects. An example of an ADC may be an antibody targeting a protein expressed on cancer cells, and the payload may be a cytotoxic agent. One embodiment of the disclosure relates to an immunoconjugate (antibody-drug conjugate) containing an anti-mesothelin antibody or a binding fragment thereof, and two or more payloads. In an embodiment of the disclosure, the immunoconjugate comprises an antibody comprising an antigen-binding fragment that specifically binds to an epitope in mesothelin, an N-glycan binding domain and an N-glycan having a structure of formula (1);

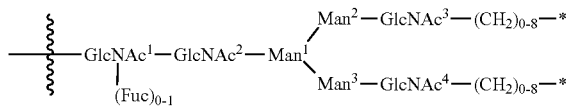

formula (1)

wherein "*" represents a bond or a protecting group;
a linker linking to each of the "*" in the N-glycan when "*" presents the bond; and
a payload A and a payload B independently conjugated to the linkers; wherein the payload A and the payload B are the same or different.

In one embodiment of the disclosure, the N-glyan, linker, and payloads A and B has a structure of formula (2):

In accordance with embodiments of the disclosure, the anti-mesothelin antibody or the binding fragment thereof is capable of recognizing and binding to mesothelin or a fragment thereof. The term antibody herein is used in its broadest sense and specifically includes monoclonal antibodies, polyclonal antibodies, dimers, multimers, multispecific antibodies (e.g. bispecific antibodies), antibody fragments, and double and single chain antibodies. The term "antibody" is herein also meant to include human antibodies, humanized antibodies, chimeric antibodies and antibodies specifically binding mesothelin. The term "antibody" is meant to include whole antibodies, but also fragments of an antibody, for example an antibody Fab fragment, F(ab')$_2$, Fv fragment or Fc fragment from a cleaved antibody, an scFv-Fc fragment, a minibody, a diabody or an scFv. Furthermore, the term includes genetically engineered derivatives of an antibody. Antibodies, fragments of antibodies and genetically engineered antibodies may be obtained by methods that are known in the art.

The antibody as described herein comprises an N-glycan binding domain. In one embodiment, the antibody comprises a heavy chain constant region, and the N-glycan binding domain is located in the heavy chain constant region. In some embodiments, the antibody as described bears N-glycosylation an asparagine residue in the heavy chain of the $C_{H2}$ constant domain of the Fc region. In one embodiment, the antibody comprises two heavy chains, and two N-glycans, each N-glycan binding to one heavy chain. Particularly, the first GlcNAc (GlcNAc$^1$) in the N-glycan as shown in formula (1) bonds to the antibody.

In one embodiment of the disclosure, the antigen-binding fragment of the antibody DCBPR2002 comprises complementarity determining regions (CDRs) of a heavy chain variable region and complementarity determining regions of a light chain variable region, wherein the complementarity determining regions of the heavy chain variable region comprise CDRH1, CDRH2 and CDRH3 regions, and the complementarity determining regions of the light chain variable region comprise CDRL1, CDRL2 and CDRL3 regions; wherein the CDRH1 region comprises the amino acid sequence of SEQ ID NO: 1; the CDRH2 region comprises the amino acid sequence of SEQ ID NO: 2; the CDRH3 region comprises the amino acid sequence of SEQ ID NO: 3; the CDRL1 region comprises the amino acid sequence of SEQ ID NO: 4; the CDRL2 region comprises the amino acid sequence of SEQ ID NO: 5; and the CDRL3 region comprises the amino acid sequence of SEQ ID NO: 6.

In one embodiment of the disclosure, the antibody is a mouse antibody. The mouse anti-mesothelin antibody, clone SS1, has been developed for cancer treatment in clinical trials. The antibody SS1 comprises a heavy chain variable region comprising the amino acid sequence of SEQ ID NO: 7, and a light chain variable region comprising the amino acid sequence of SEQ ID NO: 8, as disclosed in U.S. Pat. No. 7,081,518 B1.

formula (2)

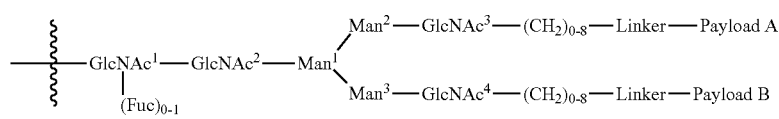

In a further embodiment of the disclosure, the payload A and the payload B are the same or different.

It is oberserved that the SS1-induced potent immunogenicity and anti-drug antibody in patients. Therefore, humanization of SS1 is an essential and critical step for further drug development. For humanized SS1 4D5 (HdSS1) preparation, the human acceptor framework was selected from a framework that has been validated in the clinic. In one embodiment of the disclosure, the antibody HdSS1 comprises a heavy chain variable region comprising the amino acid sequence of SEQ ID NO: 9, and a light chain variable region comprising the amino acid sequence of SEQ ID NO: 10.

In some embodiments of the disclosure, the antibody comprises human germ-line VL and VH sequences with the highest degree of homology with the mAb SS1 framework regions. Particularly, the humanized antibody HuSS1 (DCBPR2002) comprises a heavy chain variable region comprising the amino acid sequence of SEQ ID NO: 11, and a light chain variable region comprising the amino acid sequence of SEQ ID NO: 12, as shown in FIG. 1.

The sequences are listed in Table 1.

represents a tri-mannosyl structure comprising three mannoses, wherein the first mannose ($Man^1$) links to a GlcNAc sugar; and the second and third mannoses ($Man^2$ and $Man^3$) respectively link to $Man^1$ through $\alpha$-1,3 and $\alpha$-1,6 glycosidic linkages.

As used herein, "-$(Fuc)_{0-1}$" represents that a fucose sugar is optionally existing, and when present, there is only one fucose sugar.

The N-glycan as described herein has the structure of formula (1). The process for synthesizing the N-glycan, linker, payloads A and B as shown in formula (2) can be seen at least in WO2018/126092A1.

As used herein, "—$(CH_2)_{0-8}$—" represents that —$CH_2$— may or may not exist, and when present, it may independently be 1, 2, 3, 4, 5, 6, 7 or 8 —$CH_2$— groups.

In some embodiments, the linker has a functionality that is capable of connecting conjugator and payload. Examples of such linkers include, but are not limited to, non-cleavable

TABLE 1

|  | Sequence | SEQ ID NO. |
| --- | --- | --- |
| CDRH1 | GYSFTGYTMN | 1 |
| CDRH2 | LITPYNGASSYNQKFRG | 2 |
| CDRH3 | GGYDGRGFDY | 3 |
| CDRL1 | SASSSVSYMH | 4 |
| CDRL2 | DTSKLAS | 5 |
| CDRL3 | QQWSKHPLT | 6 |
| Heavy chain variable region of SS1 | QVQLQQSGPELEKPGASVKISCKASGYSFTGYTMNWVKQS HGKSLEWIGLITPYNGASSYNQKFRGKATLTVDKSSSTAYM DLLSLTSEDSAVYFCARGGYDGRGFDYWGQGTTVTVSS | 7 |
| Light chain variable region of SS1 | DIELTQSPAIMSASPGEKVTMTCSASSSVSYMHWYQQKSGT SPKRWIYDTSKLASGVPGRFSGSGSGNSYSLTISSVEAEDD ATYYCQQWSKHPLTFGAGTKLEIKR | 8 |
| Heavy chain variable region of HdSS1 | EVQLVESGGGLVQPGGSLRLSCAASGYSFTGYTMNWVRQAP GKGLEWVALITPYNGASSYNQKFRGRFTISRDDSKNTLYLQ MNSLRAEDTAVYYCARGGYDGRGFDYWGQGTLVTVSS | 9 |
| Light chain variable region of HdSS1 | DIQMTQSPSSLSASVGDRVTITCSASSSVSYMHWYQQKPGK APKLLIYDTSKLASGVPSRFSGSGSGTDFTLTISSLQPEDF YATYCQQWSKHPLTFGQGTKVEIKR | 10 |
| Heavy chain variable region of HuSS1 (DCBPR2002) | QVQLVQSGAEVKKPGASVKVSCKASGYSFTGYTMNWVRQAP GQGLEWMGLITPYNGASSYNQKFRGRVTMTRDTSISTAYME LSRLRSDDTAVYYCARGGYDGRGFDYWGQGTLVTVSS | 11 |
| Light chain variable region of HuSS1 (DCBPR2002) | EIVLTQSPATLSLSPGERATLSCSASSSVSYMHWYQQKPGQ APRLLIYDTSKLASGIPARFSGSGSGTDFTLTISSLEPEDF AVYYCQQWSKHPLTFGQGTKVEIKR | 12 |

As used herein, "$GlcNAc^1$," "$GlcNAc^2$," "$GlcNAc^3$," and "$GlcNAc^4$" respectively represent the GlcNAc sugars at different positions of an antenna-shaped glycan moiety.

As used herein,

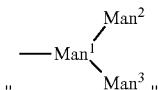

linkers and cleavable linkers. In some embodiments, non-cleavable linkers include, but are not limited to a linear or branched alkyl, cycloalkyl, alkenyl, cycloalkenyl, alkynyl, aryl, heteroaryl, alkoxy, acyl, alkylamine, or arylamine group having 2 to 20 carbon atoms. In some embodiments, cleavable linkers include, but are not limited to disulfide containing linkers, acid labile linkers, photolabile linkers, peptidase labile linkers, and esterase labile linkers. Examples of the linkers include, but are not limited to a linear or branched alkyl, cycloalkyl, alkenyl, cycloalkenyl, alkynyl, aryl, heteroaryl, alkoxy, acyl, alkylamine, arylamine group having 2 to 20 carbon atoms, ether, ester, amide, carbamate, carbonate, formula (3) to formula (7), disulfide containing linker, acid labile linker, photolabile linker, peptidase labile linker, and esterase labile linker. More than one of the above mentioned examples can be used simultaneously in any orders.

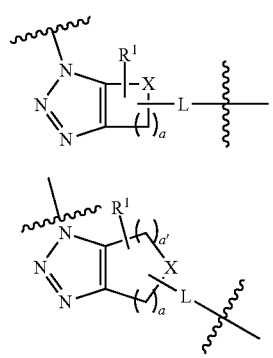

formula (3)

formula (4)

In formula (3) and formula (4):

R$^1$ is independently selected from the group consisting of hydrogen, halogen, —OR$^5$, —NO$_2$, —CN, —S(O)$_2$R$^5$, a C$_1$-C$_{24}$ alkyl group, a C$_6$-C$_{24}$ (hetero)aryl group, a C$_7$-C$_{24}$ alkyl(hetero)aryl group and a C$_7$-C$_{24}$ (hetero)arylalkyl group, and wherein the alkyl group, (hetero)aryl group, alkyl(hetero)aryl group and (hetero)arylalkyl group are optionally substituted, two substituents R$^1$ may be linked together to form an annelated cycloalkyl or an annelated (hetero)arene substituent, and R$^5$ is independently selected from the group consisting of hydrogen, halogen, a C$_1$-C$_{24}$ alkyl group, a C$_6$-C$_{24}$ (hetero)aryl group, a C$_7$-C$_{24}$ alkyl(hetero)aryl group, and a C$_7$-C$_{24}$ (hetero)arylalkyl group;

X is C(R$^1$)$_2$, O, S or NR$^2$, wherein R$^2$ is R$^1$; a is 0, 1, 2, 3, 4, 5, 6, 7 or 8; a' is 0, 1, 2, 3, 4, 5, 6, 7 or 8; and a+a'<10; and L is selected from the group consisting of a linear or branched alkyl, cycloalkyl, alkenyl, cycloalkenyl, alkynyl, aryl, heteroaryl, alkoxy, acyl, alkylamine, arylamine group having 2 to 20 carbon atoms, ether, ester, amide, carbamate, carbonate, disulfide containing linker, acid labile linker, photolabile linker, peptidase labile linker, and esterase labile linker, or combinations thereof.

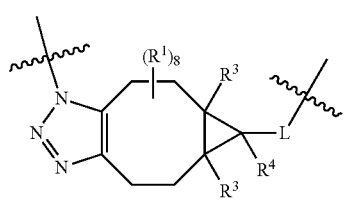

formula (5)

In formula (5):

R$^1$ and L are as defined in formula (3) and formula (4);

R$^3$ is independently selected from the group consisting of hydrogen, halogen, a C$_1$-C$_{24}$ alkyl group, a C$_6$-C$_{24}$ (hetero)aryl group, a C$_7$-C$_{24}$ alkyl(hetero)aryl group and a C$_7$-C$_{24}$ (hetero)arylalkyl group;

R$^4$ is selected from the group consisting of hydrogen, halogen, a C$_1$-C$_{24}$ alkyl group, a C$_6$-C$_{24}$ (hetero)aryl group, a C$_7$-C$_{24}$ alkyl(hetero)aryl group and a C$_7$-C$_{24}$ (hetero)arylalkyl group, the alkyl group optionally being interrupted by one of more hetero-atoms selected from the group consisting of O, N and S, wherein the alkyl group, (hetero)aryl group, alkyl(hetero)aryl group and (hetero)arylalkyl group are independently optionally substituted.

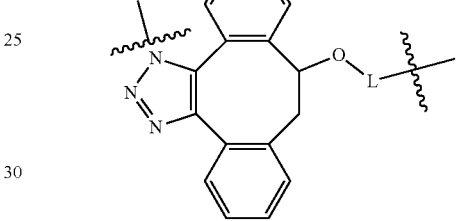

formula (6)

formula (7)

In formula (6) and (7), L is as defined in formula (3) and formula (4).

In some embodiments, when the immunoconjugate is used for the treatment of a disease in a subject, and thus the payloads A and B may independently be a therapeutic agent. The therapeutic agent can be a cytostatic or cytotoxic agent or an isotope-chelating agent with corresponding radioisotopes. Examples of the cytostatic or cytotoxic agent include, without limitation, antimetabolites (e.g., fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, gemcitabine, capecitibine, azathioprine, cytosine methotrexate, trimethoprim, pyrimethamine, or pemetrexed); alkylating agents (e.g., cmelphalan, chlorambucil, busulfan, thiotepa, ifosfamide, carmustine, lomustine, semustine, streptozocin, dacarbazine, mitomycin C, cyclophosphamide, mechlorethamine, uramustine, dibromomannitol, tetranitrate, procarbazine, altretamine, mitozolomide, or temozolomide); alkylating-like agents (e.g., cisplatin, carboplatin, nedaplatin, oxaliplatin, satraplatin, or triplatin); DNA minor groove alkylating agents (e.g., duocarmycins such as CC-1065, and any analogs or derivatives thereof; pyrrolobenzodiazapenes, or any analogs or derivatives thereof); anthracyclines (e.g., daunorubicin, doxorubicin, epirubicin, idarubicin, or valrubicin); antibiotics (e.g., dactinomycin, bleomycin, mithramycin, anthramycin, streptozotocin, gramicidin D, mitomycins (e.g., mitomycin C); calicheamicins; antimitotic agents (including, e.g., maytansinoids (such as DM1, DM3, and DM4), auristatins (including, e.g., monomethyl auristatin E (MMAE) and monomethyl auristatin F (MMAF)), dolastatins, cryptophycins, vinca alkaloids (e.g., vincristine, vinblastine, vindesine, vinorelbine), taxanes (e.g., paclitaxel, docetaxel, or a novel taxane), tubulysins, and colchicines); topoisomerase inhibitors (e.g., irinotecan, topotecan, camptothecin, silatecan, cositecan, exatecan, lurtotecan, gimatecan, belotecan, rubitecan, SN38, DXd, DXd2, etoposide, teniposide, amsacrine, or mitoxantrone); HDAC inhibitor (e.g., vorinostat, romidepsin, chidamide, panobinostat, or belinostat); proteasome inhibitors (e.g., peptidyl boronic acids); as well as radioisotopes such as $At^{211}$, $I^{131}$, $I^{125}$, $Y^{90}$, $Re^{186}$, $Re^{188}$, $Sm^{153}$, $Bi^{212}$ or $^{213}$, $P^{32}$ and radioactive isotopes of Lu including $Lu^{177}$. Examples of the isotope-chelating agents include, without limitation, ethylenediaminetetraacetic acid (EDTA), diethylenetriamine-N,N,N',N'',N''-pentaacetate (DTPA), 1,4,7,10-tetraazacyclododecane-N,N',N'',N'''-tetraacetate (DOTA), 1,4,7,10-tetrakis(2-hydroxypropyl)-1,4,7,10-tetraazacyclododecane (THP), triethylenetetraamine-N,N,N',N'',N''',N'''-hexaacetate (TTHA), 1,4,7,10-tetraazacyclododecane-N,N',N'',N'''-tetrakis (methylenephosphonate) (DOTP), and mercaptoacetyltriglycine (MAG3).

Particularly, the therapeutic agent as used herein is monomethyl auristatin E, monomethyl auristatin F, maytansinoids, duocarmycin-hydroxy benzamide azaindole, diethylenetriamine-N,N,N',N'',N''-pentaacetate, exatecan, or Dxd2.

In some embodiments, when the immunoconjugate is used for detection, the payloads A and B may independently be a label. The labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $P^{32}$, $C^{14}$, $I^{125}$, $H^3$, and $I^{131}$, fluorophores such as rare earth chelates or fluorescein and its derivatives, rhodamine and its derivatives, dansyl, umbelliferone, luceriferases, e.g., firefly luciferase and bacterial luciferase, luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like. In another embodiment, a label is a positron emitter. Positron emitters include but are not limited to $Ga^{68}$, $F^{18}$, $Cu^{64}$, $Y^{86}$, $Br^{76}$, $Zr^{89}$, and $I^{124}$.

In some embodiments of the disclosure, the immunoconjugate may not be fully charged with the payloads A and B and linker, and the N-glycan may directly bind to a protecting group. The protecting group may be further replaced with the therapeutic agent or label. An example of the protecting group is azide.

One embodiment of the disclosure relates to a pharmaceutical composition comprising the immunoconjugate of the disclosure and a pharmaceutically acceptable carrier.

One embodiment of the disclosure relates to methods of treating a disease or disorder using the immunoconjugate of the disclosure. The disease may be a cancer. Particularly, the cancer is a mesothelin-expressing cancer. "Mesothelin-expressing cancer" refers to any cancer with cells that express mesothelin. Mesothelin is generally expressed on solid tumors, including those associated with the lung, pleura, ovary, breast, stomach, bile ducts, uterus, and thymus. Thus, examples of mesothelin-expressing cancers include, but are not limited to, ovarian cancer, mesothelioma, pancreatic cancer, non-small-cell lung cancer, esophageal cancer, gastric cancer, biliary cancer, colorectal cancer, endometrial cancer, and breast cancer. Particularly, the cancer is ovarian cancer.

In some embodiments, the immunoconjugate shows the relatively stable conjugation linkage than random conjugation immunoconjugate based on in vivo pharmacokinetic profile.

In some embodiments, the immunoconjugate with the N-glycan shows better efficacy than the random conjugation immunoconjugate in xenograft animal model.

Embodiments of the disclosure will be illustrated with the following specific examples. One skilled in the art would appreciate that these examples are for illustration only and that other modifications and variations are possible without departing from the scope of the disclosure.

EXAMPLES

Unless otherwise indicated, each $^1$H NMR data were obtained at 500 MHz. The abbreviations used herein are as follows, unless specified otherwise: Az: azide; Bu: butyl; Bn: benzyl; BOC: t-butyloxycarbonyl; BOP: benzotriazol-1-yloxy tri/dimethylamino-phosphonium hexafluorophosphate; DBCO: dibenzocyclooctyne group; DCC: dicyclohexylcarbodiimide; DCM: dichloromethane; DIPEA: N,N-Diisopropylethylamine; DMF: N,N-dimethylformamide; DMAP: 4-dimethylaminopyridine; EDC: 1-(3-dimethylaminopropyl) 3-ethylcarbodiimide hydrochloride; EtOAc: ethyl acetate; eq.: equivalent(s); GlcNAc: N-acetylglucosamine; GlcNAz: azido-N-acetylglucosamine; HBTU:3-[Bis(dimethylamino)methyliumyl]-3H-benzotriazol-1-oxide hexafluorophosphate; Hexafluorophosphate Benzotriazole Tetramethyl Uronium; HOBt: hydroxybenzotriazole; HOSu: N-hydroxysuccinimide; HATU: 1-[Bis(dimethylamino)methylene]-1H-1,2,3-triazolo[4,5-b]pyridinium 3-oxide hexafluorophosphate; Hexafluorophosphate Azabenzotriazole Tetramethyl Uronium; LAH: lithium aluminum hydride; MeOH: methanol; MES: 4-morpholineethanesulfonic acid; MGAT-1: mannosyl (α-1,3-)-glycoprotein β-1,2-N-acetylglucosaminyl transferase; MGAT-2: mannosyl (α-1,6-)-glycoprotein β-1,2-N-acetylglucosaminyl transferase; MHz: megahertz; MMAE: monomethyl auristatin E; MS(ES): mass spectrophotometer-electron spray; NMP: N-methylpyrrolidinone; Ph: phenyl; Pr: propyl; TEA: triethylamine; TFA: trifluoroacetic acid; THF: tetrandrofuran; TLC: thin layer chromatography; Tetrakis: tetrakis(triphenylphosphine)palladium; UDP: uridine diphosphate.

Example 1 Humanization of Anti-Mesothelin SS1, mAb

Selection of Human V Region Framework Sequences:
By using mouse monoclonal antibody SS1, which sequences were disclosed in U.S. Pat. No. 7,081,518 B1, as the parent antibody, SS1 mAb CDR sequences according to the Kabat definitions were described in the FIG. 1A (SEQ ID NOs: 7 and 8).

For humanized SS1 4D5 (HdSS1) preparation, the human acceptor framework was selected from a framework that has been validated in the clinic. Human heavy and light chain framework sequences in the VH subgroup III, IGHV3-66*04 and VL κ subgroup I, IGKV1-39*01 have been validated in the clinic and also been used in many humanized antibodies with success.

As shown in FIG. 1A, the sequences of IGHV3-66*04 heavy chain framework regions differ from those in mAb SS1 by 35 amino acids (the underlined residues), which corresponds to a 42.68% (35/82 total residues in the framework regions) variation. In addition, the sequences of IGKV1-39*01 (VL) light chain framework regions differ from those in mAb SS1 by 25 amino acids (the undelined residues), which corresponds to a 30.86% (25/81 total residues in the framework regions) variation.

For humanized SS1 IMGT (HuSS1) preparation, human germ-line VL and VH sequences with the highest degree of homology with the mAb SS1 framework regions were identified from the IMGT database (the International immunogenetics Information System®). The homology searches may be performed with BLAST or similar methods. These researches identified the human germline gene IGHV1-2*02 (VH) and IGVK3-11*01 (VL), respectively, as the VH and VL sequences most homologous to the corresponding heavy chain and light chain framework sequences in mAb SS1.

As shown in FIG. 1B, the sequences of IGHV1-2*02 heavy chain framework regions differ from those in mAb SS1 by 25 amino acids (the underlined residues), which corresponds to a 30.49% (25/82 total residues in the framework regions) variation. As shown in FIG. 1B, the sequences of IGVK3-11*01 (VL) light chain framework regions differ from those in mAb SS1 by 27 amino acids (the underlined residues), which correspond to a 33.33% (27/81 total residues in the framework regions) variation.

These two pairs of light chain and heavy chain sequences (hum 4D5 and hum IMGT) were used as examples for the construction of humanized antibodies against human mesothelin. (SEQ ID NOs: 9, 10, 11, and 12)

Example 2 Binding Affinity Analysis of Humanized Antibodies

Expression of Full Length Antibodies

To confirm the affinity change after the mouse antibodies were humanized, the variable regions of humanized light chain and humanized heavy chains of IMGT and 4D5 editions were directly generated by the nucleotide synthesis method, respectively. The mouse variable region, humanized editions of IMGT (SEQ ID NOs: 11 and 12) and 4D5 (SEQ ID NOs: 9 and 10) variable regions were sub-cloned into a human Fc chimera antibody expression vector pTCAE8, as shown in FIG. 2, were introduced into host cells to prepare recombinant antibody-expressing cells. As the host cells for expression, the FreeStyle293 cells (manufactured by Invitrogen) were used.

The following procedures are used to transfect the vector thus constructed into suspensions of FreeStyle™ 293 cells in a 30 ml volume. The cells may be kept in FreeStyle™ 293 Expression Medium during transfection. Approximately 24 hrs before transfection, the FreeStyle™ 293 cells were passed at $2 \times 10^6$ cells/ml for 15 ml. The flask(s) was placed in an incubator at 37° C. containing 8% $CO_2$. Then, 37.5 μg of plasmid DNA was diluted into 1.5 ml sterile 150 mM NaCl to a total volume of 1.5 ml. In a separate tube, 37.5 μl of PEI (2.0 mg/ml) was diluted in 1.5 ml sterile 150 mM NaCl. The DNA and PEI solutions were allowed to sit at room temp for 5 minutes. The solutions were mixed gently by inverting the tubes and then allowed the tubes to stand at room temp for around 10-20 minutes. DNA-PEI mixture was added into F293 cells and incubated the transfected cell on an orbital shaker platform rotating at 135-150 rpm at 37° C., 8% $CO_2$ in an incubator for 4 hours. Then, an equal volume of fresh culture medium was added to a total volume of 30 ml, and the cells were cultured for 5-7 days. Cells were then harvested for antibody purification and quantification.

The collected supernatant was filtered through 0.2 micrometer filters (manufactured by Millpore) to remove contaminants. The culture supernatant containing the antibody was affinity-purified using Protein A (manufactured by Millipore), 1.5 M Glycine/NaOH buffer, 3 M NaCl, (pH 9.0) as an absorption buffer, and 0.2 M Glycine/HCl buffer (pH 2.5) as an elution buffer. The elution fractions were adjusted to around pH 6.0~7.0 by adding1 M Tris/HCl buffer (pH 9.0). The prepared antibody solution was replaced with PBS using a dialysis membrane (10,000 MW cut, manufactured by Spectrum Laboratories) and filter-sterilized through a membrane filter (manufactured by Millpore) having a pore size of 0.22 micrometer to yield the purified antibody. The concentration of the purified antibody was determined by measuring the absorbance at 280 nm and converted the measured value based on 1.45 optimal density equaling 1 mg/ml.

Determination of Antibody Binding Affinity by ELISA

ELISA plates were coated with 1~2 μg/100 μl per well of mesothelin protein. Wells were rinsed for 3 times with PBS and blocked with 300 μl 5% MPBS per well for 2 hr at 37° C. After washing with PBS, wells were incubated with serial diluted mesothelin antibodies in 5% MPBS for 1.5 hours at 37° C. The plates were washed and goat polyclonal anti-human IgG-HRP antibody (1:10,000) (Jackson ImmunoResearch) was added into each well. The absorbance was measured as described above and the binding affinities of antibodies were calculated by non-linear regression with Prism software (GraphPad).

Figure 3:
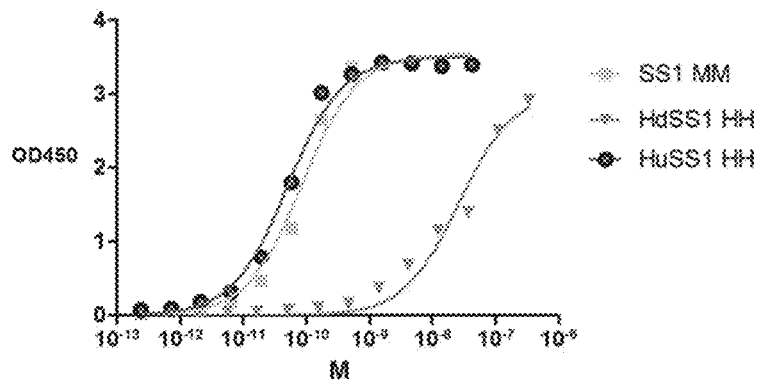
FIG. 3 shows the mesothelin affinity to the antibodies.

With high degrees of variations in the framework regions, HdSS1 (HH) generated by grafting CDR sequences from mAb SS1 into the IGHV3-66*04 and IGVK1-39*01 sequences shows much lower affinity for mesothelin (KD=2.61E-08 M) (for comparison, mAB SS1, KD=8.36E-11M) (FIG. 3), (Table 2 below).

In contrast to HdSS1, with high degrees of variations in the framework regions, HuSS1 (HH) generated by grafting CDR sequences from mAb SS1 into the IGHV1-2*02 and IGVK3-11*01 sequences has a relatively good affinity for mesothelin (KD=4.99E-11 M) (for comparison, mAB SS1, KD=8.36E-11M) (FIG. 3) (Table 2 below).

These results suggest that IGHV1-2*02 heavy chain framework regions and IGVK3-11*01 light chain framework regions superiorly tolerate a relatively high degree of variations without impacting the CDR region conformations.

TABLE 2

| | ELISA KD (M) |
|---|---|
| SS1 MM | 8.36E−11 |
| HdSS1 HH | 2.61E−08 |
| HuSS1-HH | 4.99E−11 |

Affinity Measurements and Kinetic Analysis Using BIAcore

To know the biding kinetics difference among individual antibodies, surface plasmon resonance (SPR) measurement with a BIAcore T200 (Cytiva Inc.) was used as previously described (Karlsson & Falt, (1997) J. Immunol Methods 200:121-133). Carboxymethylated dextran biosensor chips (CM5, Cytiva Inc.) were activated with N-ethyl-N'-(3-dimethylaminopropyl)-carbodiimide hydrochloride (EDC) and N-hydroxysuccinimide (NHS) according to the supplier's instructions. Mesothelin protein was diluted with 10 mM sodium acetate, pH 4.0, into 5 μg/ml before injection at a flow rate of 10 μL/minute to achieve approximately 1500 response units (RU) of coupled protein followed by the injection of 1M ethanolamine to block unreacted groups. For kinetics measurements, two-fold serial dilutions of anti-mesothelin mAb (0.3125 nM to 40 nM) were injected in HBS-EP+ Biacore running buffer provided by the manufacturer (Cytiva Inc.) at 25 degree C. at a flow rate of 30 µL/min, and binding responses on the mesothelin protein were corrected by subtraction of responses on a blank flow cell. Association rates (kon or ka) and dissociation rates (koff or kd) were calculated using a simple one-to-one Langmuir binding model with separate fittings of kon and koff was used. (Cytiva.™. Biacore Insight Evaluation Software).

Figure 4:
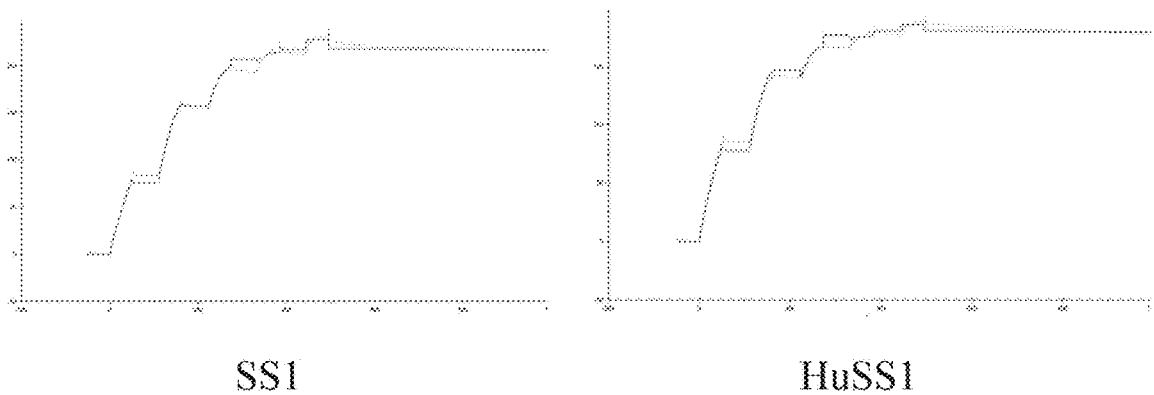
FIG. 4 shows kinetic analysis using BIAcore of SS1 and HuSS1 antibodies.

The results are shown in the FIG. 4 and Table 3 (bellow). The kon and koff of chimera SS1 mAb binding with mesothelin are 3.415E6 and 1.194E-5, respectively, and KD is 3.496E-12 mol/L. The kon and koff of HuSS1mAb (IMGT edition) binding with mesothelin are 4.493E6 and 1.124E-5, respectively, and KD is 2.501E-12.

From the result of FIG. 4, it suggests that humanized antibodies HuSS1 (DCBPR2002) can recognize the human mesothelin protein and after humanization, the affinity of IMGT edition is similar to that of mouse SS1 antibody and has a favor affinity with a KD value of about 2.501E-12.

TABLE 3

|  | ka(1/Ms) | kd(1/s) | KD(M) | Rmax(RU) | Chi$^2$(RU$^2$) |
| --- | --- | --- | --- | --- | --- |
| SS1 | 3.415E+6 | 1.194E−5 | 3.496E−12 | 218.2 | 20.3 |
| HuSS1 | 4.493E+6 | 1.124E−5 | 2.501E−12 | 180.6 | 17.9 |

Example 3 Preparation of Trimannosly-DCBPR2002 (DCBPR2002-TM)

In order to remove galactose and sialic acid moieties of the N-glycan from DCBPR2002, 10 mg of DCBPR2002 was treated with 20 µl β1,4-Galactosidase (NEB, P0745L, 8 unit/µl) and 5 µl α2-3,6,8 neuraminidase (NEB, P0720L, 50 unit/µl) in 1× GlycoBuffer (NEB, total volume 1 mL) at 37° C. for 24 hours. 10 µl of β1,4-Galactosidase (NEB, P0745L, 8 unit/µl) was further added to the reactant and the reaction was allowed to perform at 37° C. for further 24 hours to obtain a GOF/G0 antibody sample. The antibody sample was purified by using rProtein A Sepharose Fast Flow (GE Healthcare, 17-1279-02). After purification, the antibody sample was subjected to reduced mass chromatography analysis.

Figure 21A:
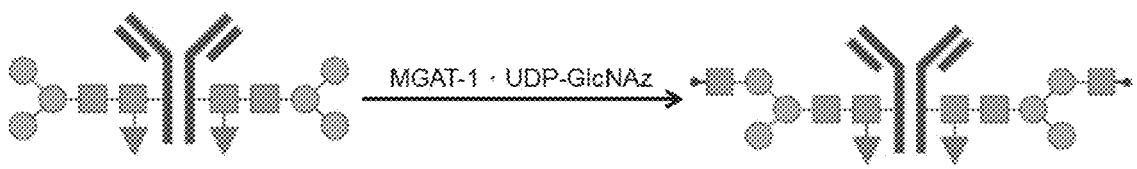
FIGS. 21A to 21T show the preparations of the immunoconjugates. A: Preparation of DCBPR2002-2Az. B: Preparation of DCBPR2002-4Az. C: Preparation of DCBPR2002-4(DBCO-vc-MMAE). D: Preparation of DCBPR2002-4(DBCO-S-DM1). E: Preparation of DCBPR2002-4(DBCO-vc-seco DUBA). F: DCBPR2002-4(DBCO-PEG4-vc-PAB-MMAF). G: Preparation of DCBPR2002-4(DBCO-DTPA). H: Preparation of DCBPR2002-4(DBCO-PEG3-vc-exatecan). I: Preparation of DCBPR2002-4(DBCO-PEG3-GGFG-exatecan). J: Preparation of DCBPR2002-4(DBCO-PEG12-GGFG-exatecan). K: Preparation of DCBPR2002-4(DBCO-PEG3-GGFG-DXd2). L: Preparation of DCBPR2002-4(DBCO-PEG12-GGFG-DXd2). M: Preparation of DCBPR2002-4(BCN-PEG3-VC-PAB-MMAE). N: Preparation of DCBPR2002-4(BCN-PEG12-GGFG-exatecan). O: Preparation of DCBPR2002-4(BCN-PEG3-GGFG-exatecan). P: Preparation of DCBPR2002-4(BCN-PEG12-GGFG-DXd2). Q: Preparation of DCBPR2002-4(DBCO-PEG3-2(PEG3-VC-PAB-MMAE)). R: Preparation of DCBPR2002-2(DBCO-vc-MMAE)-2(DBCO-vc-seco DUBA). S: Preparation of DCBPR2002-2(DBCO-vc-MMAE)-2(DBCO-S-DM1). T: Preparation of DCBPR2002-2(DBCO-vc-seco DUBA)-2(DBCO-S-DM1). ■: GlcNAc. ▼: Man. ●: Fuc.

Preparation of DCBPR2002-2Az (FIG. 21A)

MGAT-1 transfers UDP-azido-N-acetylglucosamine to one of terminal mannose of each arm of tri-mannosyl core protein. To confirm this phenomena in antibodies, trimannosly-DCBPR2002 (5 mg) and UDP-GlcNAz (final concentration of 2.5 mg) in 1000 µl 1× buffer SP (25 mM MES (4-morpholineethanesulfonic acid), 10 mM MnCl$_2$, pH 6.5) were incubated in the presence of MGAT-1 (0.1 mg; R&D, 8334-GT or homemaded) at 37° C. for 16 hours. The product DCBPR2002-2Az was subjected to a reduced mass chromatography analysis.

Figure 21B:
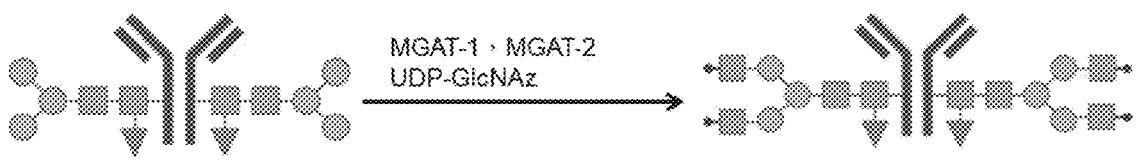

Preparation of DCBPR2002-4Az (FIG. 21B)

Trimannosly-DCBPR2002 (5 mg) and UDP-GlcNAz (2.5 mg) in 800 µl 1× buffer SP (25 mM MES, 10 mM MnCl$_2$, pH 6.5) were incubated in the presence of rabbit MGAT-1 (0.2 mg) and rat MGAT-2 (0.05 mg) at 37° C. for 16 hours. After the incubation, the reaction product DCBPR2002-4Az was subjected to a reduced mass chromatography analysis and an intact mass chromatography analysis.

Example 4 Preparation of DBCO-VC-MMAE (Compound 5)

Synthesis of Compound 3

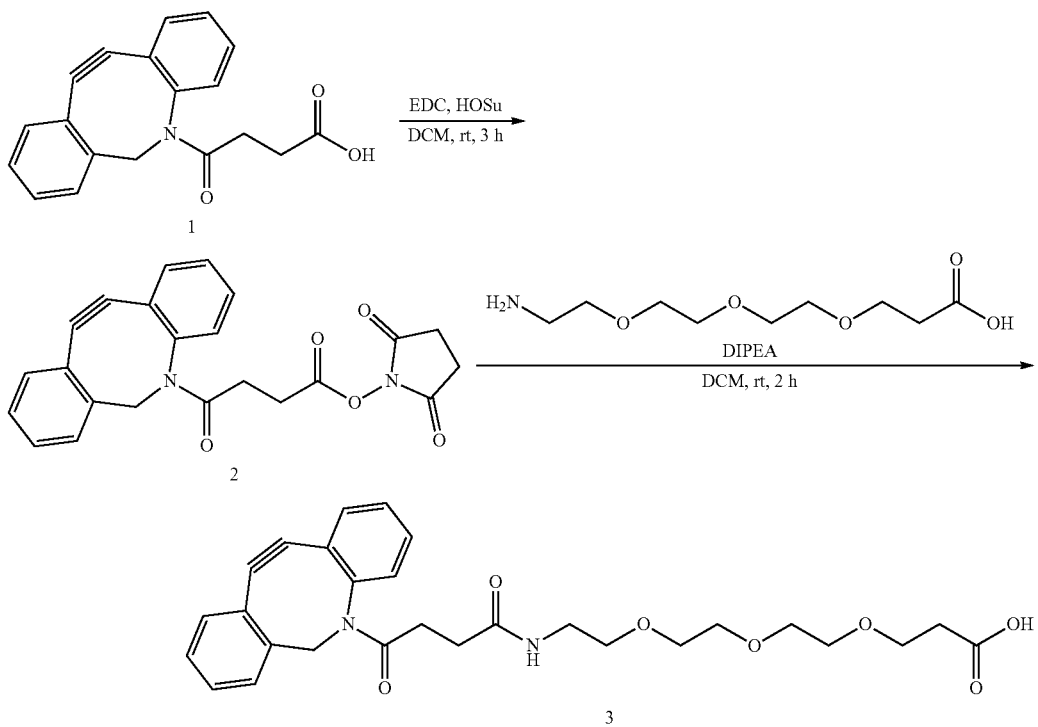

The mixture of DBCO-CO₂H (1) (200 mg, 1 eq), EDC (226 mg, 3 eq), and HOSu (376 mg, 3 eq) was dissolved in dichloromethane (5 mL) and stirred for 3 hours at room temperature. After the reaction was complete, the reaction mixture was extracted with dichloromethane and water. Then, the organic layer was washed with brine and dried over MgSO₄. The organic solvent was removed under reduced pressure to afford compound 2 without further purification.

DIPEA (170 mg, 2 eq) was added to a mixture of compound 2 (1 eq) and 3-(2-(2-(2-aminoethoxy)ethoxy)ethoxy)propanoic acid (174 mg, 1.2 eq) in dichloromethane (5 mL). The reaction mixture was stirred overnight at room temperature. After the reaction was complete, the reaction mixture was extracted with dichloromethane and 1N HCl (aq). Then, the organic layer was washed with brine and dried over MgSO₄. The residue was purified by column chromatography with methanol/dichloromethane to afford a brown liquid compound 3 (54% yield). ¹H NMR (600 MHz, DMSO) δ 7.69 (dd, J=7.7, 1.3 Hz, 1H), 7.63 (d, J=7.4 Hz, 1H), 7.53-7.44 (m, 3H), 7.39 (td, J=7.5, 1.6 Hz, 1H), 7.35 (td, J=7.5, 1.3 Hz, 1H), 7.30 (dd, J=7.4, 1.6 Hz, 1H), 5.04 (d, J=14.0 Hz, 1H), 3.62 (d, J=14.0 Hz, 1H), 3.58 (t, J=6.4 Hz, 2H), 3.48-3.43 (m, 8H), 3.29 (dd, J=5.9, 2.3 Hz, 2H), 3.13-3.04 (m, 2H), 2.61-2.55 (m, 1H), 2.42 (t, J=6.4 Hz, 2H), 2.24 (dt, J=15.5, 7.8 Hz, 1H), 2.00 (ddd, J=15.4, 8.2, 5.7 Hz, 1H), 1.76 (ddd, J=16.3, 8.0, 5.7 Hz, 1H). LC-MS (ESI): m/z Calcd for [C₂₈H₃₂N₂O₇] 509.2 [M+1]⁺, found 509.2[M+1]⁺.

Synthesis of DBCO-VC-MMAE (Compound 5)

DIPEA (145 mg, 2 eq) was added to a mixture of compound 3 (286 mg, 1 eq), vc-MMAE (compound 4) (630 mg, 1.1 eq) and HATU (428 mg, 2 eq) in DCM: DMF 2:1 (6 mL). The mixture was stirred for 1 hour at room temperature. After the reaction was complete, the reaction mixture was extracted with dichloromethane and water. Then, the organic layer was washed with brine and dried over MgSO₄. The organic solvent was removed under reduced pressure. The residue was purified by column chromatography with methanol/dichloromethane to afford a pale yellow solid compound 5 (71% yield). ¹H NMR (600 MHz, MeOD) δ 7.66 (d, J=7.4 Hz, 1H), 7.61 (d, J=3.5 Hz, 3H), 7.51-7.44 (m, 3H), 7.42-7.37 (m, 3H), 7.33 (dt, J=15.5, 8.2 Hz, 5H), 7.26 (d, J=7.3 Hz, 1H), 7.23 (t, J=7.4 Hz, 1H), 5.23-5.07 (m, 3H), 4.71-4.48 (m, 4H), 4.29-4.15 (m, 4H), 3.75-3.69 (m, 3H), 3.63-3.54 (m, 8H), 3.46-3.39 (m, 3H), 3.36 (s, 4H), 3.30 (d, J=16.5 Hz, 3H), 3.26-3.23 (m, 2H), 3.23-3.16 (m, 2H), 3.12 (s, 2H), 2.96 (dd, J=17.0, 10.0 Hz, 3H), 2.75-2.68 (m, 1H), 2.57-2.46 (m, 4H), 2.38 (dt, J=15.0, 7.5 Hz, 1H), 2.28-2.04 (m, 5H), 2.04-1.66 (m, 8H), 1.66-1.49 (m, 4H), 1.45 (d, J=29.4 Hz, 2H), 1.19 (dd, J=6.6, 3.0 Hz, 3H), 1.15 (dd, J=12.8, 6.8 Hz, 3H), 1.03-0.70 (m, 24H).

3 +

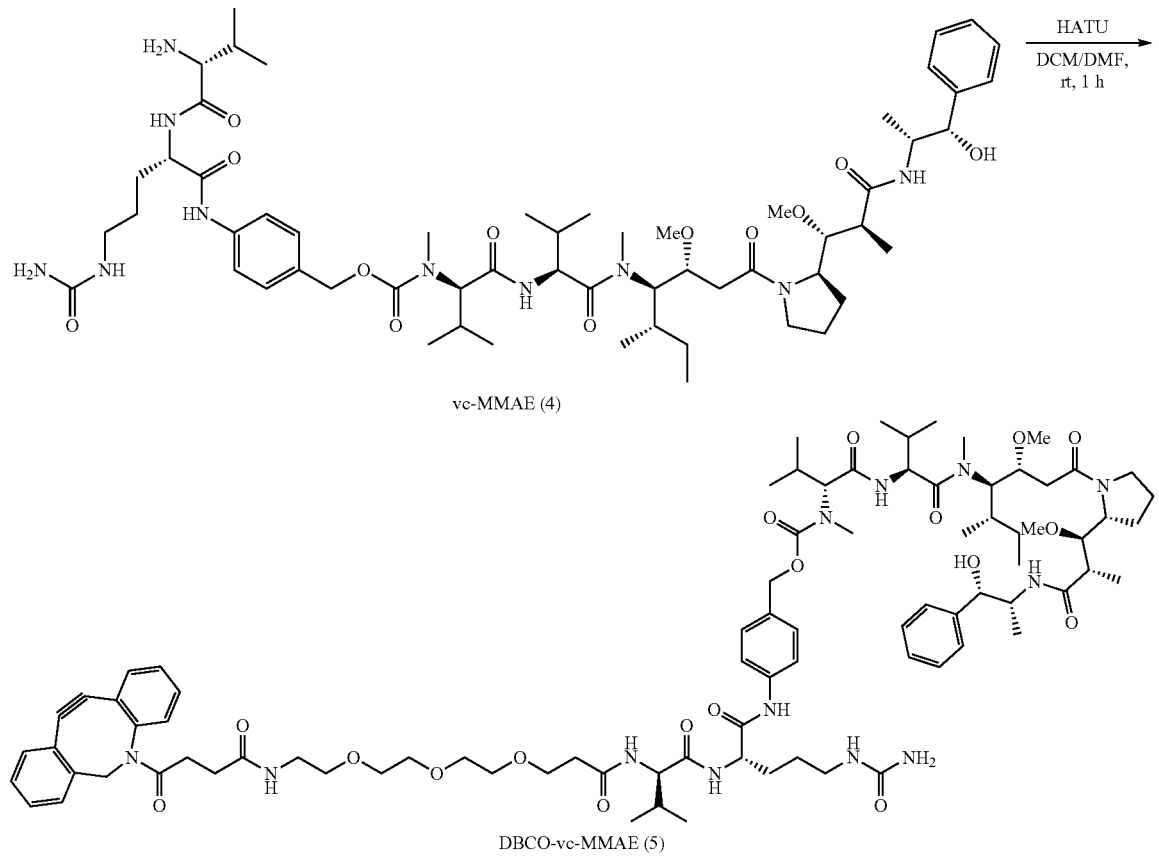

vc-MMAE (4)

DBCO-vc-MMAE (5)

Example 5 Preparation of DBCO-S-DM1 (Compound 11)

Synthesis of Compound 7

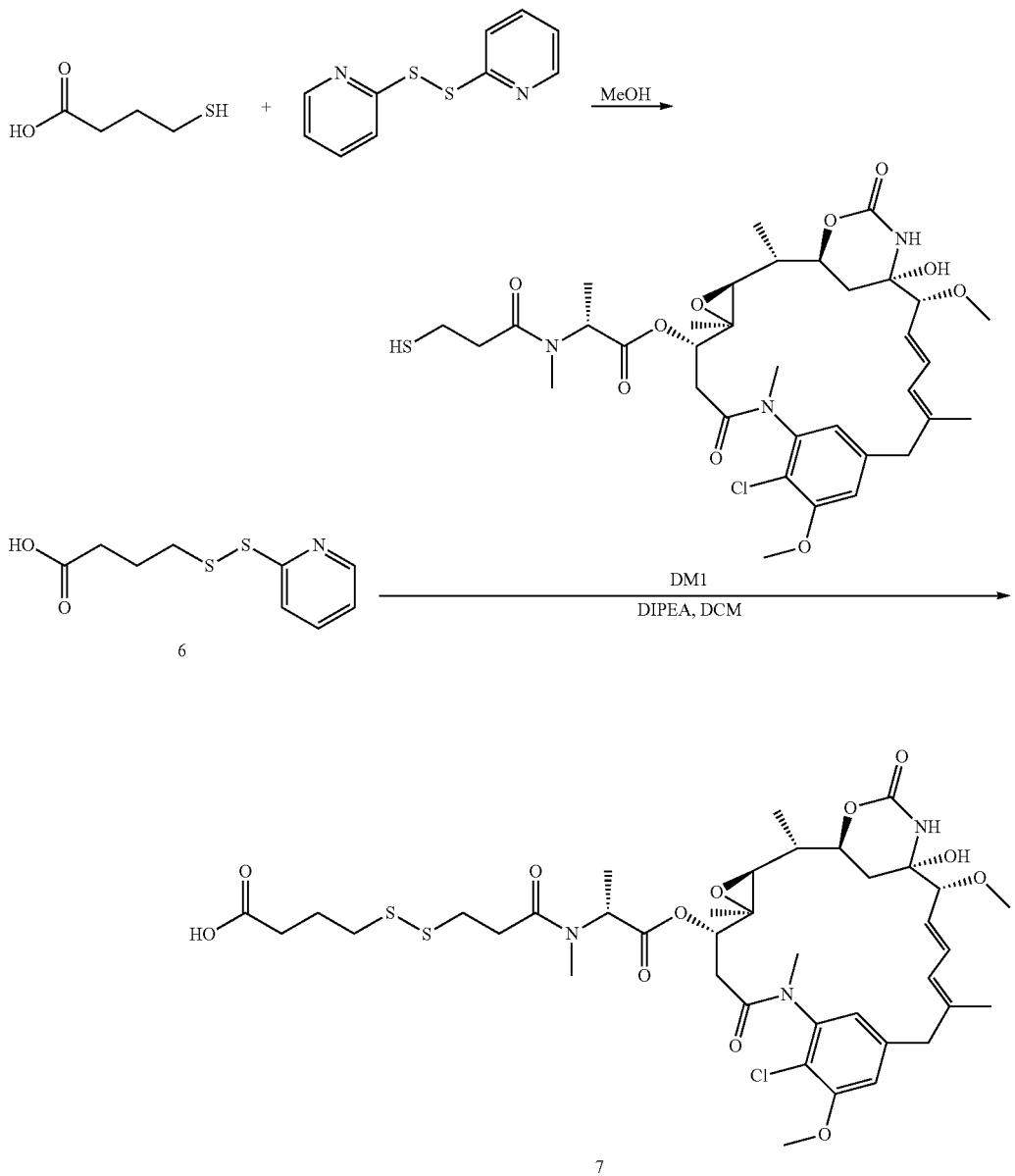

1,2-di(pyridin-2-yl)disulfane (1.83 g, 2 eq) was added to a solution of 4-mercaptobutanoic acid (0.5 g, 1 eq) in methanol (10 mL). The mixture was stirred for overnight at room temperature. After the reaction was completed, the organic solvent was removed under reduced pressure. The residue was purified by column chromatography with hexane/ethyl acetate to afford colorless liquid compound 6 (14% yield). $^1$H NMR (600 MHz, CDCl$_3$) δ 8.49 (ddd, J=4.8, 1.8, 0.9 Hz, 1H), 7.72 (dt, J=8.1, 1.0 Hz, 1H), 7.69-7.61 (m, 1H), 7.12 (ddd, J=7.3, 4.9, 1.1 Hz, 1H), 2.88 (t, J=7.1 Hz, 2H), 2.53 (t, J=7.2 Hz, 2H), 2.07 (p, J=7.2 Hz, 2H).

DIPEA (145 mg, 2 eq) was added to a mixture of compound 6 (286 mg, 1 eq), vc-MMAE (4) (630 mg, 1.1 eq) and HATU (428 mg, 2 eq) in DCM (5 mL). The mixture was stirred for 1 hour at room temperature. After the reaction was complete, the reaction mixture was extracted with dichloromethane and water. Then, the organic layer was washed with brine and dried over MgSO$_4$. The organic solvent was removed under reduced pressure. The residue was purified by column chromatography with methanol/dichloromethane to afford a pale yellow solid compound 7 (71% yield). 1H NMR (600 MHz, DMSO) δ 7.18 (d, J=1.5 Hz, 1H), 6.90 (s, 1H), 6.62-6.56 (m, 1H), 6.56-6.52 (m, 1H), 5.94 (s, 1H), 5.56 (dd, J=14.8, 9.0 Hz, 1H), 5.31 (q, J=6.8 Hz, 1H), 4.52 (dd, J=12.0, 2.7 Hz, 1H), 4.06 (t, J=12.3 Hz, 1H), 3.92 (s, 3H), 3.52-3.45 (m, 2H), 3.25 (s, 3H), 3.13 (s, 3H), 2.93-2.78 (m, 4H), 2.72 (s, 3H), 2.21 (t, J=7.2 Hz, 2H), 2.04 (dd, J=14.4, 2.4 Hz, 1H), 1.69 (p, J=7.4 Hz, 2H), 1.59 (s, 3H), 1.50-1.40 (m, 2H), 1.14 (dd, J=28.7, 6.6 Hz, 6H), 0.97 (d, J=6.4 Hz, 6H), 0.78 (s, 3H).

Synthesis of Compound 9

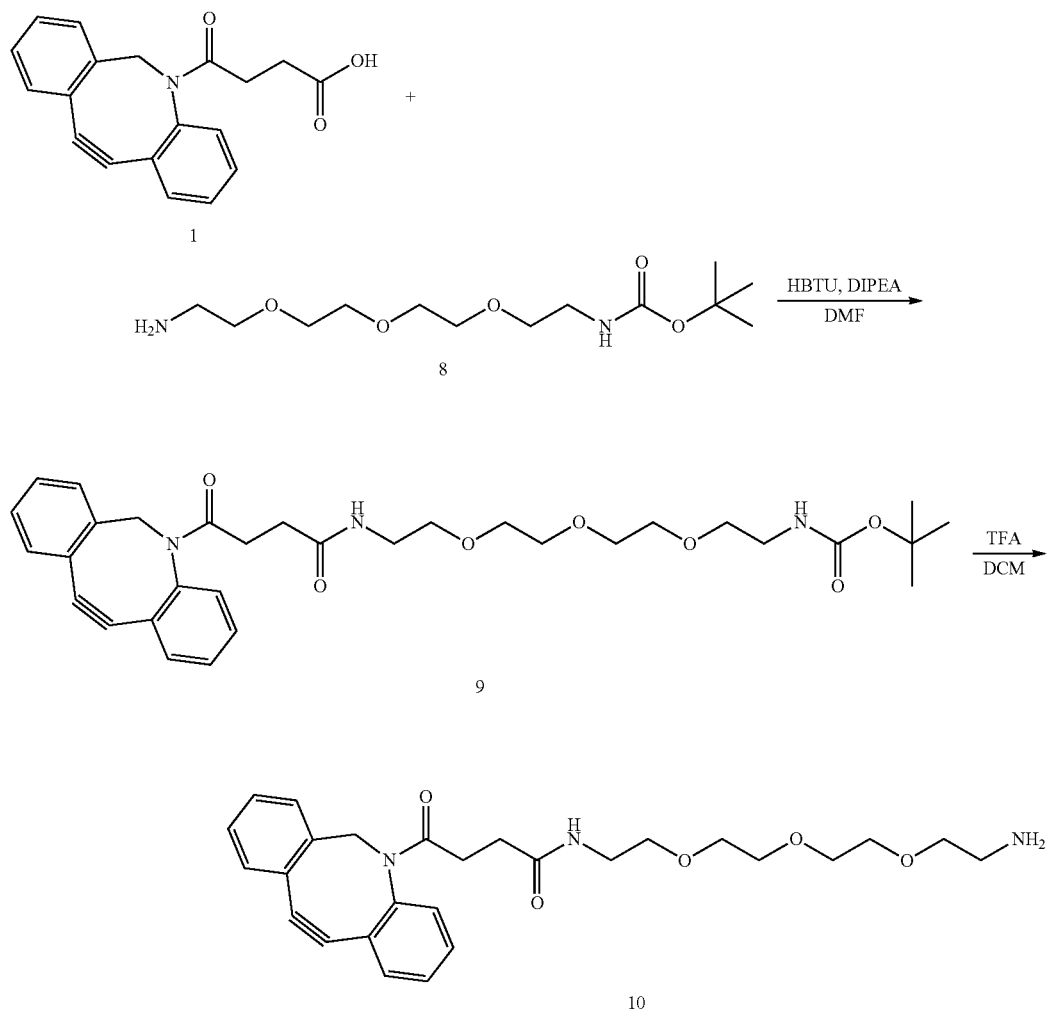

HBTU (0.92 g, 1.5 eq) and DIPEA (0.57 mL, 2 eq) were added to a mixture of compound 1 (0.5 g, 1 eq) and compound 8 (0.62 g, 1.3 eq) in DMF (8 mL). The reaction mixture was stirred 2 hours at room temperature. After the reaction was complete, the reaction mixture was extracted with ethyl acetate and water. Then, the organic layer was washed with brine and dried over MgSO$_4$. The residue was purified by column chromatography with methanol/dichloromethane to afford orange liquid compound 9 (76% yield). LC-MS(ESI): m/z Calcd for [C$_{32}$H$_{41}$N$_3$O$_7$] 579.68 [M+1]$^+$, found 479.95[M+1]$^+$.

Synthesis of compound 10

TFA (2.85 mL) was added to a solution of compound 9 (0.72 g, 1 eq) in dichloromethane (15 mL) under ice bath. The reaction mixture was stirred 3 hours at room temperature. After the reaction was complete, the organic solvent was removed under reduced pressure. The residue was purified by column chromatography with methanol/dichloromethane to afford brown solid compound 10 (69% yield). H NMR (600 MHz, DMSO) δ 7.78-7.74 (m, 2H), 7.69-7.66 (m, 1H), 7.62 (d, J=7.4 Hz, 1H), 7.52-7.45 (m, 2H), 7.40-7.33 (m, 2H), 7.30 (dd, J=7.4, 1.2 Hz, 1H), 5.03 (d, J=14.1 Hz, 1H), 3.62 (d, J=14.0 Hz, 1H), 3.57-3.53 (m, 6H), 3.49-3.44 (m, 6H), 3.30 (td, J=6.0, 1.8 Hz, 2H), 3.12-3.04 (m, 2H), 2.96 (dd, J=10.7, 5.5 Hz, 2H), 2.59 (ddd, J=24.2, 9.8, 4.7 Hz, 1H), 2.23 (dt, J=15.4, 7.6 Hz, 1H), 2.04-1.96 (m, 1H), 1.76 (ddd, J=16.4, 8.0, 5.8 Hz, 1H). LC-MS(ESI): m/z Calcd for [C$_{27}$H$_{33}$N$_3$O$_5$] 479.57 [M+1]$^+$, found 480.1 [M+1]$^+$.

Synthesis of DBCO-S-DM1 (Compound 11)

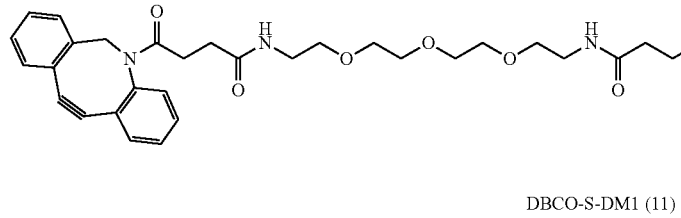
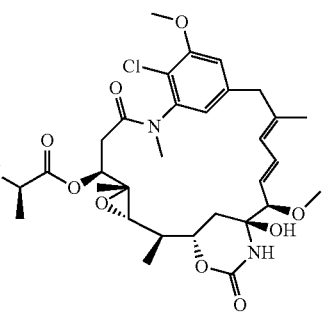

DBCO-S-DM1 (11)

HBTU (77 mg, 1.5 eq) and DIPEA (0.047 mL, 2 eq) were added to a mixture of compound 7 (70 mg, 1 eq) and compound 10 (100 mg, 0.9 eq) in DMF (7 mL). The reaction mixture was stirred overnight at room temperature. After the reaction was complete, the reaction mixture was extracted with ethyl acetate and water. Then, the organic layer was washed with brine and dried over MgSO$_4$. The residue was purified by column chromatography with methanol/dichloromethane to afford orange solid compound 11 (DBCO-S-DM1) (54% yield). 1H NMR (600 MHz, DMSO) δ 7.86 (t, J=5.6 Hz, 1H), 7.76 (t, J=5.6 Hz, 1H), 7.70-7.66 (m, 1H), 7.62 (d, J=7.3 Hz, 1H), 7.52-7.43 (m, 2H), 7.40-7.32 (m, 2H), 7.29 (d, J=7.4 Hz, 1H), 7.17 (s, 1H), 6.90 (s, 1H), 6.63-6.56 (m, 1H), 6.55-6.52 (m, 1H), 5.94 (s, 1H), 5.56 (dd, J=14.8, 9.0 Hz, 1H), 5.31 (q, J=6.8 Hz, 1H), 5.02 (d, J=14.0 Hz, 1H), 4.52 (dd, J=12.1, 2.7 Hz, 1H), 4.06 (t, J=12.3 Hz, 1H), 3.93 (d, J=8.8 Hz, 3H), 3.61 (d, J=14.0 Hz, 1H), 3.47 (s, 9H), 3.37 (t, J=5.9 Hz, 2H), 3.29 (td, J=5.9, 2.2 Hz, 2H), 3.24 (s, 3H), 3.17 (dt, J=11.6, 9.2 Hz, 3H), 3.12 (s, 2H), 3.10-3.02 (m, 2H), 2.88 (ddd, J=15.9, 12.2, 5.3 Hz, 2H), 2.84-2.81 (m, 1H), 2.81-2.78 (m, 1H), 2.71 (s, 2H), 2.60-2.53 (m, 2H), 2.53-2.51 (m, 5H), 2.48-2.44 (m, 3H), 2.23 (dt, J=15.5, 7.8 Hz, 1H), 2.07 (td, J=7.0, 2.7 Hz, 2H), 2.00 (ddd, J=15.3, 12.4, 8.4 Hz, 2H), 1.76 (ddd, J=16.4, 7.9, 5.7 Hz, 1H), 1.71-1.65 (m, 2H), 1.59 (s, 2H), 1.50-1.41 (m, 2H), 1.24 (dd, J=6.9, 5.8 Hz, 2H), 1.17 (d, J=6.8 Hz, 3H), 1.12 (d, J=6.4 Hz, 3H), 0.84 (ddd, J=13.1, 9.9, 6.7 Hz, 1H), 0.78 (s, 2H). LC-MS(ESI): m/z Calcd for [C$_{66}$H$_{85}$ClN$_6$O$_{16}$S$_2$] 1317.99 [M+1]$^+$, found 1299.41 [M−18]$^+$.

Example 6 Preparation of DBCO-VC-Seco DUBA (Compound 20)

Synthesis of Compound 12

Compound 12 was prepared as described by Beusker, P. H. (Mol. Pharmaceutics 2015, 12, 1813-1835).

Synthesis of Compound 14

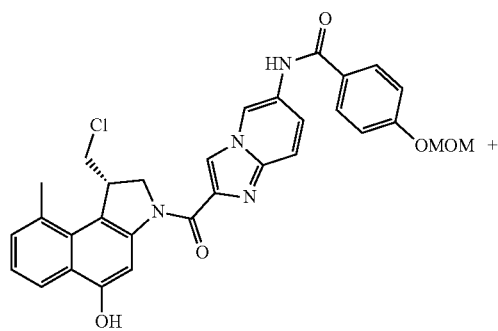

12

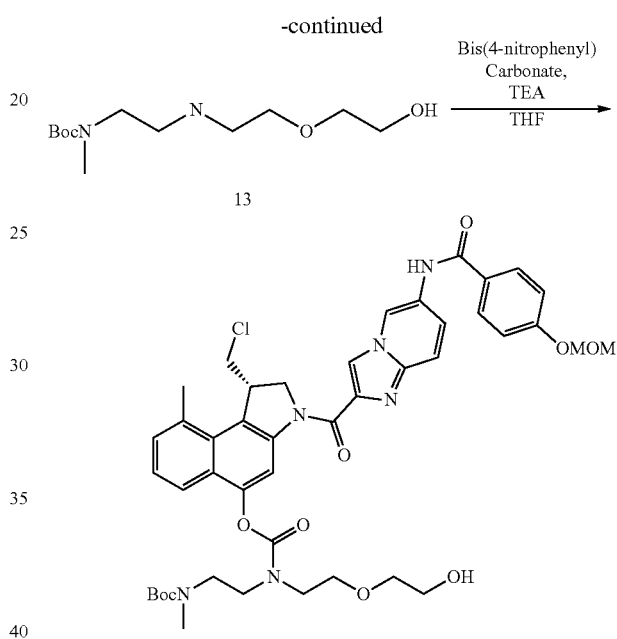

Bis(4-nitrophenyl) carbonate (0.858 g, 2 eq) and trimethylamine (0.983 mL, 5 eq) were added to a solution of compound 12 (0.805 g, 1 eq) in THF (40 mL) under ice bath. The reaction mixture was stirred 8 hours at room temperature and then compound 13 (1.85 g, 5 eq) was added to the reaction mixture under ice bath. The reaction mixture was stirred overnight at room temperature. After the reaction was complete, the organic solvent was removed under reduced pressure. Then, the organic layer was washed with brine and dried over MgSO$_4$. The residue was purified by column chromatography with methanol/dichloromethane to afford compound 14 (21.7% yield). 1H NMR (600 MHz, DMSO) δ 10.33 (s, 1H), 9.47 (s, 1H), 8.70 (s, 1H), 8.40-8.31 (m, 1H), 7.99 (d, J=8.8 Hz, 2H), 7.74 (d, J=9.6 Hz, 2H), 7.58 (d, J=11.7 Hz, 1H), 7.42 (s, 1H), 7.36 (s, 1H), 7.18 (d, J=8.8 Hz, 2H), 5.30 (s, 2H), 5.16 (t, J=4.2 Hz, 1H), 4.69-4.61 (m, 2H), 4.47 (d, J=2.7 Hz, 1H), 3.83 (d, J=11.8 Hz, 1H), 3.80-3.64 (m, 3H), 3.64-3.60 (m, 1H), 3.60-3.51 (m, 4H), 3.52-3.43 (m, 3H), 3.41 (s, 4H), 3.33 (s, 1H), 2.96-2.92 (m, 1H), 2.88-2.81 (m, 3H), 2.81-2.73 (m, 2H), 1.47-1.21 (m, 9H). LC-MS(ESI): m/z Calcd for [C$_{44}$H$_{51}$ClN$_6$O$_{10}$] 859.36 [M+1]$^+$, found 859.7 [M+1]$^+$.

Synthesis of Compound 15
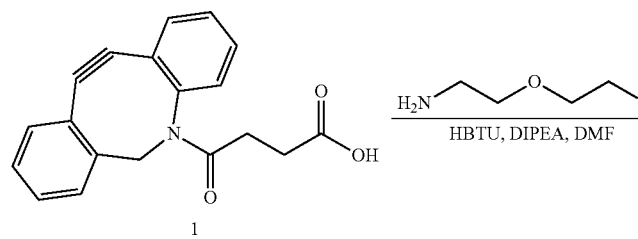
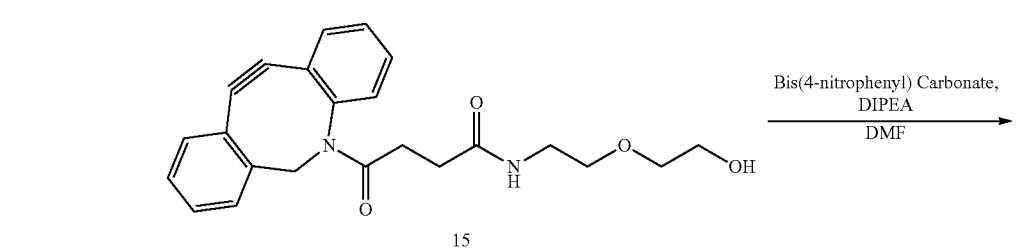
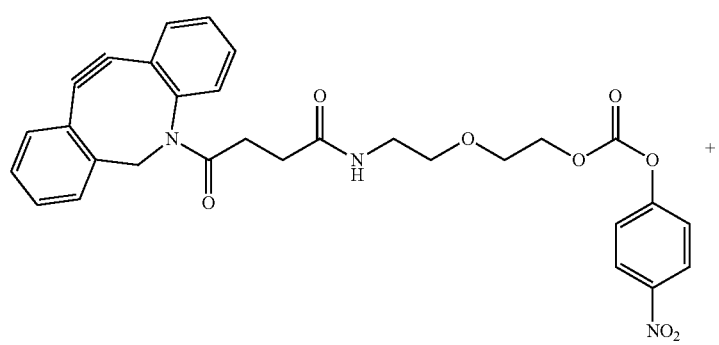
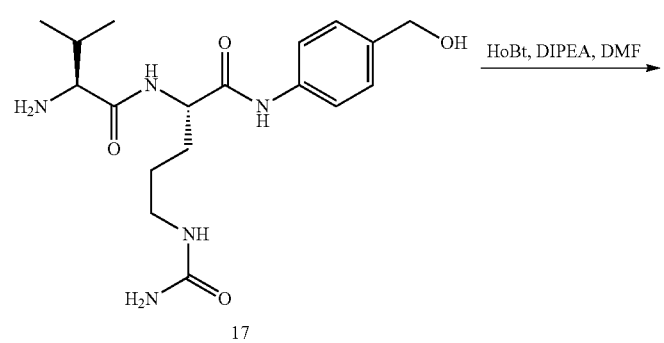
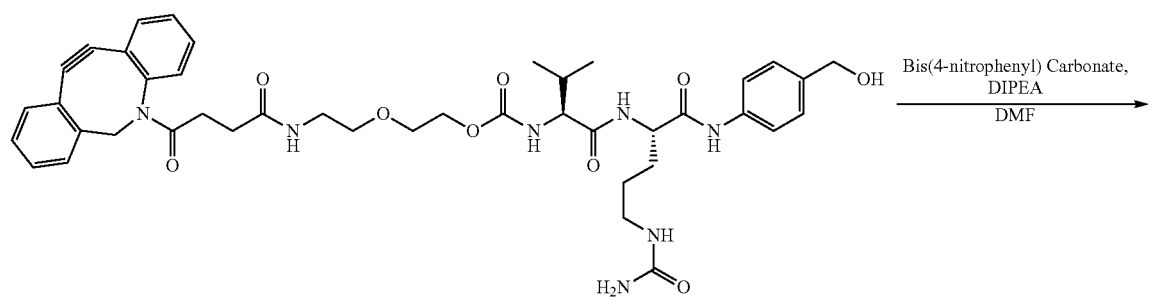

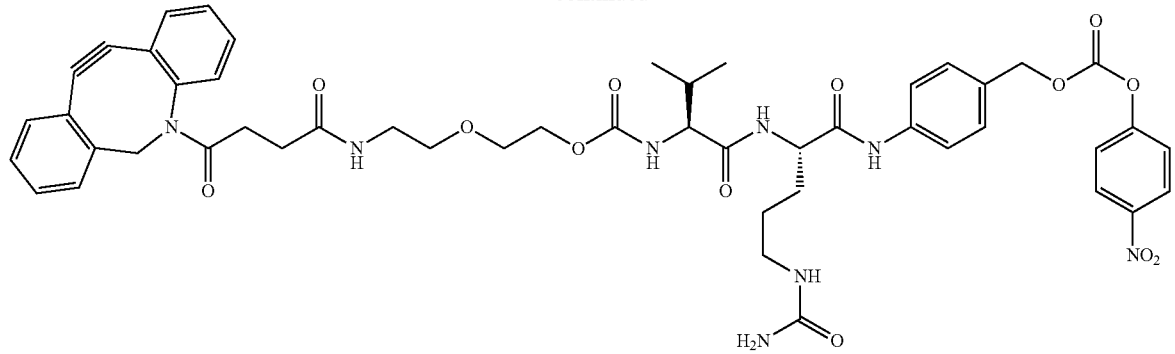

19

DIPEA (0.34 mL, 2 eq) was added to a mixture of compound 1 (0.3 g, 1 eq), HBTU (0.56 g, 1.5 eq), 2-(2-aminoethoxy)ethan-1-ol (0.12 g, 1.2 eq) in DMF (4 mL) under ice bath. The reaction mixture was stirred overnight at room temperature. After the reaction was complete, the reaction mixture was extracted with ethyl acetate and water. Then, the organic layer was washed with brine and dried over $MgSO_4$. The residue was purified by column chromatography with methanol/dichloromethane to afford compound 15 (70% yield). 1H NMR (600 MHz, MeOD) δ 7.55 (d, J=7.4 Hz, 1H), 7.51-7.47 (m, 1H), 7.38-7.33 (m, 3H), 7.24 (dtd, J=22.1, 7.5, 1.2 Hz, 2H), 7.14 (dd, J=7.5, 1.4 Hz, 1H), 5.02 (t, J=10.9 Hz, 1H), 3.66-3.56 (m, 2H), 3.56-3.50 (m, 2H), 3.39-3.36 (m, 2H), 3.36-3.28 (m, 2H), 3.16-3.11 (m, 2H), 2.59 (dt, J=16.4, 7.6 Hz, 1H), 2.25 (dt, J=15.1, 7.5 Hz, 1H), 2.10-2.01 (m, 1H), 1.90-1.82 (m, 1H). LC-MS (ESI): m/z Calcd for $[C_{23}H_{24}N_2O_4]$ 392.45 $[M+1]^+$, found 393.39 $[M+1]^+$.

Synthesis of Compound 16

Bis(4-nitrophenyl) carbonate (0.47 g, 3 eq) and DIPEA (0.2 mL, 3 eq) were added to a solution of compound 15 (0.2 g, 1 eq) in DMF/$CH_2Cl_2$ (6/2 mL) under inert atmosphere. The reaction mixture was stirred overnight at room temperature. After the reaction was complete, the reaction mixture was extracted with ethyl acetate and water. Then, the organic layer was washed with brine and dried over $MgSO_4$. The organic solvent was combined and removed under reduced pressure. The residue was purified by column chromatography with methanol/dichloromethane to afford compound 16 (70% yield). 1H NMR (600 MHz, CDCl3) δ 8.30-8.27 (m, 2H), 7.70 (d, J=7.5 Hz, 1H), 7.53-7.50 (m, 1H), 7.44-7.38 (m, 5H), 7.37 (dd, J=7.5, 1.4 Hz, 1H), 7.32 (td, J=7.5, 0.8 Hz, 1H), 7.27 (d, J=1.2 Hz, 1H), 5.17 (d, J=13.9 Hz, 1H), 4.43 (t, J=4.6 Hz, 2H), 3.81-3.72 (m, 2H), 3.69 (d, J=13.9 Hz, 1H), 3.57-3.44 (m, 2H), 3.43-3.32 (m, 2H), 2.83 (ddd, J=16.9, 8.6, 5.9 Hz, 1H), 2.45 (ddd, J=14.7, 8.6, 5.8 Hz, 1H), 2.21 (dt, J=15.2, 6.1 Hz, 1H), 1.97 (dt, J=17.0, 6.1 Hz, 1H). LC-MS(ESI): m/z Calcd for $[C_{30}H_{27}N_3O_8]$ 557.55 $[M+1]^+$, found 558.58 $[M+1]^+$.

Synthesis of Compound 18

DIPEA (0.134 mL, 2.2 eq) was added to a mixture of compound 16 (0.2 g, 1 eq), compound 17 (0.2 g, 1.5 eq), and HOBt (0.11 g, 2.2 eq) in DMF (5 mL). The reaction mixture was stirred overnight at room temperature. After the reaction was complete, the reaction mixture was extracted with ethyl acetate and water. Then, the organic layer was washed with brine and dried over $MgSO_4$. The organic solvent was combined and removed under reduced pressure. The residue was purified by column chromatography with methanol/dichloromethane to afford compound 18 (36% yield).

Synthesis of Compound 19

Bis(4-nitrophenyl) carbonate (0.08 g, 3 eq) and DIPEA (0.043 mL, 3 eq) were added to a solution of compound 18 (0.05 g, 1 eq) in DMF (3 mL) under inert atmosphere. The reaction mixture was stirred overnight at room temperature. After the reaction was complete, the reaction mixture was extracted with ethyl acetate and water. Then, the organic layer was washed with brine and dried over $MgSO_4$. The organic solvent was combined and removed under reduced pressure. The residue was purified by column chromatography with methanol/dichloromethane to afford compound 19 (33% yield).

Synthesis of DBCO-VC-Seco D UBA (Compound 20)

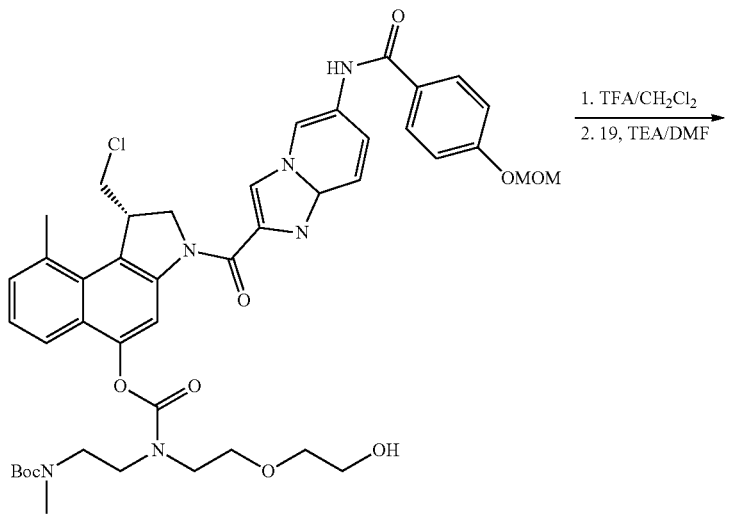

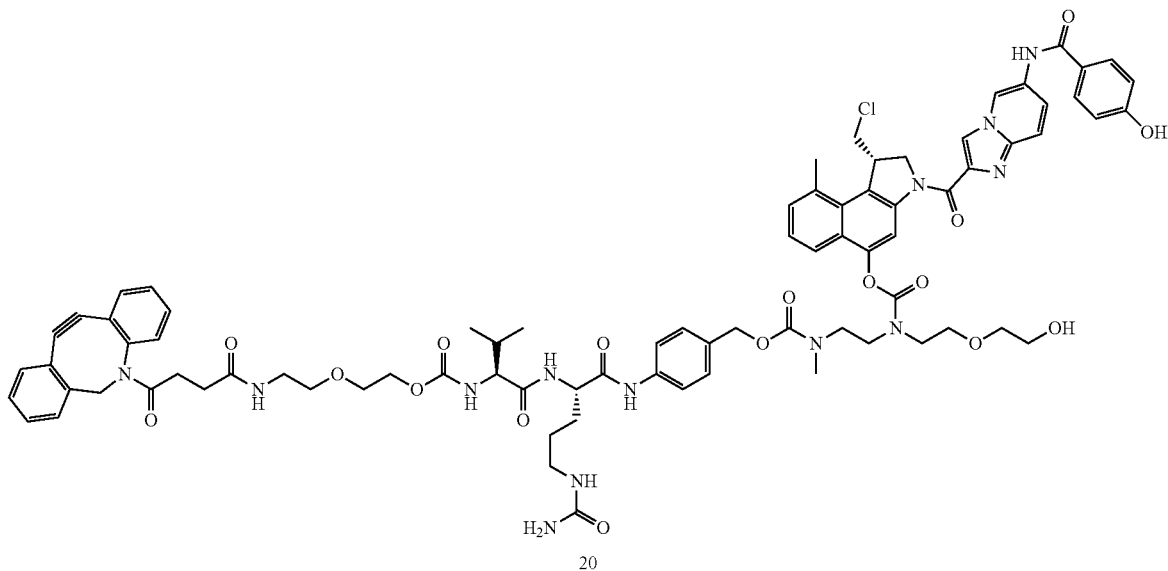

TFA (11.2 mL, 3 eq) was added to a solution of compound 14 (0.263 g, 1 eq) in CH$_2$Cl$_2$ (11.2 mL) under ice bath. The reaction mixture was stirred 1 hour at room temperature. After the reaction was complete, the organic solvent was removed under reduced pressure. The residue was dissolved in DMF (7.6 mL). Compound 19 (0.324 g, 1.1 eq) and TEA (0.21 mL, 5 eq) were added to the mixture under ice bath. The reaction mixture was stirred overnight at room temperature. After the reaction was complete, the organic solvent was removed under reduced pressure. The residue was extracted with dichloromethane and water. Then, the organic layer was washed with brine and dried over MgSO$_4$. The residue was purified by column chromatography with methanol/dichloromethane to afford compound 20 (DBCO-vc-seco DUBA) (55.2% yield).

Example 7 Synthesis of DBCO-DTPA (Compound 22)

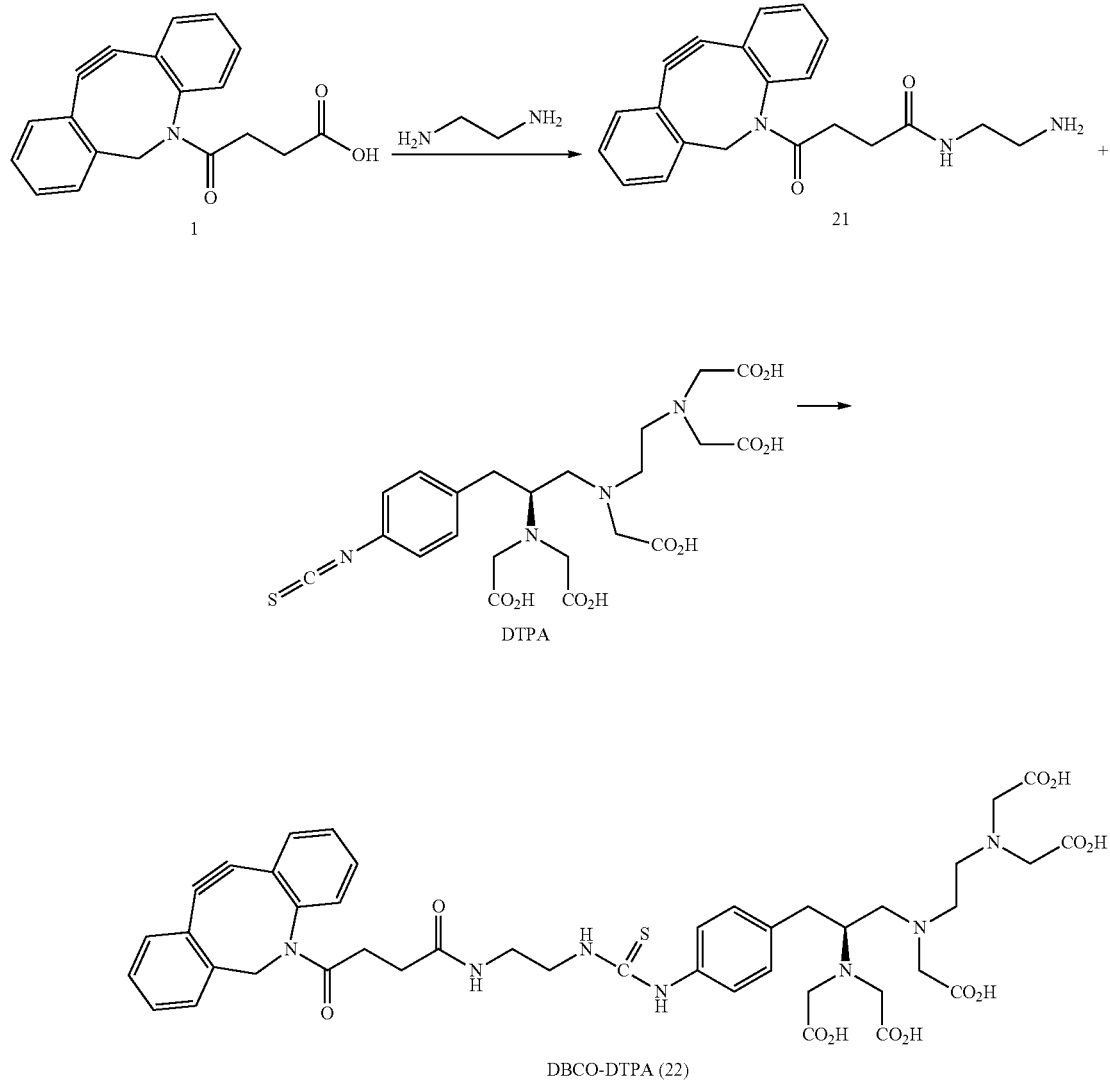

Synthesis of Compound 21

HOSu (226 mg, 3 eq) was added to a mixture of DBCO-CO$_2$H (1) (200 mg, 1 eq), EDC (376 mg, 3 eq) in dichloromethane (5 mL). The mixture was stirred for 2 hours at room temperature. After the reaction was completed, the reaction mixture was extracted with DCM and water. Then, the organic layer was washed with brine and dried over MgSO$_4$. The organic solvent was removed under reduced pressure to afford pale yellow liquid.

The yellow liquid was added dropwise to a solution of ethylenediamine in dichloromethane for 20 minutes. The mixture was stirred for overnight at room temperature. After the reaction was completed, the reaction mixture was extracted with DCM and NaHCO$_{3(aq.)}$. Then, the organic layer was washed with brine and dried over MgSO$_4$. The organic solvent was removed under reduced pressure. The residue was purified by column chromatography with methanol/dichloromethane to afford a yellow oil (yield: 58.9%). $^1$H NMR (600 MHz, MeOD) δ 7.63 (d, J=7.4 Hz, 1H), 7.61-7.56 (m, 1H), 7.47-7.41 (m, 3H), 7.32 (dtd, J=23.9, 7.5, 1.2 Hz, 2H), 7.23 (dd, J=7.5, 1.3 Hz, 1H), 5.08 (d, J=14.0 Hz, 1H), 3.63 (d, J=14.0 Hz, 1H), 3.14 (dtd, J=19.7, 13.5, 6.2 Hz, 2H), 2.74 (ddd, J=16.6, 8.0, 6.8 Hz, 1H), 2.68-2.54 (m, 2H), 2.31 (ddd, J=14.8, 8.0, 6.6 Hz, 1H), 2.16 (dt, J=15.2, 6.5 Hz, 1H), 1.95 (dt, J=16.7, 6.4 Hz, 1H). LC-MS (ESI): m/z Calcd for [C$_{21}$H$_{21}$N$_3$O$_2$] 348.16 [M+1]$^+$, found 348.03 [M+1]$^+$.

Synthesis of DBCO-DTPA (Compound 22)

Commercial DTPA (26 mg, 1.1 eq) was added to a solution of compound 21 (13 mg, 1 eq.) in H$_2$O:DMF 3:1 (3 mL). The mixture was stirred for overnight at room temperature. After the reaction was completed, the reaction mixture was extracted with dichloromethane and water. Then, the organic layer was washed with brine and dried over MgSO$_4$. The organic solvent was removed under reduced pressure to afford a yellow solid DBCO-DTPA (20 mg). LC-MS (ESI): m/z Calcd for [C$_{43}$H$_{49}$N$_7$O$_{12}$S] 888.32 [M+1]$^+$, found 888.47 [M+1]$^+$.

Example 8 Synthesis of DBCO-PEG3-VC-Exatecan (Compound 25)
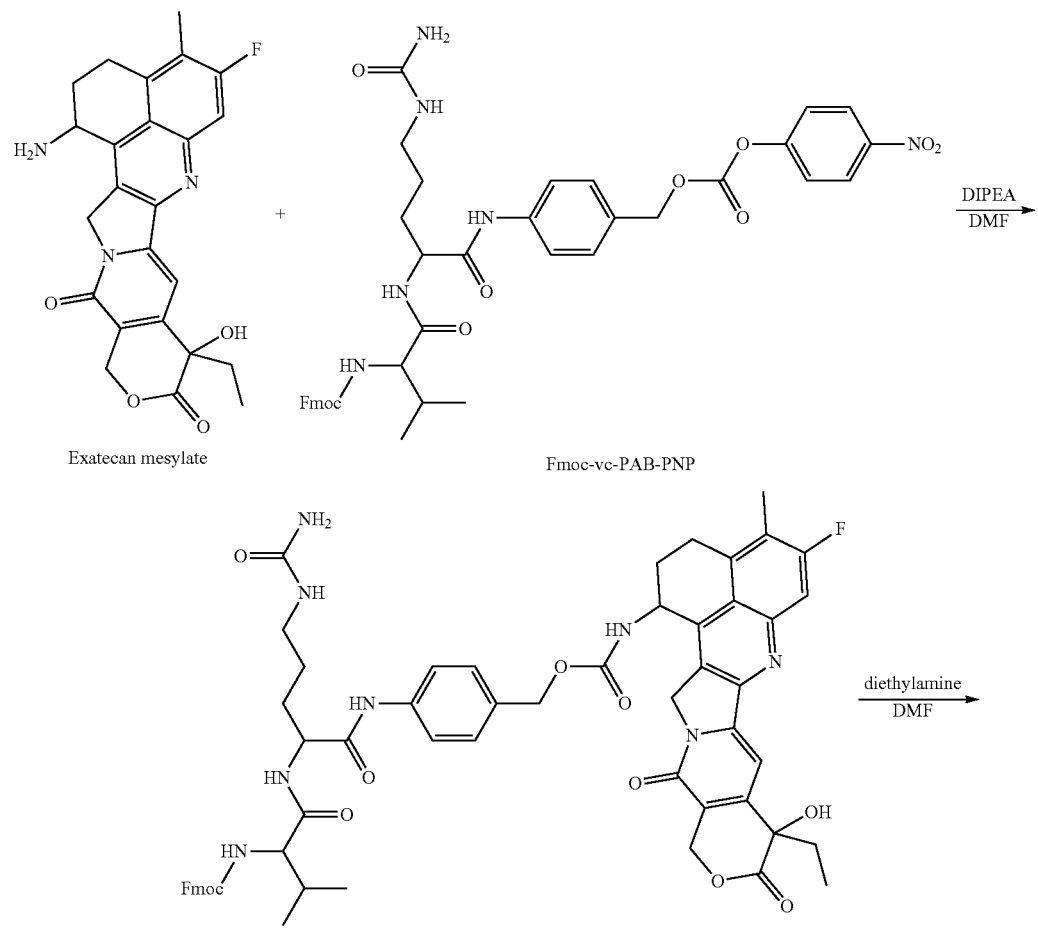
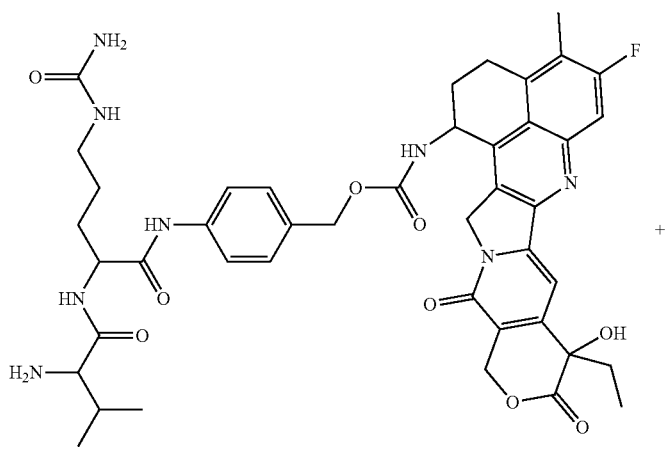

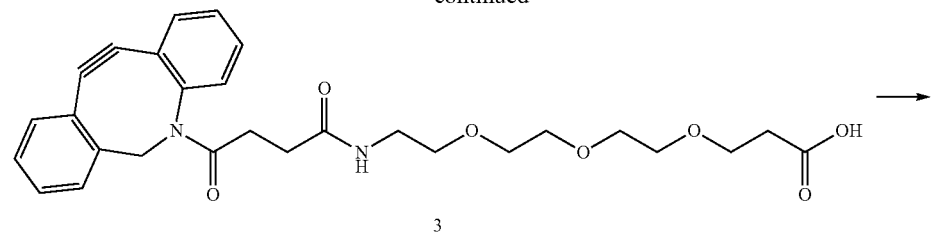

3

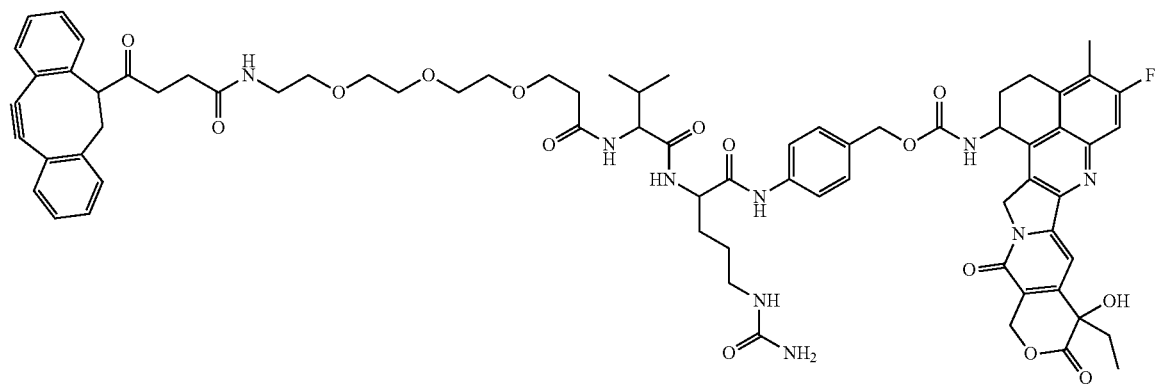

DBCO-PEG3-vc-exatecan (25)

Synthesis of compound 23

DIPEA (0.082 mL, 2.5 eq) was added to a mixture of exatecan mesylate (0.11 g, 1.1 eq) and Fmoc-vc-PAB-PNP (0.144 g, 1 eq) in DMF (3 mL). The reaction mixture was stirred for overnight at room temperature. After the reaction was completed, the DMF removed under reduced pressure. The residue was washed with diethyl ether and dichloromethane to afford 0.2 g grey solid (compound 23) without further purification.

Synthesis of Compound 24

Diethylamine (0.082 mL, 2.5 eq) was added to a solution of compound 23 in DMF (3 mL). The reaction mixture was stirred for overnight at room temperature. After the reaction was completed, the DMF removed under reduced pressure. The residue was washed with diethyl ether and dichloromethane to afford 0.14 g black solid (compound 24) without further purification. $^1$H NMR (600 MHz, DMSO) δ 10.18 (s, 1H), 8.45 (s, 1H), 8.08 (d, J=9.0 Hz, 1H), 7.96 (s, 1H), 7.79 (d, J=10.8 Hz, 1H), 7.61 (d, J=8.4 Hz, 2H), 7.38 (d, J=8.4 Hz, 2H), 7.32 (s, 1H), 6.55 (s, 1H), 6.03 (t, J=5.6 Hz, 1H), 5.46 (s, 2H), 5.45 (s, 2H), 5.34-5.22 (m, 3H), 5.14-5.04 (m, 2H), 4.54-4.45 (m, 1H), 4.13 (dt, J=6.9, 6.2 Hz, 1H), 3.28-3.21 (m, 1H), 3.19-3.15 (m, 1H), 3.15-3.07 (m, 1H), 3.06-3.00 (m, 1H), 2.98-2.93 (m, 1H), 2.39-2.35 (m, 3H), 2.25-2.18 (m, 1H), 2.18-2.11 (m, 1H), 2.04-1.98 (m, 1H), 1.93-1.83 (m, 2H), 1.74-1.67 (m, 1H), 1.64-1.56 (m, 1H), 1.50-1.42 (m, 1H), 1.42-1.34 (m, 1H), 0.96-0.91 (m, 3H), 0.91-0.85 (m, 6H). LC-MS (ESI): m/z Calcd for [$C_{43}H_{49}FN_8O_9$] 841.36 [M+1]$^+$, found 841.34 [M+1]$^+$.

Synthesis of Compound 25

DIPEA (13.7 uL, 3 eq) was added to a mixture of compound 3 (13 mg, 1 eq), compound 24 (33 mg, 1.5 eq) and HATU (30 mg, 3 eq) in DCM:DMF 2:1 (3 mL). The mixture was stirred for 2 hours at room temperature. After the reaction was completed, the reaction mixture was extracted with DCM and water. Then, the organic layer was washed with brine and dried over MgSO$_4$. The organic solvent was removed under reduced pressure. The residue was purified by column chromatography with methanol/dichloromethane to afford a pale yellow solid compound 25 (66.7% yield). $^1$H NMR (600 MHz, DMSO) δ 10.00 (s, 1H), 8.69 (s, 1H), 8.47 (d, J=8.9 Hz, 1H), 8.14 (d, J=7.7 Hz, 1H), 8.07 (t, J=9.0 Hz, 1H), 7.88 (d, J=8.8 Hz, 1H), 7.82-7.74 (m, 2H), 7.68 (dd, J=7.6, 1.0 Hz, 1H), 7.64-7.60 (m, 2H), 7.52-7.43 (m, 3H), 7.37 (d, J=8.5 Hz, 2H), 7.35-7.27 (m, 2H), 6.54 (s, 1H), 5.99 (t, J=7.1 Hz, 1H), 5.45 (s, 1H), 5.43 (s, 2H), 5.32-5.27 (m, 2H), 5.10-5.06 (m, 1H), 5.02 (d, J=14.1 Hz, 1H), 4.38 (dd, J=13.0, 7.7 Hz, 1H), 4.26-4.20 (m, 1H), 3.64-3.56 (m, 3H), 3.51-3.41 (m, 7H), 3.31-3.19 (m, 4H), 3.18-2.91 (m, 6H), 2.62 (dt, J=3.6, 1.8 Hz, 1H), 2.61-2.54 (m, 1H), 2.40-2.33 (m, 4H), 2.27-2.11 (m, 3H), 2.03-1.92 (m, 2H), 1.91-1.81 (m, 2H), 1.80-1.65 (m, 3H), 1.63-1.59 (m, 1H), 1.59-1.54 (m, 1H), 1.52-1.40 (m, 2H), 1.38-1.32 (m, 1H), 0.91-0.79 (m, 9H). LC-MS(ESI): m/z Calcd for [$C_{71}H_{79}FN_{10}O_{15}$] 1331.57 [M+1]$^+$, found 1331.72 [M+1]$^+$.

Example 9 Synthesis of
DBCO-PEG3-GGFG-Exatecan (Compound 29)
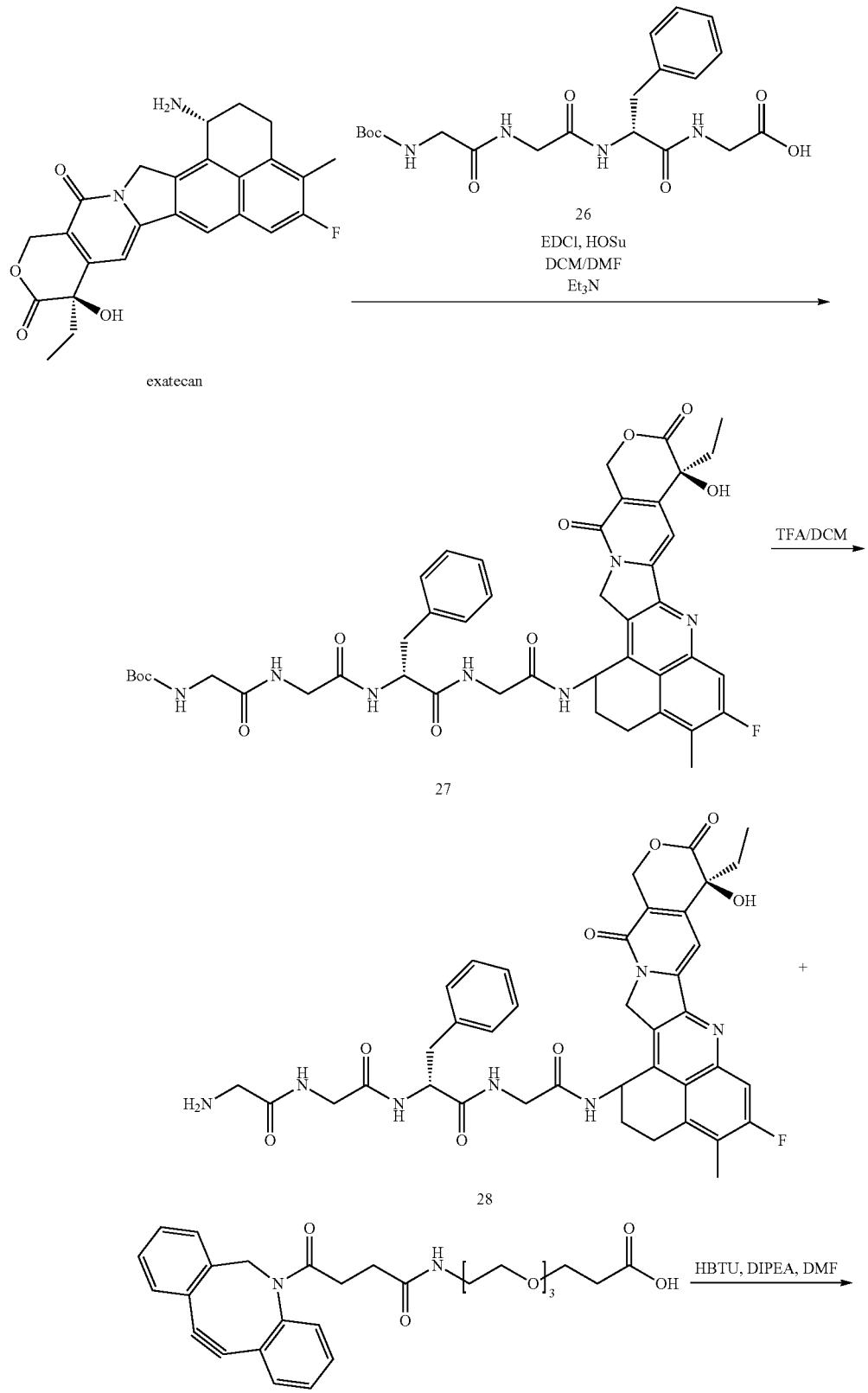

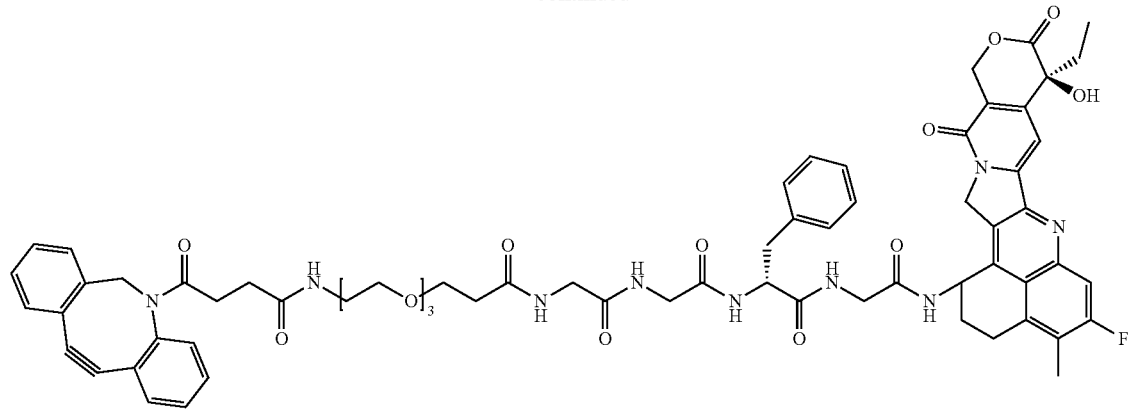

29

Synthesis of Compound 27

Commercial Boc-GGFG-OH (compound 26) (415 mg, 1 eq) was added to a mixture of EDCI (273 mg, 1.5 eq) and HOSu (164 mg, 1.5 eq) in dichloromethane (18 mL). The mixture was stirred for 3.5 hours at room temperature. The reaction mixture was added dropwise to a mixture DMF solution of exatecan mesylate (343 mg, 0.83 eq) and triethylamine (0.2 mL, 1.5 eq). The reaction mixture was stirred for overnight at room temperature. After the reaction was completed, the organic solvent was removed under reduced pressure. The residue was purified by column chromatography with methanol/dichloromethane to afford a pale yellow solid compound 27 (507 mg, 63% yield). LC-MS(ESI): m/z Calcd for $[C_{44}H_{48}FN_7O_{10}]$ 853.91 $[M+1]^+$, found 854.35 $[M+1]^+$. 875.91$[M+Na]^+$, found 875.52$[M+Na]^+$.

Synthesis of Compound 28

Trifluoroacetic acid (4 mL) was added to a solution of compound 27 (507 mg, 1 eq) in dichloromethane (4 mL). The mixture was stirred for 3 hours at room temperature. After the reaction was completed, the organic solvent was removed under reduced pressure. The residue was wash with dichloromethane to afford a yellow solid compound 28 (378 mg, 85% yield). LC-MS(ESI): m/z Calcd for $[C_{39}H_{40}FN_7O_8]$ 753.79 $[M+1]^+$, found 754.18 $[M+1]^+$.

Synthesis of Compound 29

DIPEA (0.18 mL, 20 eq) was added to a solution of Compound 28 (40 mg, 1 eq) in DMF (1 mL). The reaction mixture was stirred for 15 mins under ice bath. The reaction mixture was added dropwise to a mixture DMF solution (1 mL) of compound 3 (48 mg, 1.2 eq) and HBTU (30 mg, 1.5 eq). The mixture was stirred for 2 hours at room temperature. After the reaction was completed, the organic solvent was removed under reduced pressure. The residue was purified by column chromatography with methanol/dichloromethane to afford a pale yellow solid compound 29 (44 mg, 67% yield). LC-MS(ESI): m/z Calcd for $[C_{67}H_{70}FN_9O_{14}]$ 1244.34 $[M+1]^+$, found 1244.56 $[M+1]^+$. 1266.34$[M+Na]^+$, found 1266.83$[M+Na]^+$.

Example 10 Synthesis of DBCO-PEG12-GGFG-Exatecan (Compound 31)

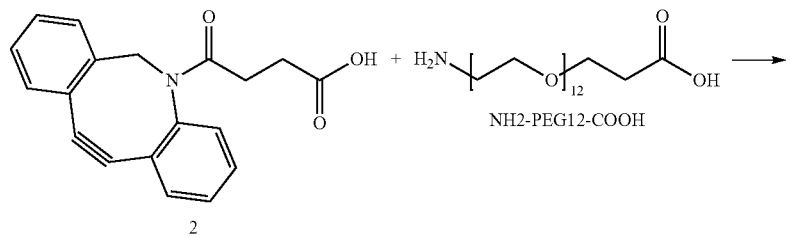

2     NH2-PEG12-COOH

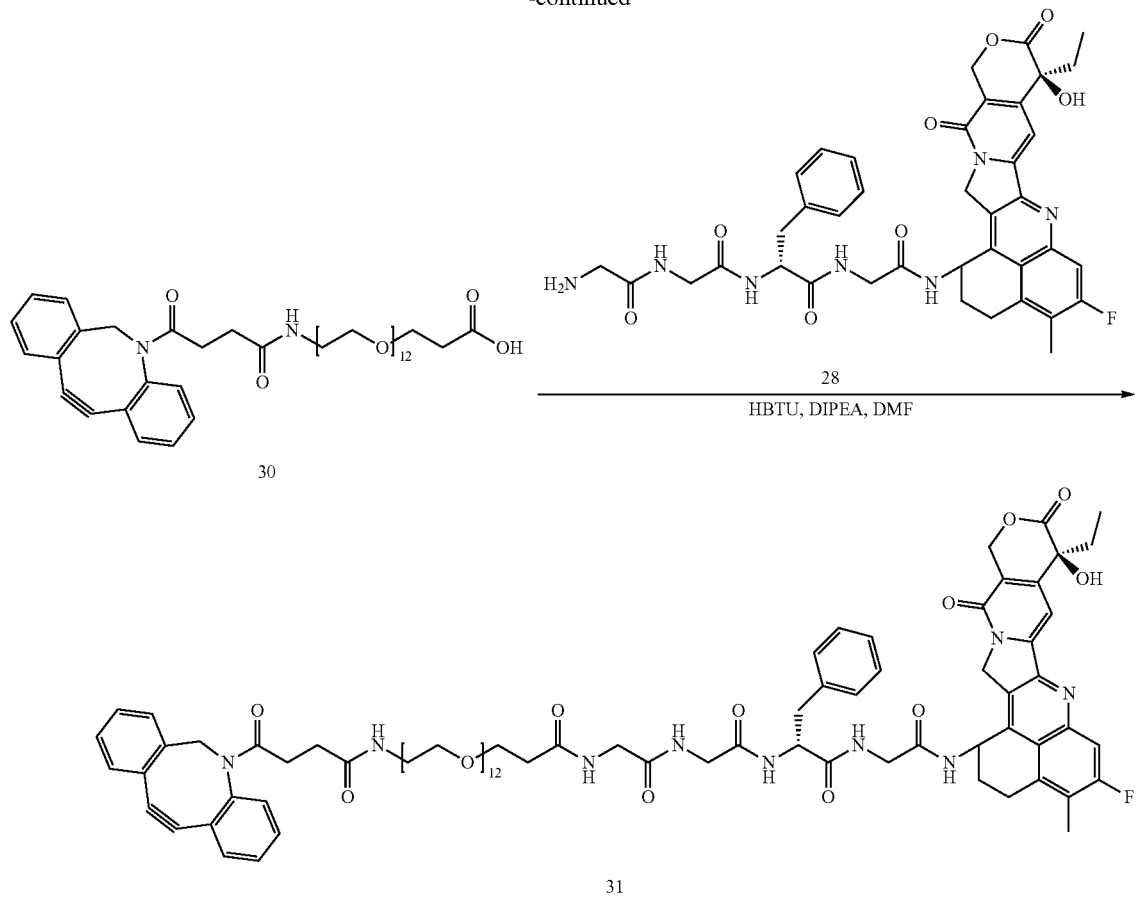

Synthesis of Compound 30

DIPEA (0.7 mL, 2 eq) was added to a mixture of compound 2 and NH$_2$-PEG12-COOH (1217 mg, 1.0 eq) in dichloromethane/DMF (8 mL/8 mL). The reaction mixture was stirred overnight at room temperature. After the reaction was completed, organic solvent was removed under reduced pressure. The residue was purified by column chromatography with methanol/dichloromethane to afford a viscous liquid DBCO-PEG12-GGFG-exatecan (compound 31) (401 mg, 23% yield). LC-MS(ESI): m/z Calcd for [C$_{46}$H$_{68}$N$_2$O$_{16}$] 905.05 [M]$^+$, found 905.53 [M]$^+$.

Synthesis of Compound 31

DIPEA (0.14 mL, 20 eq) was added to a mixture of compound 28 (30 mg, 1 eq) in DMF (1 mL). The reaction mixture was stirred for 15 mins under ice bath. The reaction mixture was added dropwise to a mixture solution (1 mL) of compound 30 (43 mg, 1.2 eq) and HBTU (23 mg, 1.5 eq) in DMF. The reaction mixture was stirred for 2 hours at room temperature. After the reaction was completed, organic solvent was removed under reduced pressure. The residue was purified by column chromatography with methanol/dichloromethane to afford a yellow solid compound 31 (17 mg, 26% yield). LC-MS(ESI): m/z Calcd for [C$_{85}$H$_{106}$FN$_9$O$_{23}$] 1640.82 [M+1]$^+$, found 1641.07 [M+1]$^+$.

Example 11 Synthesis of
DBCO-PEG3-GGFG-DXd2 (Compound 36)
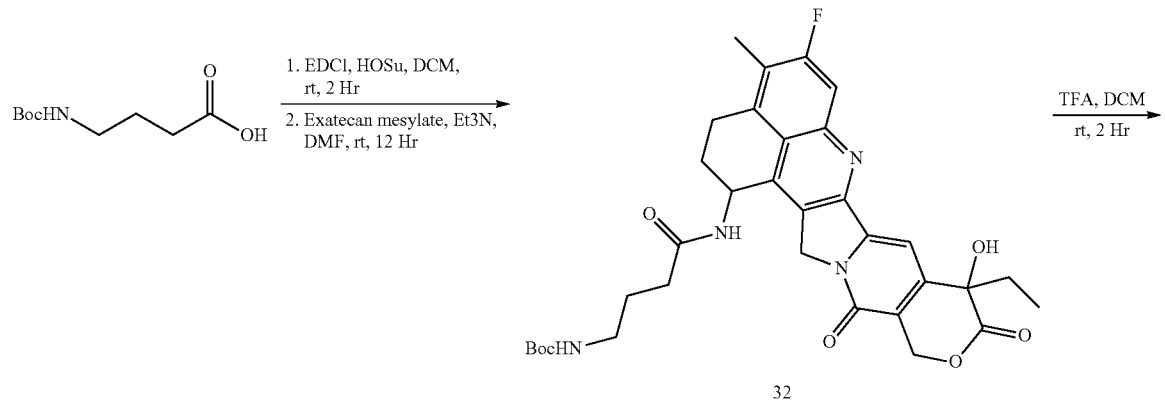
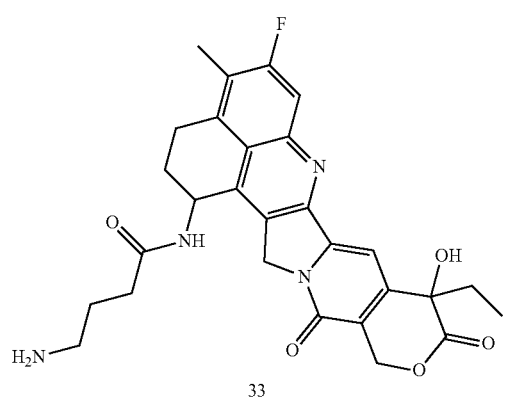
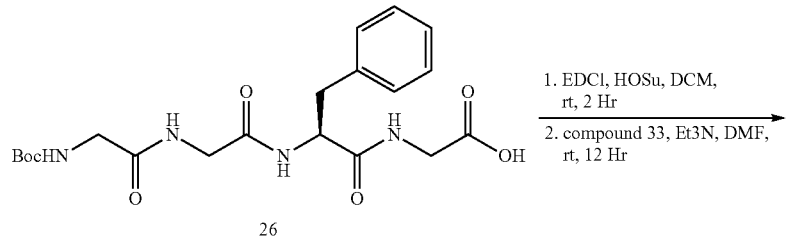
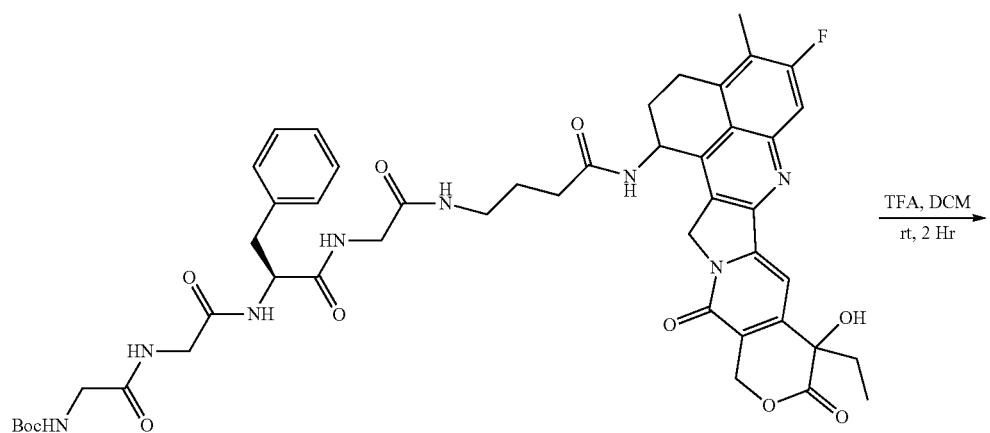

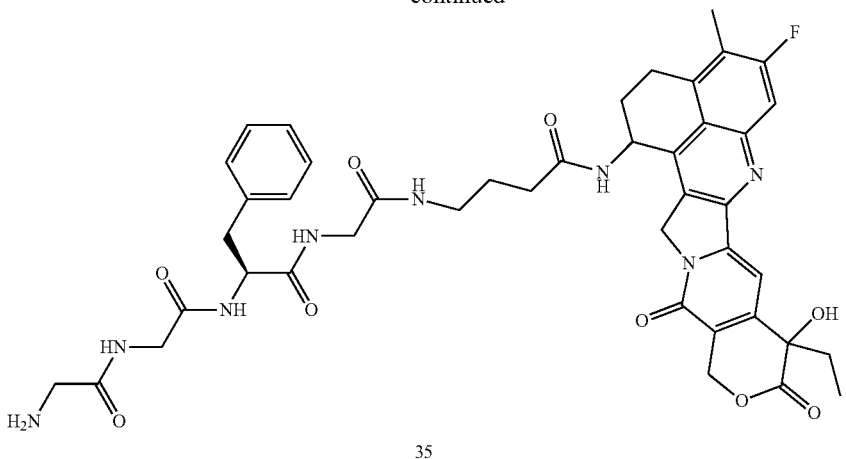

35

Synthesis of Compound 32

HOSu (170 mg, 1.5 eq) was added to a mixture of N-(tert-butoxycarbonyl)-4-aminobutanoic acid (200 mg, 1.0 eq) and EDCI (283 mg, 1.5 eq) in DCM (5 mL). The reaction mixture was stirred for 2 hours at room temperature under $N_2$ atmosphere. After the reaction was completed, the reaction mixture was extracted with dichloromethane and water. The organic layer was washed with brine and dried over $MgSO_4$. The organic solvent was removed under reduced pressure. The residue was added to a mixture solution of exatecan mesylate (434 mg, 0.83 eq) and $Et_3N$ (0.21 mL, 1.5 eq) in DMF (5 mL). The reaction mixture was stirred for 12 hours at room temperature. The organic solvent was removed under reduced pressure. The residue was purified by column chromatography to afford a yellow solid compound 32 (402 mg, 79% yield). LC-MS (ESI): m/z calcd for $C_{33}H_{37}FN_4O_7$ $[M+H]^+$: 621.26, found: 621.01.

Synthesis of Compound 33

Compound 32 was added to a mixture solution of DCM/TFA=1/1 (9.5 mL/9.5 mL). The reaction mixture was stirred for 2 hours at room temperature under $N_2$ atmosphere. After the reaction was completed, the organic solvent was removed under reduced pressure. The residue was purified by column chromatography (DCM/MeOH) to afford a yellow solid compound 33 (23 mg, 69% yield). LC-MS (ESI): m/z calcd for $C_{28}H_{29}FN_4O_5$ $[M+H]^+$; 521.21, found: 521.09. $^1H$ NMR (600 MHz, DMSO) δ 8.53 (d, J=8.7 Hz, 1H), 7.82 (d, J=10.8 Hz, 1H), 7.32 (s, 3H), 6.56 (s, 1H), 5.65-5.53 (m, 1H), 5.43 (s, 2H), 5.25 (d, J=18.7 Hz, 1H), 5.15 (d, J=18.7 Hz, 1H), 3.17 (t, J=6.0 Hz, 2H), 2.81 (t, J=7.6 Hz, 2H), 2.42-2.37 (m, 3H), 2.26 (t, J=7.1 Hz, 2H), 2.14 (d, J=5.3 Hz, 2H), 1.99-1.70 (m, 4H), 0.87 (t, J=7.3 Hz, 3H).

Synthesis of Compound 34

Compound 26 (252 mg, 1.3 eq) was added to a mixture of EDCI (104 mg, 1.5 eq) and HOSu (77 mg, 1.5 eq) in DCM (9 mL). The reaction mixture was stirred for 2 hours at room temperature under $N_2$ atmosphere. After the reaction was completed, the reaction mixture was extracted with dichloromethane and water. The organic layer was washed with brine and dried over $MgSO_4$. The organic solvent was removed under reduced pressure. The residue was added to the mixture solution of compound 33 (231 mg, 1.0 eq) and $Et_3N$ (0.1 mL, 1.5 eq). The reaction mixture was stirred for 12 hours at room temperature under $N_2$ atmosphere. After the reaction was completed, the organic solvent was removed under reduced pressure. The residue was purified by column chromatography (DCM/MeOH) to afford a yellow solid compound 34 (153 mg, 28% yield). LC-MS (ESI): m/z calcd for $C_{48}H_{55}FN_8O_{11}$ $[M+H]^+$: 939.4, found: 939.68.

Synthesis of Compound 35

Compound 34 was added to a mixture solution of DCM/TFA=1/1 (3 mL/3 mL). The reaction mixture was stirred for 2 hours at room temperature under $N_2$ atmosphere. After the reaction was completed, the organic solvent was removed under reduced pressure. The residue was purified by column chromatography (DCM/MeOH) to afford a yellow solid compound 35 (90 mg, 65% yield). LC-MS (ESI): m/z calcd for $C_{43}H_{47}FN_8O_9$ $[M+H]^+$; 839.35, found: 839.22.

Synthesis of DBCO-PEG3-GGFG-DXd2 (Compound 36)

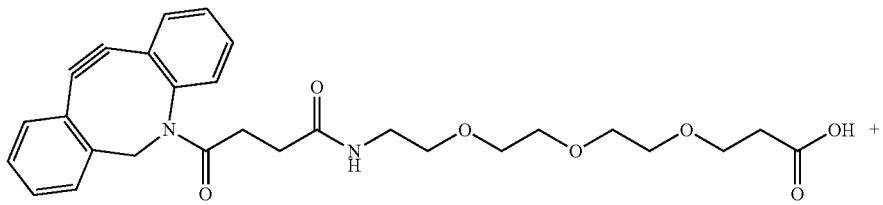

3

-continued

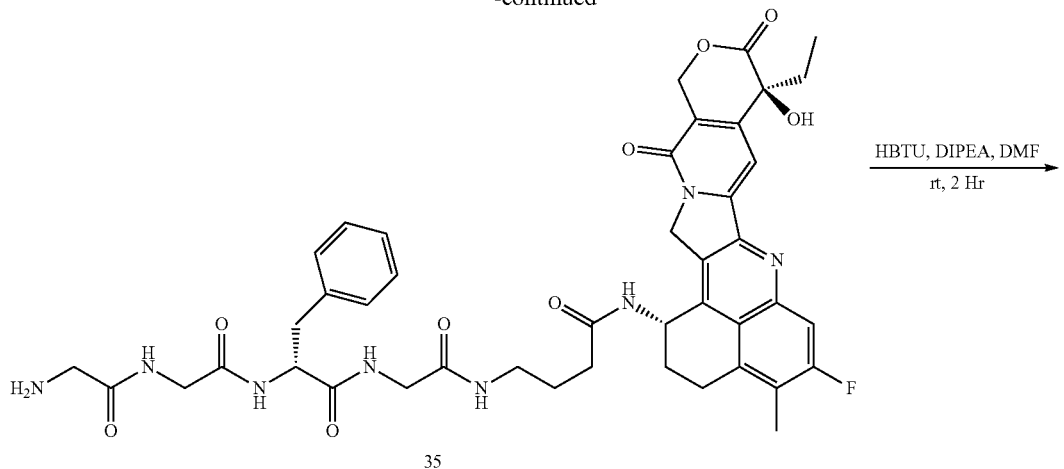

35

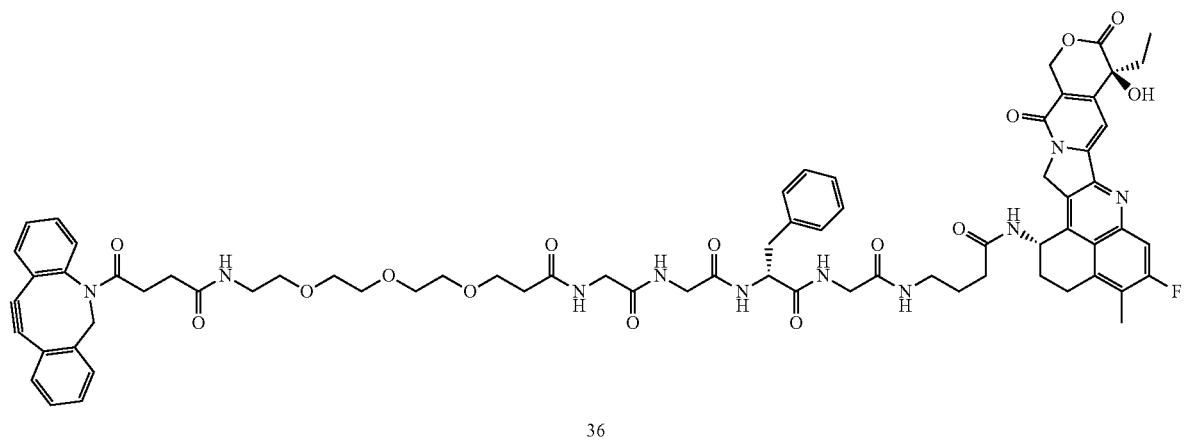

36

Compound 35 (20 mg, 1 eq) was added to a mixture of compound 3 (13.3 mg, 1.1 eq), DIPEA (0.083 mL, 20 eq) and HBTU (13.6 mg, 1.5 eq) in DMF (2 mL). The reaction mixture was stirred for 1.5 hours at room temperature under $N_2$ atmosphere. After the reaction was completed, the organic solvent was removed under reduced pressure. The residue was purified by column chromatography (DCM/MeOH) to afford a yellow solid compound 36 (18 mg, 58% yield). LC-MS (ESI): m/z calcd for $C_{71}H_{77}FN_{10}O_{15}$ [M+H]$^+$: 1329.43, found: 1329.69.

Example 12 Synthesis of DBCO-PEG12-GGFG-DXd2 (Compound 37)

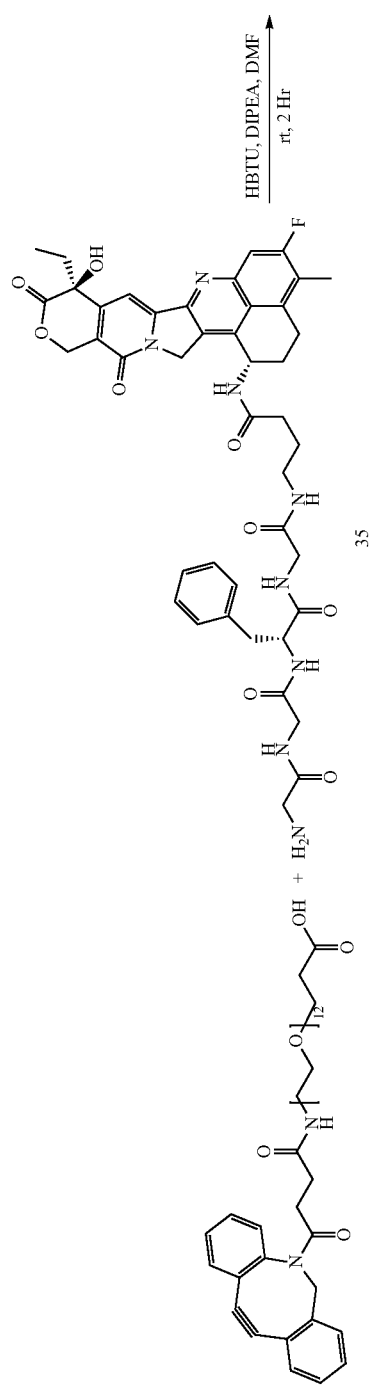
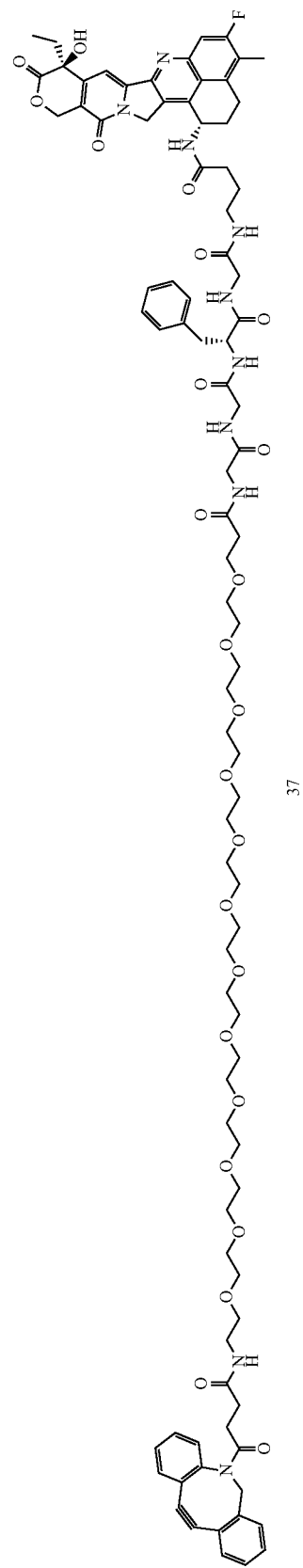

Compound 35 (20 mg, 1 eq) was added to a mixture of compound 30 (19 mg, 0.9 eq), DIPEA (0.083 mL, 20 eq) and HBTU (13.6 mg, 1.5 eq) in DMF (2 mL). The reaction mixture was stirred for 1.5 hours at room temperature under N$_2$ atmosphere. After the reaction was completed, the organic solvent was removed under reduced pressure. The residue was purified by column chromatography (DCM/MeOH) to afford a yellow solid compound 37 (6.4 mg, 17% yield). LC-MS (ESI): m/z calcd for C$_{89}$H$_{113}$FN$_{10}$O$_{24}$ [M+H]$^+$: 1726.9, found: 1726.6.

Example 13 Synthesis of BCN-PEG3-VC-PAB-MMAE (Compound 40)

temperature. After the reaction was completed, the organic solvent was removed under reduced pressure. The residue was purified by column chromatography (DCM/MeOH) to afford a viscous liquid compound 39 (235 mg, 62% yield). LC-MS(ESI): m/z Calcd for [C$_{20}$H$_{31}$NO$_7$] 397.47 [M+1]$^+$, found 397.39 [M+1]$^+$. 420.47[M+Na]$^+$, found 420.07[M+Na]$^+$.

Synthesis of Compound 40

DIPEA (69 ul, 4 eq) was added to a mixture of compound 39 (41 mg, 1 eq), compound 4 (135 mg, 1.2 eq) and HATU (57 mg, 1.5 eq) in DMF (3 mL). The reaction mixture was stirred for 18 hours at room temperature. After the reaction was completed, the organic solvent was removed under

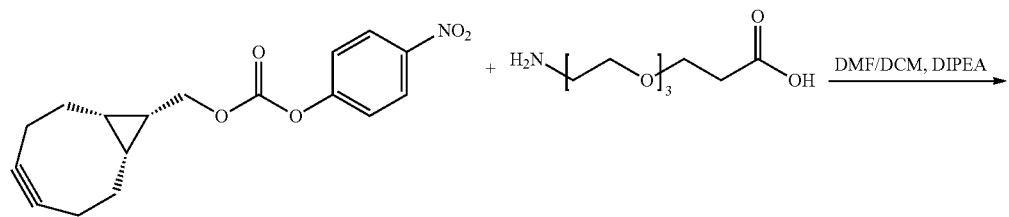

38

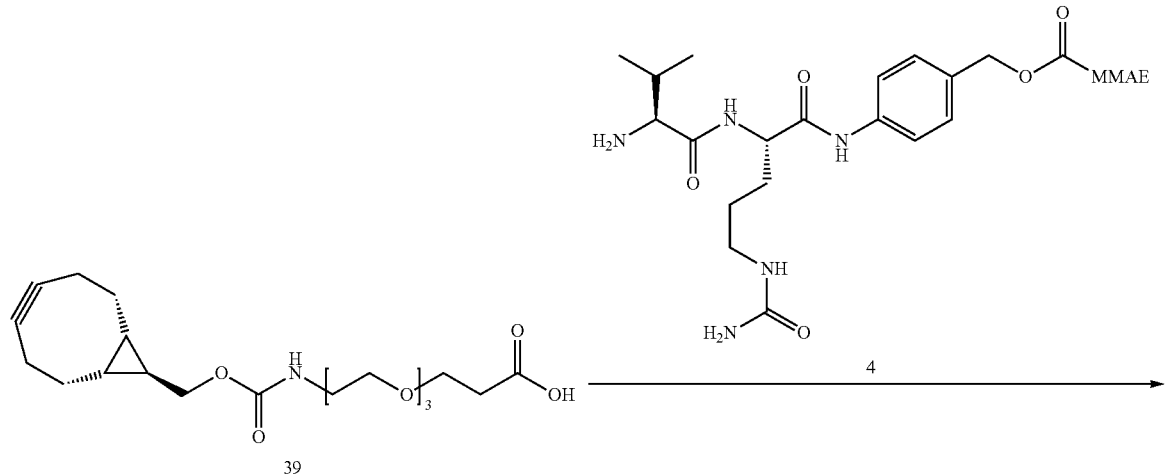

39

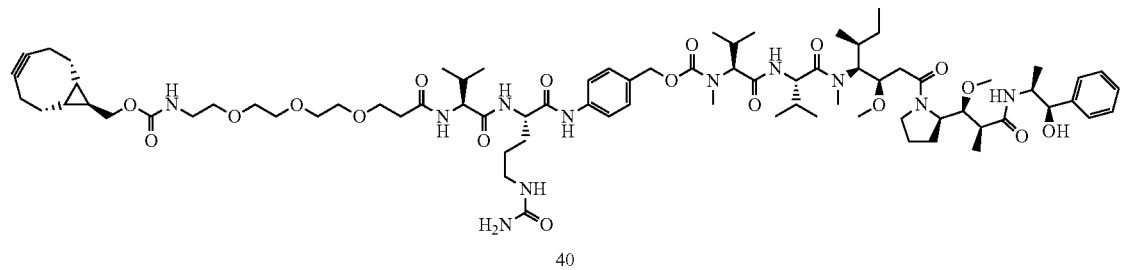

40

Synthesis of Compound 39

DIPEA (0.5 mL, 3 eq) was added to a mixture of commercial compound 38 (300 mg, 1 eq) and NH$_2$-PEG3-COOH (273 mg, 1.3 eq) in dichloromethane/DMF (3 mL/3 mL). The reaction mixture was stirred for 18 hours at room reduced pressure. The residue was purified by column chromatography (DCM/MeOH) to afford a yellow solid compound 40 (41 mg, 27% yield). LC-MS(ESI): m/z Calcd for [C$_{78}$H$_{123}$N$_{11}$O$_{18}$] 1502.90 [M+1]$^+$, found 1503.13 [M+1]$^+$. 1524.90[M+Na]$^+$, found 1525.43[M+Na]$^+$.

Example 14 Synthesis of
BCN-PEG12-GGFG-Exatecan (Compound 42)

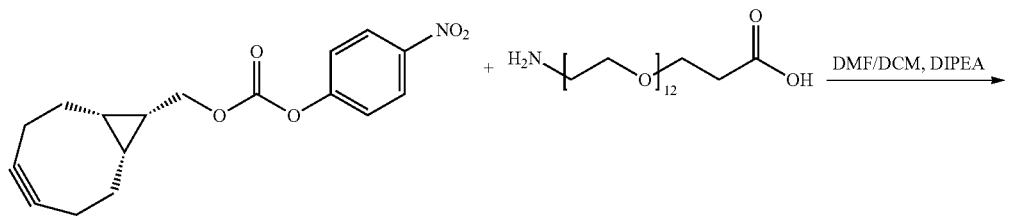

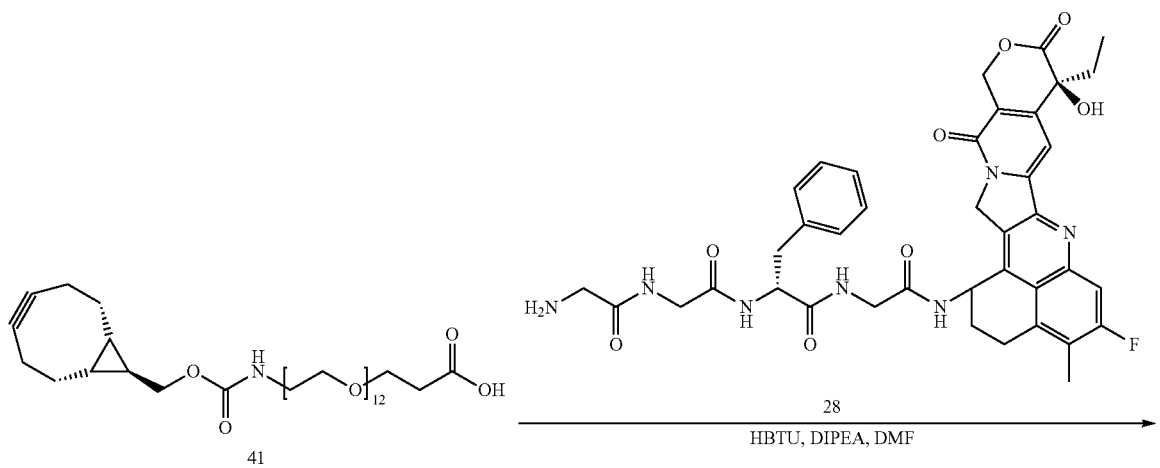

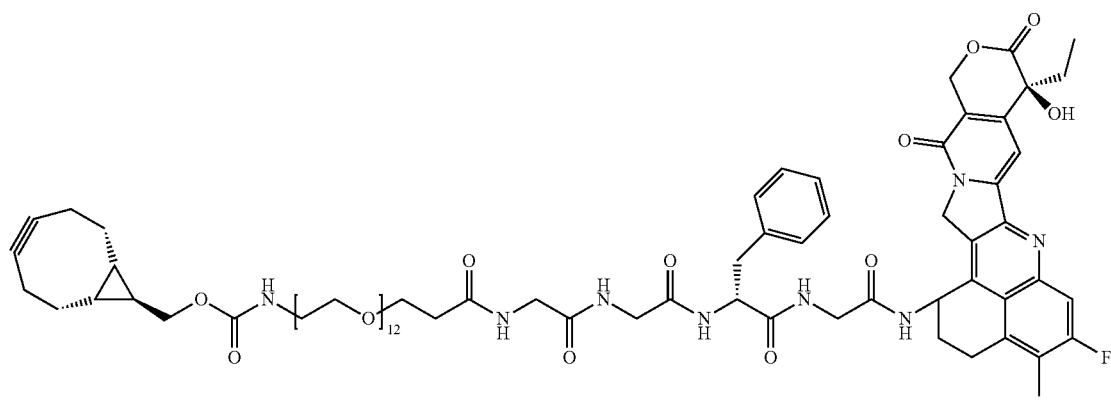

Synthesis of Compound 41

DIPEA (0.5 mL, 3 eq) was added to a mixture of commercial compound 38 (300 mg, 1 eq) and NH$_2$-PEG12-COOH (587 mg, 1.0 eq) in dichloromethane/DMF (4 mL/4 mL). The reaction mixture was stirred for 18 hours at room temperature. After the reaction was completed, the organic solvent was removed under reduced pressure. The residue was purified by column chromatography (DCM/MeOH) to afford a viscous liquid compound 41 (598 mg, 79% yield). LC-MS(ESI): m/z Calcd for [C$_{38}$H$_{67}$NO$_{16}$] 793.95 [M+1]$^+$, found 794.25 [M+1]$^+$.

Synthesis of BCN-PEG12-GGFG-Exatecan (Compound 42)

DIPEA (0.14 mL, 20 eq) was added to a mixture of compound 28 (30 mg, 1 eq), compound 41 (38 mg, 1.2 eq) and HBTU (23 mg, 1.5 eq) in DMF (2 mL). The reaction mixture was stirred for 2 hours at room temperature. After the reaction was completed, the organic solvent was removed under reduced pressure. The residue was purified by column chromatography (DCM/MeOH) to afford a yellow solid compound 42 (10.9 mg, 18% yield). LC-MS(ESI): m/z Calcd for [C$_{77}$H$_{105}$FN$_8$O$_{23}$] 1529.72 [M+1]$^+$, found 1530.9 [M+1]$^+$.

Example 15 Synthesis of BCN-PEG3-GGFG-Exatecan (Compound 43)

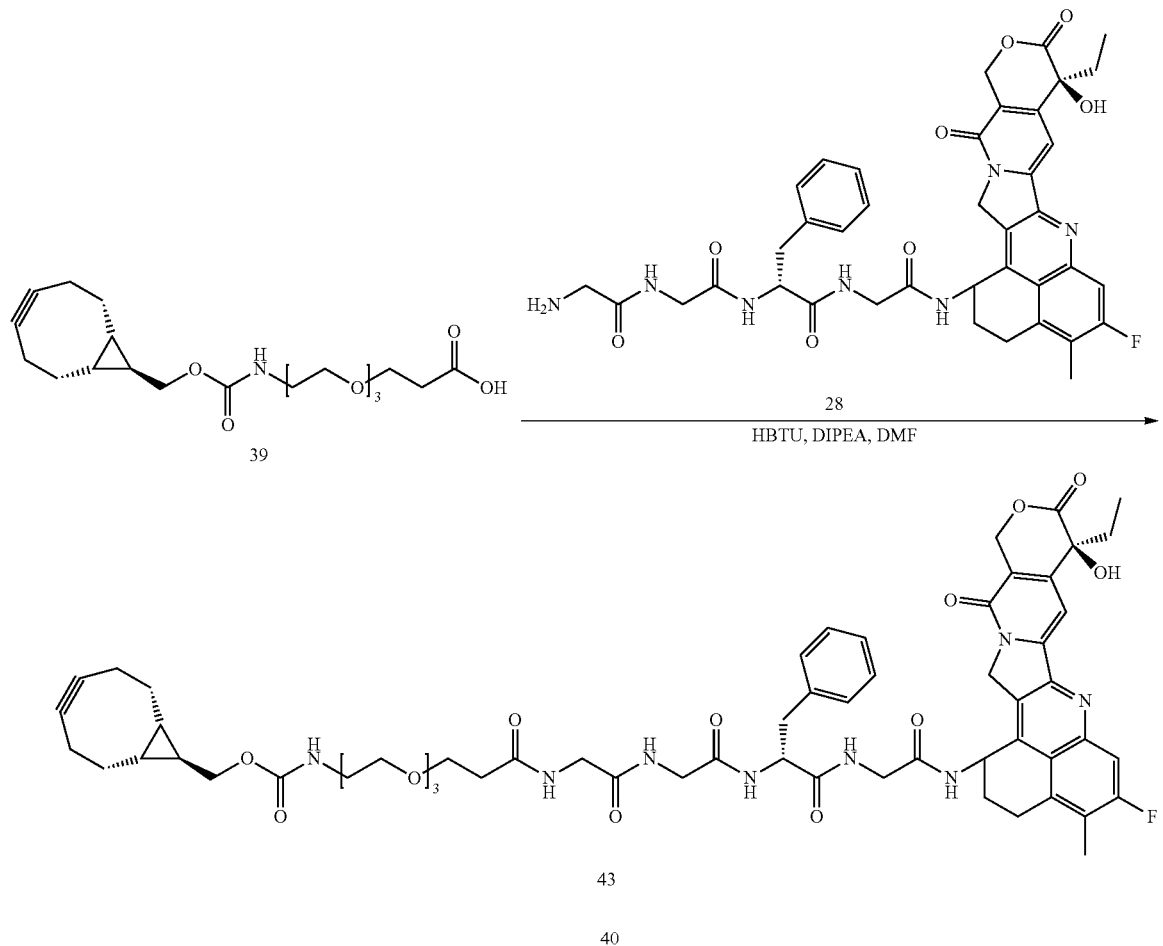

DIPEA (0.14 mL, 20 eq) was added to a mixture of compound 28 (30 mg, 1 eq), compound 39 (19 mg, 1.2 eq) and HBTU (23 mg, 1.5 eq) in DMF (2 mL). The reaction mixture was stirred for 2 hours at room temperature. After the reaction was completed, the organic solvent was removed under reduced pressure. The residue was purified by column chromatography (DCM/MeOH) to afford a yellow solid compound 43 (7.4 mg, 16% yield). LC-MS(ESI): m/z Calcd for $[C_{59}H_{69}FN_8O_{14}]$ 1133.24 $[M+1]^+$, found 1133.63 $[M+1]^+$.

Example 16 Synthesis of BCN-PEG12-GGFG-DXd2 (Compound 44)

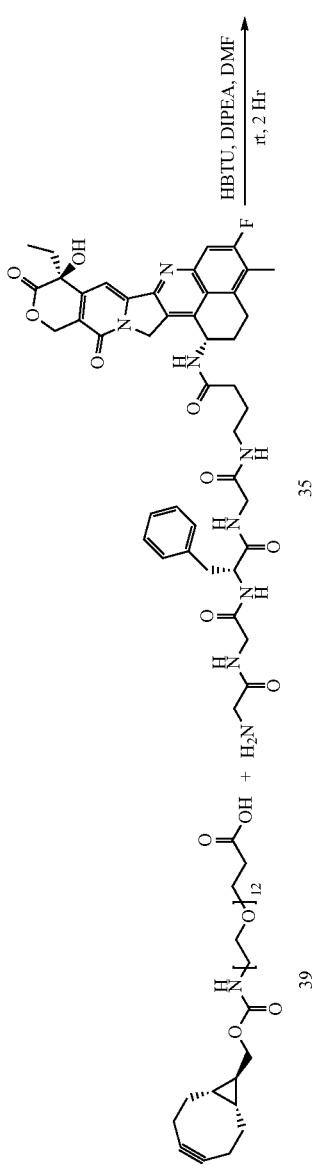
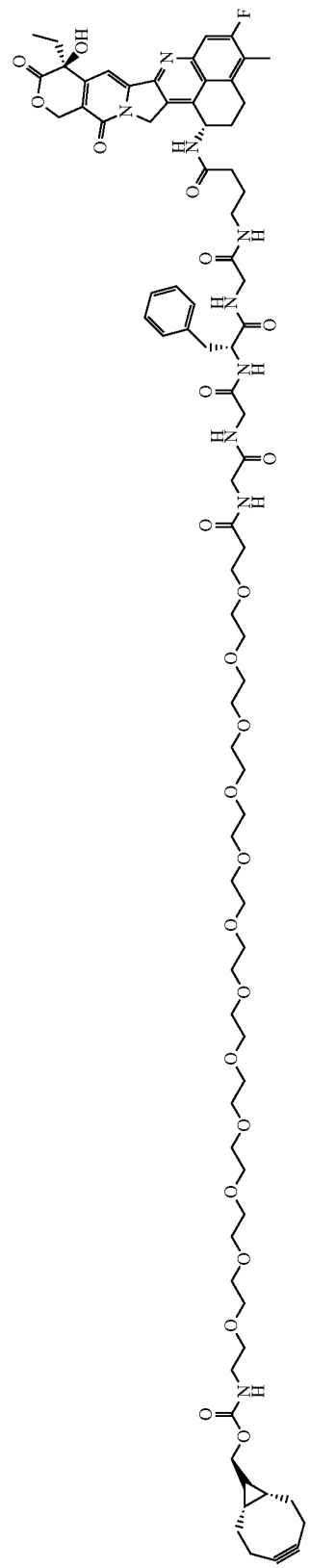

DIPEA (0.14 mL, 20 eq) was added to a mixture of compound 35 (34 mg, 1 eq), compound 39 (29 mg, 0.9 eq) and HBTU (23 mg, 1.5 eq) in DMF (2 mL). The reaction mixture was stirred for 1.5 hours at room temperature. After the reaction was completed, the organic solvent was removed under reduced pressure. The residue was purified by column chromatography (DCM/MeOH) to afford a yellow solid compound 44 (19 mg, 32% yield). LC-MS (ESI): m/z calcd for $C_{81}H_{112}FN_9O_{24}$ $[M+H]^+$: 1615.8, found: 1615.42.

Example 17 Synthesis of DBCO-PEG3-2(PEG3-VC-PAB-MMAE) (Compound 48)

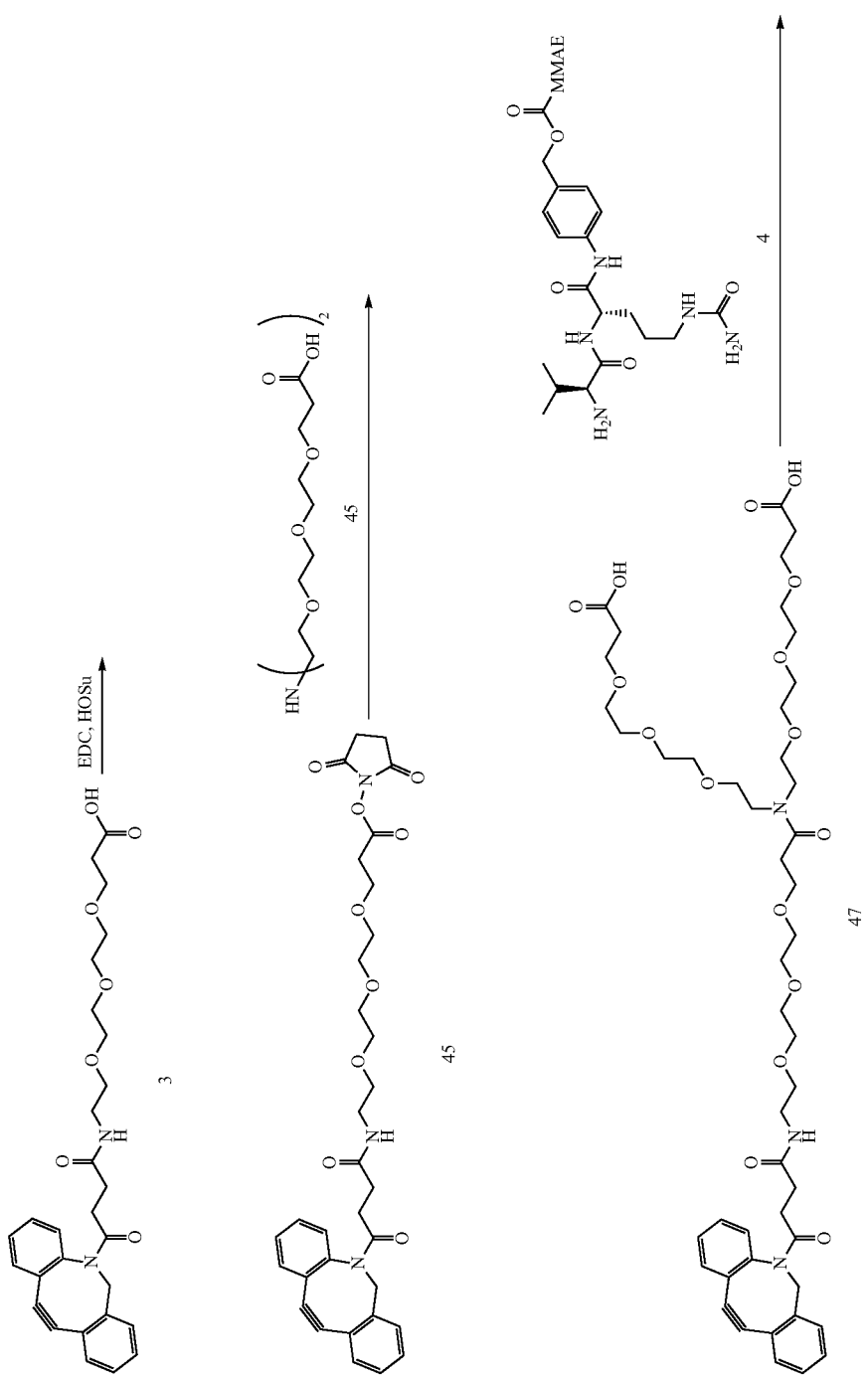

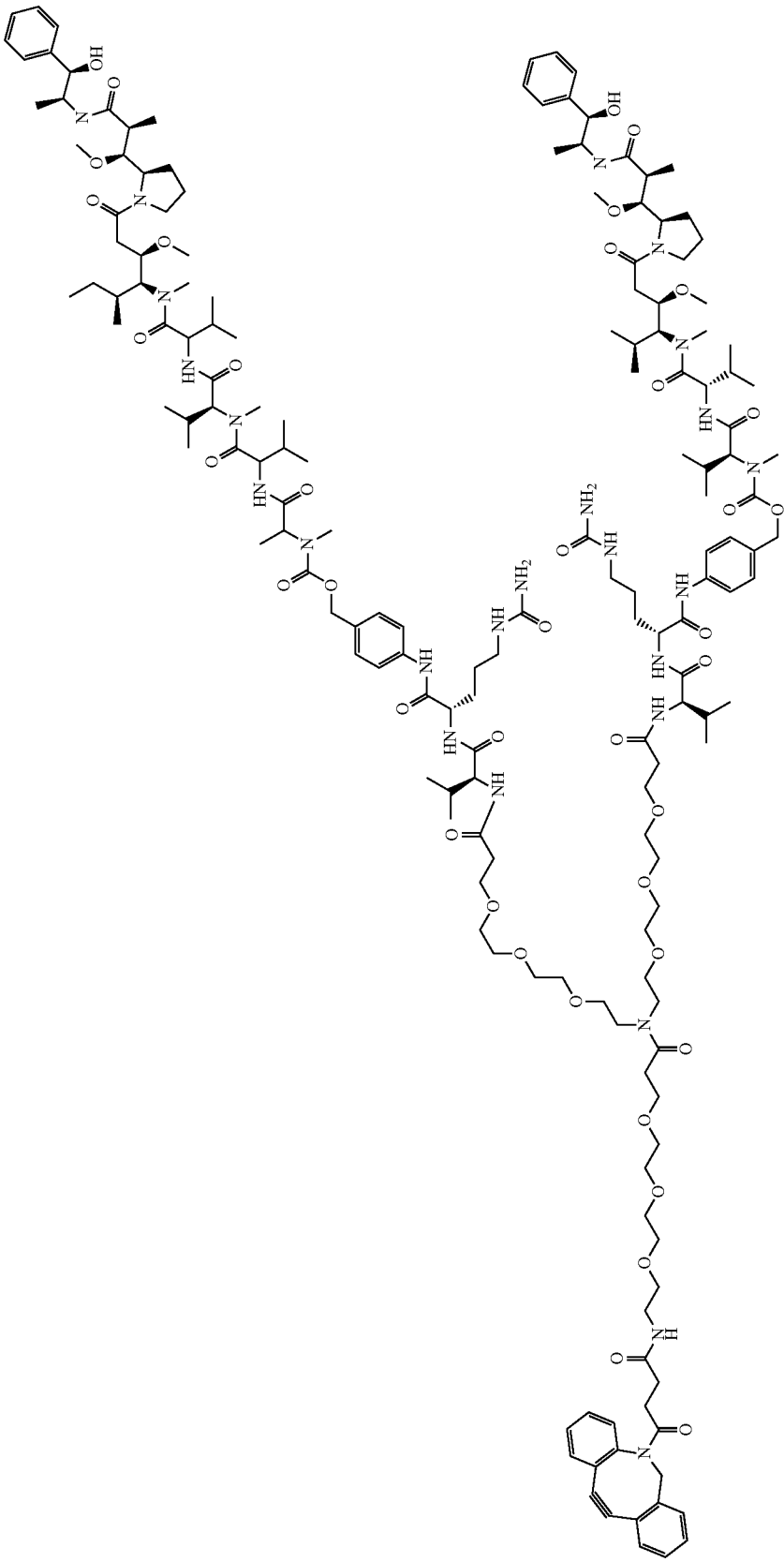

Synthesis of Compound 45

Compound 3 (490 mg, 1 eq) was added to a mixture of EDC (552 mg, 3 eq) and HOSu (333 mg, 3 eq) in in dry dichloromethane/dry DMF (2.4 mL/2.4 mL). The reaction mixture was stirred for 18 hours at room temperature under $N_2$ atmosphere. After the reaction was completed, the reaction mixture was extracted with dichloromethane and water. Then, the organic layer was washed with brine and dried over $MgSO_4$. The organic solvent was removed under reduced pressure to afford a viscous liquid compound 45 (856 mg) without further purification.

Synthesis of Compound 47

DIPEA (621.7 mg, 5 eq) was added to a mixture of compound 46 (856 mg) and NH-bis(PEG3-$CO_2$H) (574 mg, 1.4 eq) in dichloromethane/DMF (4.8 mL/4.8 mL). The reaction mixture was stirred for overnight at room temperature. After the reaction was completed, the organic solvent was removed under reduced pressure. The residue was purified by column chromatography (DCM/MeOH) to afford a viscous liquid compound 47 (485 mg, 54% yield). LC-MS(ESI): m/z Calcd for $[C_{46}H_{65}N_3O_{16}]$ 916.03 $[M]^+$, found 916.3 $[M]^+$. 1H NMR (600 MHz, DMSO) δ 12.17 (s, 2H), 7.77 (t, J=5.6 Hz, 1H), 7.68 (dd, J=7.7, 1.3 Hz, 1H), 7.62 (d, J=7.3 Hz, 1H), 7.48 (m, 3H), 7.36 (m, 2H), 7.30 (dd, J=7.4, 1.4 Hz, 1H), 5.02 (d, J=14.1 Hz, 1H), 3.61-3.56 (m, 8H), 3.54-3.32 (m, 39H), 3.31-3.26 (m, 2H), 3.16 (d, J=4.9 Hz, 1H), 3.13-3.03 (m, 3H), 2.63-2.54 (m, 4H), 2.43 (td, J=6.3, 2.7 Hz, 4H), 2.23 (dt, J=15.5, 7.7 Hz, 1H), 1.99 (m, 1H), 1.75 (m, 1H), 1.24 (d, J=5.9 Hz, 9H).

Synthesis of DBCO-PEG3-2(PEG3-VC-PAB-MMAE) (Compound 48)

DIPEA (22 mg, 3.2 eq) was added to a mixture of compound 47 (49 mg, 1 eq), compound 4 (72 mg, 1.2 eq) and HBTU (51 mg, 2.5 eq) in DMF (0.43 mL). The reaction mixture was stirred for 24 hours at room temperature. After the reaction was completed, the organic solvent was removed under reduced pressure. The residue was purified by column chromatography (DCM/MeOH) to afford a viscous liquid compound 48 (41 mg). LC-MS (TOF): m/z Calcd for $[C_{162}H_{249}N_{23}O_{38}]$ 3126.9 $[M]^+$, found 1042.95 $[M]^{3+}$, 1563.92 $[M]^{2+}$

Figure 21C:
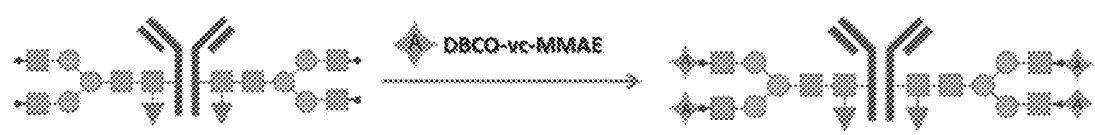

Example 18 Preparation of DCBPR2002-4(DBCO-VC-MMAE) (FIG. 21C)

Preparation of MES pH6.5 buffer: 4.881 g of MES free acid (2-Morpholinoethanesulfonic Acid, CAS 4432-31-9) was suspended in 750 mL dH2O. pH was adjusted to 6.5 by 10N NaOH(aq). Then, distilled water was added to the suspension until the volume reaches 1 L.

5.78 mL DBCO-vc-MMAE (10 mM in DMSO) was slowly added to a solution of DCBPR2002-4Az (34 mL, 2.5 mg/mL) in buffer (MES pH 6.5). The reaction mixture was stirred under argon at 37° C. for 18 hours. The antibody preparation was desalted and concentrated by using the Amicon Ultra-15 centrifugal filter device with 30 kDa NMWL in Na-Citrate pH6.5 buffer to give DCBPR2002-4 (DBCO-vc-MMAE). The drug-to-antibody ratio (DAR) of ADC was measured by LC-MS: 3.89.

Figure 21D:
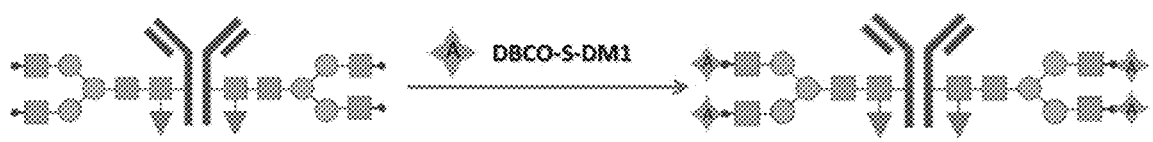

Example 19 Preparation of DCBPR2002-4(DBCO-S-DM1) (FIG. 21D)

4.48 mL DBCO-S-DM1 (10 mM in DMA) was slowly added to a solution of DCBPR2002-4Az (11.2 mL, 2.5 mg/mL) in buffer (MES pH 6.5). The reaction mixture was stirred under argon at 37° C. for 6 hours. The antibody preparation was desalted and concentrated by using the Amicon Ultra-15 centrifugal filter device with 30 kDa NMWL in Na-Citrate pH6.5 buffer to give DCBPR2002-4 (DBCO-S-DM1). The drug-to-antibody ratio (DAR) of ADC was measured by LC-MS: ~4.

Figure 21E:
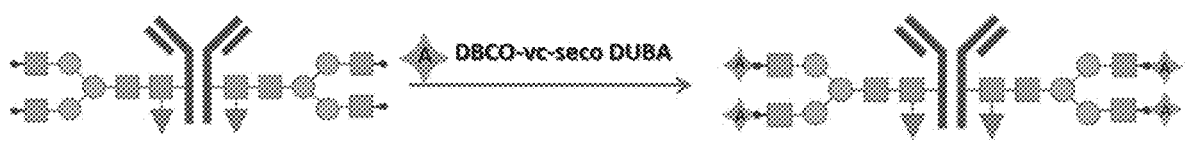

Example 20 Preparation of DCBPR2002-4(DBCO-Vc-Seco DUBA) (FIG. 21E)

0.4 mL DBCO-vc-seco DUBA (10 mM in DMA) and 1.2 mL DMA was slowly added to a solution of DCBPR2002-4Az (4 mL, 5 mg/mL) in buffer (MES pH 6.5). The reaction mixture was stirred under argon at 37° C. for 20 hours. The antibody preparation was desalted and concentrated by using the Amicon Ultra-15 centrifugal filter device with 30 kDa NMWL in Na-Citrate pH6.5 buffer to give DCBPR2002-4 (DBCO-vc-seco DUBA). The drug-to-antibody ratio (DAR) of ADC was measured by LC-MS: ~4.

Figure 21F:
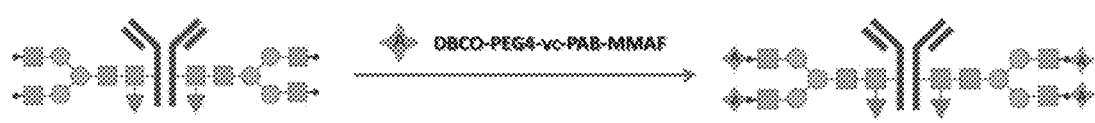

Example 21 Preparation of DCBPR2002-4(DBCO-PEG4-VC-PAB-MMAF) (FIG. 21F)

DBCO-PEG4-VC-PAB-MMAF is a commercial available linker-payload.

0.4 mL DBCO-PEG4-VC-PAB-MMAF (10 mM in DMSO) and 0.4 mL DMSO was slowly added to a solution of DCBPR2002-4Az (4 mL, 5 mg/mL) in buffer (MES pH 6.5). The reaction mixture was stirred under argon at 37° C. for 18 hours. The antibody preparation was desalted and concentrated by using the Amicon Ultra-15 centrifugal filter device with 30 kDa NMWL in Na-Citrate pH6.5 buffer to give DCBPR2002-4(DBCO-PEG4-vc-PAB-MMAF). The drug-to-antibody ratio (DAR) of ADC was measured by LC-MS: ~4.

Figure 21G:

Example 22 Preparation of DCBPR2002-4(DBCO-DTPA) (FIG. 21G)

0.24 mL DBCO-DTPA (10 mM in dd$H_2$O) was slowly added to a solution of DCBPR2002-4Az (2.4 mL, 5 mg/mL) in buffer (MES pH 6.5). The reaction mixture was stirred under argon at 37° C. for 18 hours. The antibody preparation was desalted and concentrated by using the Amicon Ultra-15 centrifugal filter device with 30 kDa NMWL in Na-Citrate pH6.5 buffer to give DCBPR2002-4(DBCO-DTPA). The drug-to-antibody ratio (DAR) of ADC was measured by LC-MS: ~4.

Figure 21H:
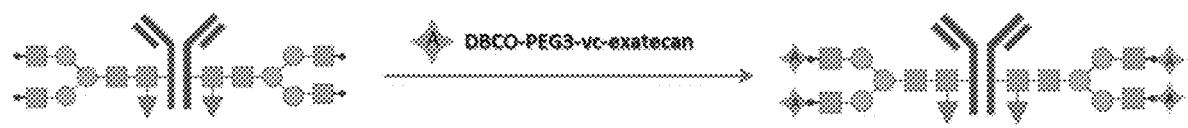

Example 23 Preparation of DCBPR2002-4(DBCO-PEG3-Vc-Exatecan) (FIG. 21H)

0.04 mL DBCO-PEG3-VC-exatecan (10 mM in DMA) and 0.12 mL DMA was slowly added to a solution of DCBPR2002-4Az (0.4 mL, 5 mg/mL) in buffer (MES pH 6.5). The reaction mixture was stirred under argon at 37° C. for 18 hours. The antibody preparation was desalted and concentrated by using the Amicon Ultra-15 centrifugal filter device with 30 kDa NMWL in MES pH6.5 buffer to give DCBPR2002-4(DBCO-PEG3-VC-exatecan). The drug-to-antibody ratio (DAR) of ADC was measured by LC-MS: 3.77.

Figure 21I:
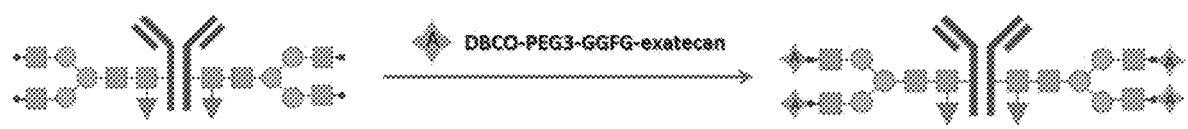

Example 24 Preparation of DCBPR2002-4(DBCO-PEG3-GGFG-Exatecan) (FIG. 21I)

0.02 mL DBCO-PEG3-GGFG-exatecan (10 mM in DMA) and 0.06 mL DMA was slowly added to a solution of DCBPR2002-4Az (0.2 mL, 5 mg/mL) in buffer (MES pH 6.5). The reaction mixture was stirred under argon at 37° C. for 18 hours. The antibody preparation was desalted and concentrated by using the Amicon Ultra-15 centrifugal filter device with 30 kDa NMWL in MES pH6.5 buffer to give DCBPR2002-4(DBCO-PEG3-GGFG-exatecan). The drug-to-antibody ratio (DAR) of ADC was measured by LC-MS: 3.21.

Figure 21J:
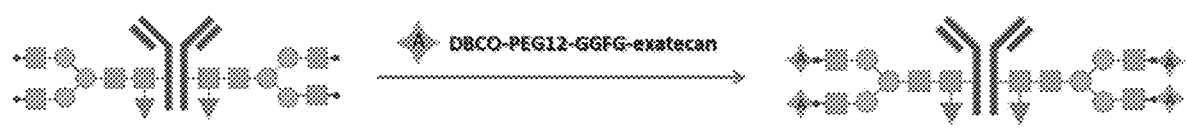

Example 25 Preparation of DCBPR2002-4(DBCO-PEG12-GGFG-Exatecan) (FIG. 21J)

0.02 mL DBCO-PEG12-GGFG-exatecan (10 mM in DMA) and 0.02 mL DMA was slowly added to a solution of DCBPR2002-4Az (0.1 mL, 10 mg/mL) in buffer (MES pH 6.5). The reaction mixture was stirred under argon at 37° C. for 18 hours. The antibody preparation was desalted and concentrated by using the Amicon Ultra-15 centrifugal filter device with 30 kDa NMWL in MES pH6.5 buffer to give DCBPR2002-4(DBCO-PEG12-GGFG-exatecan). The drug-to-antibody ratio (DAR) of ADC was measured by LC-MS: 3.91.

Figure 21K:
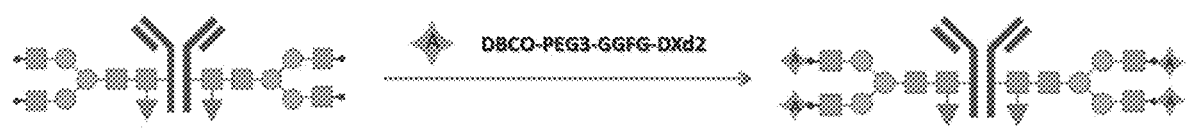

Example 26 Preparation of DCBPR2002-4(DBCO-PEG3-GGFG-DXd2) (FIG. 21K)

0.02 mL DBCO-PEG3-GGFG-DXd2 (10 mM in DMA) and 0.06 mL DMA was slowly added to a solution of DCBPR2002-4Az (0.213 mL, 4.7 mg/mL) in buffer (MES pH 6.5). The reaction mixture was stirred under argon at 37° C. for 18 hours. The antibody preparation was desalted and concentrated by using the Amicon Ultra-15 centrifugal filter device with 30 kDa NMWL in MES pH6.5 buffer to give DCBPR2002-4(DBCO-branched PEG3-GGFG-exatecan). The drug-to-antibody ratio (DAR) of ADC was measured by LC-MS: 3.12.

Figure 21L:
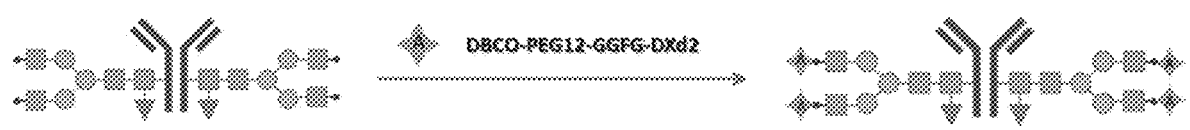

Example 27 Preparation of DCBPR2002-4(DBCO-PEG12-GGFG-DXd2) (FIG. 21L)

0.02 mL DBCO-PEG12-GGFG-DXd2 (10 mM in DMA) and 0.06 mL DMA was slowly added to a solution of DCBPR2002-4Az (0.213 mL, 4.7 mg/mL) in buffer (MES pH 6.5). The reaction mixture was stirred under argon at 37° C. for 18 hours. The antibody preparation was desalted and concentrated by using the Amicon Ultra-15 centrifugal filter device with 30 kDa NMWL in MES pH6.5 buffer to give DCBPR2002-4(DBCO-PEG12-GGFG-DX8951). The drug-to-antibody ratio (DAR) of ADC was measured by LC-MS: 3.52.

Figure 21M:
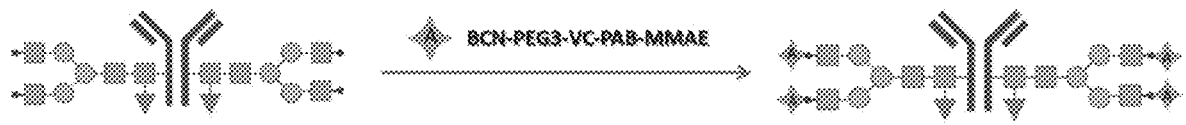

Example 28 Preparation of DCBPR2002-4(BCN-PEG3-VC-PAB-MMAE) (FIG. 21M)

0.0067 mL BCN-PEG3-VC-PAB-MMAE (10 mM in DMSO) and 0.0333 mL DMSO was slowly added to a solution of DCBPR2002-4Az (0.2 mL, 5 mg/mL) in buffer (MES pH 6.5). The reaction mixture was stirred under argon at 37° C. for 18 hours. The antibody preparation was desalted and concentrated by using the Amicon Ultra-15 centrifugal filter device with 30 kDa NMWL in MES pH6.5 buffer to give DCBPR2002-4(BCN-PEG3-VC-PAB-MMAE). The drug-to-antibody ratio (DAR) of ADC was measured by LC-MS: 2.67.

Figure 21N:
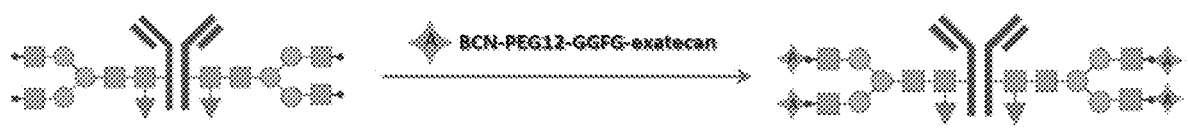

Example 29 Preparation of DCBPR2002-4(BCN-PEG12-GGFG-Exatecan) (FIG. 21N)

0.02 mL BCN-PEG12-GGFG-exatecan (10 mM in DMA) and 0.01 mL DMA was slowly added to a solution of DCBPR2002-4Az (0.05 mL, 10 mg/mL) in buffer (MES pH 6.5). The reaction mixture was stirred under argon at 37° C. for 42 hours. The antibody preparation was desalted and concentrated by using the Amicon Ultra-15 centrifugal filter device with 30 kDa NMWL in MES pH6.5 buffer to give DCBPR2002-4(BCN-PEG12-GGFG-exatecan). The drug-to-antibody ratio (DAR) of ADC was measured by LC-MS: 3.51.

Figure 21O:
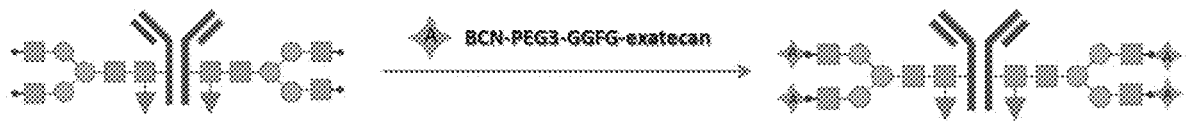

Example 30 Preparation of DCBPR2002-4(BCN-PEG3-GGFG-Exatecan) (FIG. 21O)

0.01 mL BCN-PEG3-GGFG-exatecan (10 mM in DMA) and 0.01 mL DMA was slowly added to a solution of DCBPR2002-4Az (0.05 mL, 10 mg/mL) in buffer (MES pH 6.5). The reaction mixture was stirred under argon at 37° C. for 18 hours. The antibody preparation was desalted and concentrated by using the Amicon Ultra-15 centrifugal filter device with 30 kDa NMWL in MES pH6.5 buffer to give DCBPR2002-4(BCN-PEG3-GGFG-exatecan). The drug-to-antibody ratio (DAR) of ADC was measured by LC-MS: 3.73.

Figure 21P:
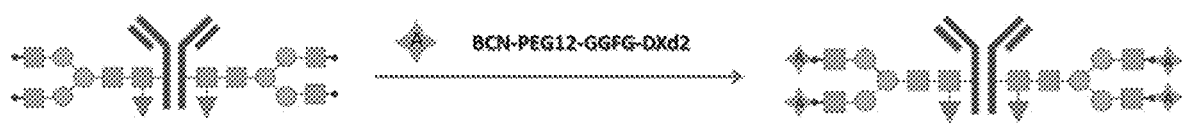

Example 31 Preparation of DCBPR2002-4(BCN-PEG12-GGFG-DXd2) (FIG. 21P)

0.02 mL BCN-PEG12-GGFG-DXd2 (10 mM in DMA) and 0.06 mL DMA was slowly added to a solution of DCBPR2002-4Az (0.08 mL, 10 mg/mL) in buffer (MES pH 6.5). The reaction mixture was stirred under argon at 37° C. for 18 hours. The antibody preparation was desalted and concentrated by using the Amicon Ultra-15 centrifugal filter device with 30 kDa NMWL in MES pH6.5 buffer to give DCBPR2002-4(DBCO-PEG12-GGFG-DXd2). The drug-to-antibody ratio (DAR) of ADC was measured by LC-MS: 3.51.

Figure 21Q:
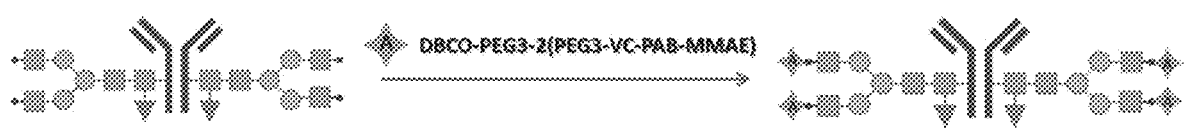

Example 32 Preparation of DCBPR2002-4(DBCO-PEG3-2(PEG3-VC-PAB-MMAE)) (FIG. 21Q)

0.02 mL DBCO-branched-PEG-VC-MMAE-B (10 mM in DMA) and 0.113 mL DMA was slowly added to a solution of DCBPR2002-4Az (0.333 mL, 3 mg/mL) in buffer (MES pH 6.5). The reaction mixture was stirred under argon at 37° C. for 18 hours. The antibody preparation was desalted and concentrated by using the Amicon Ultra-15 centrifugal filter device with 30 kDa NMWL in MES pH6.5 buffer to give DCBPR2002-4(DBCO-PEG3-2(PEG3-VC-PAB-MMAE)). The drug-to-antibody ratio (DAR) of ADC was measured by LC-MS: 5.68.

Figure 21R:
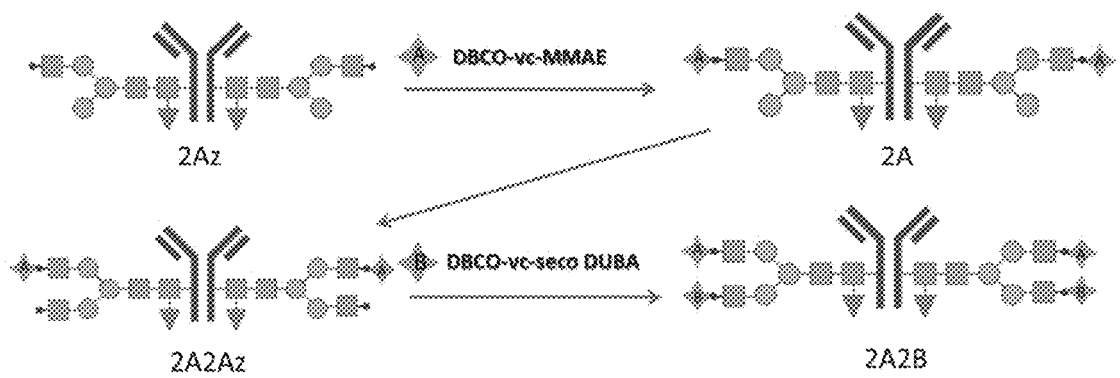

Example 33 Preparation of DCBPR2002-2(DBCO-Vc-MMAE)-2(DBCO-Vc-Seco DUBA) (FIG. 21R)

Synthesis of DCBPR2002-2(DBCO-vc-MMAE)

2.04 mL DBCO-vc-MMAE (10 mM in DMSO) was slowly added to a solution of DCBPR2002-2Az (12 mL, 5 mg/mL) in buffer (MES pH 6.5). The reaction mixture was stirred under argon at 37° C. for 20 hours. The antibody preparation was desalted and concentrated by using the Amicon Ultra-15 centrifugal filter device with 30 kDa NMWL in Na-Citrate pH6.5 buffer to give DCBPR2002-trimannosy-2(DBCO-vc-MMAE). The drug-to-antibody ratio (DAR) of ADC was measured by LC-MS: ~2.

General Synthesis of DCBPR2002-2(Linker-Payload)-2Az 5 mg DCBPR2002-2(linker-payload) and UDP-GlcNAz (2.5 mg) in 1000 µl 1× buffer SP (25 mM MES, 10 mM MnCl$_2$, pH 6.5) were incubated in the presence of rat MGAT-2 (0.05 mg) at 37° C. for 16 hours. After reaction, the antibody product was purified through Amicon Ultra-15 centrifugal filter device to obtain DCBPR2002-2(linker-payload) which with 2 active GlcNAz attached to the rest of terminal mannoses in the heavy chain. The product was subjected to reduced mass chromatography analysis.

Synthesis of DCBPR2002-2(DBCO-Vc-MMAE)-2(DBCO-Vc-Seco DUBA)

4.08 mL DBCO-vc-seco DUBA (10 mM in DMA) was slowly added to a solution of DCBPR2002-2(DBCO-vc-MMAE)-2Az (10.2 mL, 5 mg/mL) in buffer (MES pH 6.5). The reaction mixture was stirred under argon at 37° C. for 18 hours. The antibody preparation was desalted and concentrated by using the Amicon Ultra-15 centrifugal filter device with 30 kDa NMWL in Na-Citrate pH6.5 buffer to give DCBPR2002-2(DBCO-vc-MMAE)-2(DBCO-vc-seco DUBA). The drug-to-antibody ratio (DAR) of ADC was measured by LC-MS: ~4.

Figure 21S:
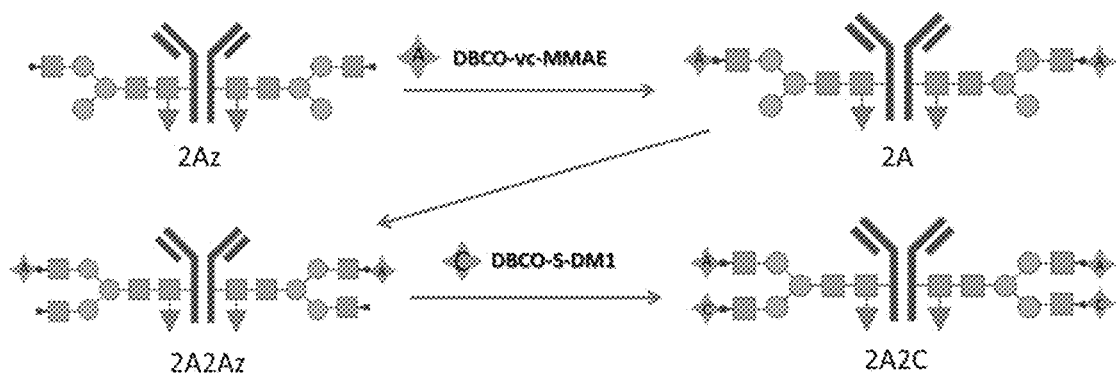

Example 34 Preparation of DCBPR2002-2(DBCO-Vc-MMAE)-2(DBCO-S-DM1) (FIG. 21S)

Synthesis of DCBPR2002-2(DBCO-vc-MMAE)-2(DBCO-S-DM1)

2.08 mL DBCO-S-DM1 (10 mM in DMA) was slowly added to a solution of DCBPR2002-2(DBCO-vc-MMAE)-2Az (5.2 mL, 5 mg/mL) in buffer (MES pH 6.5). The reaction mixture was stirred under argon at 37° C. for 18 hours. The antibody preparation was desalted and concentrated by using the Amicon Ultra-15 centrifugal filter device with 30 kDa NMWL in Na-Citrate pH6.5 buffer to give DCBPR2002-2(DBCO-vc-MMAE)-2(DBCO-S-DM1). The drug-to-antibody ratio (DAR) of ADC was measured by LC-MS: ~4.

Figure 21T:
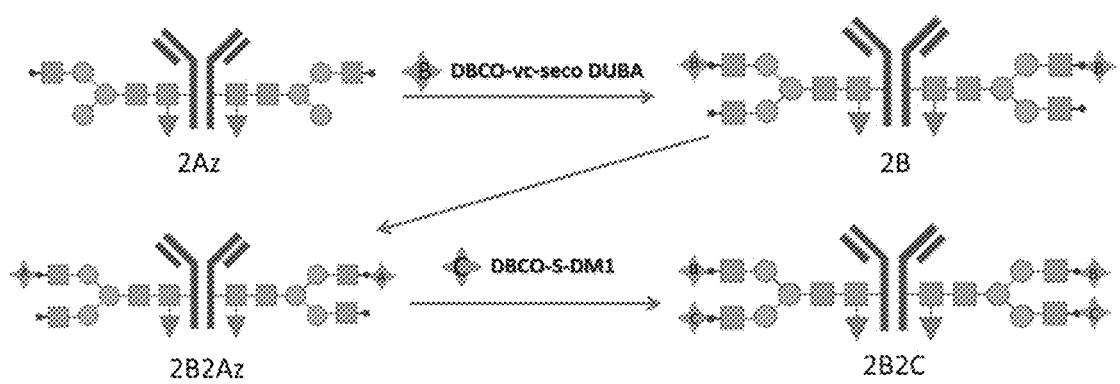

Example 35 Preparation of DCBPR2002-2(DBCO-Vc-Seco DUBA)-2(DBCO-S-DM1) (FIG. 21T)

Synthesis of DCBPR2002-2(DBCO-Vc-Seco DUBA)

7.2 mL DBCO-vc-seco DUBA (10 mM in DMSO) was slowly added to a solution of DCBPR2002-2Az (18 mL, 5 mg/mL) in buffer (MES pH 6.5). The reaction mixture was stirred under argon at 37° C. for 20 hours. The antibody preparation was desalted and concentrated by using the Amicon Ultra-15 centrifugal filter device with 30 kDa NMWL in Na-Citrate pH6.5 buffer to give DCBPR2002-2 (DBCO-vc-seco DUBA). The drug-to-antibody ratio (DAR) of ADC was measured by LC-MS: ~2.

Synthesis of DCBPR2002-2(DBCO-Vc-Seco DUBA)-2 (DBCO-S-DM1)

2.4 mL DBCO-S-DM1 (10 mM in DMA) was slowly added to a solution of DCBPR2002-2(DBCO-vc-seco DUBA)-2Az (6 mL, 5 mg/mL) in buffer (MES pH 6.5). The reaction mixture was stirred under argon at 37° C. for 18 hours. The antibody preparation was desalted and concentrated by using the Amicon Ultra-15 centrifugal filter device with 30 kDa NMWL in Na-Citrate pH6.5 buffer to give DCBPR2002-2(DBCO-vc-seco DUBA)-2(DBCO-S-DM1). The drug-to-antibody ratio (DAR) of ADC was measured by LC-MS: ~4.

Example 36 SDS-PAGE

The ADCs of the invention may be analyzed with techniques known in the art, such as SDS-PAGE and HPLC. For example, the solution of anti-MSLN mAb and anti-MSLN ADCs can be analyzed by using a 4-12% non-reducing and reducing SDS-PAGE gel followed by Coomassie brilliant blue staining.

Example 37 Payload Coupling Assay

Evaluation of drug-to-antibody ratio (DAR) is important to monitor payload conjugation efficiency on target antibody. The drug-to-antibody ratio may affect the therapeutic efficacy of anti-MSLN ADC products. Liquid chromatography-mass spectrometry (LC-MS) is the method of choice to determine the drug-to-antibody ratio (DAR) and drug load distribution of lysine-linked antibody-drug conjugates (ADCs). The area percentage of a peak represents the relative distribution of a particular drug-loaded ADC species. The weighted average DAR is then calculated by using the percentage peak area information and the drug load numbers.

Figure 7:
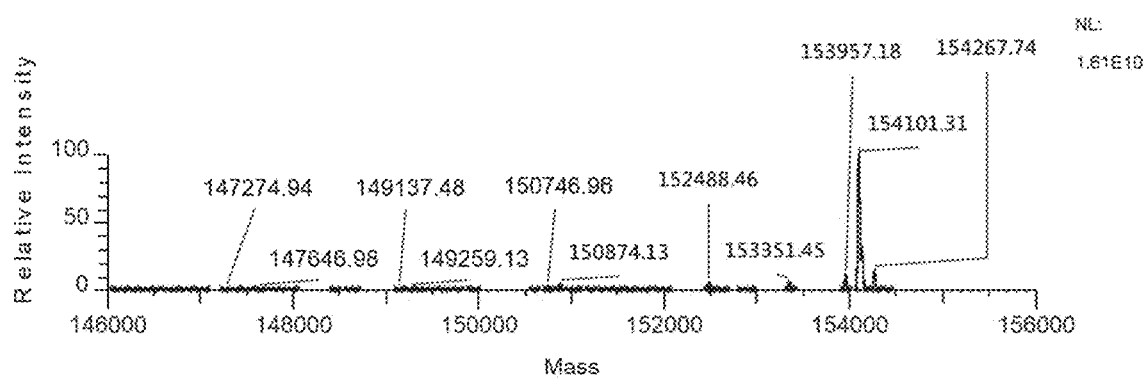
FIG. 7 shows the mass analysis of an ADC DCBPR2002-4(DBCO-vc-MMAE).

FIG. 7 illustrates one example of mass analysis of an ADC of the invention (DCBPR2002-4(DBCO-vc-MMAE)), which indicates a distribution of various numbers of drug attached to an antibody with the most abundant species having 4 drugs attached to an antibody. The average drug-to-antibody ratio (DAR) in this sample is 4.07.

Example 38 ELISA Binding Affinity

Figure 5:
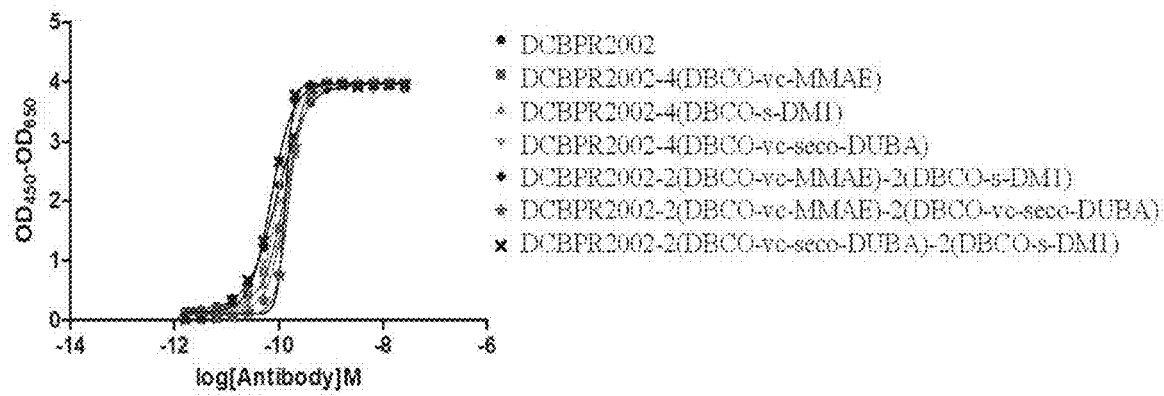
FIG. 5 shows the ELISA binding affinity of the detected ADCs.

100 µL of mesothelin in a coating buffer at a concentration of 1 µg/mL was added to and coated on each well of a plate. The plates were sealed and incubated at 4° C. overnight. The wells were aspirated and washed with 300 µL of PBST (0.05% Tween 20) for 3 times. The wells were blocked by adding 200 µL of PBS-5% skim milk and incubated at 37° C. for 1 hour. The wells were aspirated and washed with 300 µL/well of PBST (0.05% Tween 20) for 3 times. 100 µL of 400 ng ADC sample diluted with PBS was added to each well, and the plates were then incubated at 37° C. for 1 hour. The wells were aspirated and washed with 300 µL of PBST (0.05% Tween 20) for 3 times. 50 µl of anti-human Kappa light chains (1:5000) was added to each well, and the plates were incubated at 37° C. for 1 hour. The wells were aspirated and washed with 300 µL/well of PBST (0.05% Tween 20) for 3 times. 100 µl of TMB was added to each well, and the plates were incubated at room temperature for 15 minutes. The color development was stopped by adding 100 µL of 1N HCl. The plates were measured at absorbance of 450-650 nm by using an ELISA reader. The data are shown in FIG. 5.

DCBPR2002 Kd=9.243e-011; DCBPR2002-4(DBCO-vc-MMAE) Kd=1.329e-010; DCBPR2002-4(DBCO-s-DM1) Kd=1.449 e-010; DCBPR2002-4(DBCO-vc-seco- DUBA) Kd=9.747e-011; DCBPR2002-2(DBCO-vc-MMAE)-2(DBCO-s-DM1) Kd=1.355 e-010; DCBPR2002-2(DBCO-vc-MMAE)-2(DBCO-vc-seco-DUBA) Kd=1.580 e-010; and DCBPR2002-2(DBCO-vc-seco-DUBA)-2(DBCO-s-DM1) Kd=7.315 e-011.

Example 39 Binding Kinetics of Anti-Mesothelin ADCs

The kinetic constant of the anti-mesothelin ADCs interaction against mesothelin was determined by surface plasma resonance (Biacore® T100, Biacore, Inc., Piscataway, NJ). The flow cell of the CM5 wafer was fixed with approximately 10,000 reaction units (RU) of anti-human IgG-Fc (Biacore®) in 10 mM glycine pH 5.0 at 10 μL/min for 600 seconds. 10 μg/mL of anti-mesothelin antibody and anti-mesothelin ADCs diluted in TBS at 10 μl/min were captured on CM5 chips. Four concentrations (from 3.7 to 100 nM) of human mesothelin recombinant protein and zero concentration (flow buffer) in 100 μl/min binding were recorded in PBS containing 1 mM $CaCl_2$ for 3 minutes. The dissociation of the complex was measured for 10 minutes. The water surface was regenerated by injecting 3 M $MgCl_2$ and 3 mM EGTA at 10 μl/min for 60 seconds. The curve obtained after subtracting the reference and buffer signals was taken into the 1:1 Langmuir binding model using the Biacore® T100 evaluation software (Biacore®). Ka, Kd and KD are shown in Table 4. Kinetic analysis showed that anti-mesothelin antibody and anti-mesothelin ADCs have similar ka(on) and kd(off) rates.

TABLE 4

| Analyte | MSLN | | | | |
|---|---|---|---|---|---|
| Antibodies | $K_a$ | $K_d$ | $K_D$ | Rmax(RU) | $Chi^2(RU^2)$ |
| DCBPR2002 | 5.091E+6 | 8.593E−5 | 1.688E−11 | 58.1 | 4.08 |
| DCBPR2002-4(DBCO-vc-MMAE) | 5.395E+6 | 1.17E−4 | 2.168E−11 | 55.99 | 3.29 |
| DCBPR2002-2(DBCO-vc-MMAE)-2(DBCO-vc-seco-DUBA) | 4.752E+6 | 1.218E−4 | 2.563E−11 | 50.98 | 2.40 |

Example 40 In Vitro Cytotoxicity Study (KLM-1 and OVCAR-3)

Pancreatic cancer cell line KLM-1 was respectively grown in RPMI 1640 Medium (ATCC modification) medium supplemented with 10% fetal bovine serum. Ovarian carcinoma cell line OVCAR-3 was grown in RPMI 1640 Medium (ATCC modification) medium supplemented with 20% fetal bovine serum. The KLM-1 & OVCAR-3 cell lines were maintained in an atmosphere of 5% $CO_2$ in a humidified 37° C. incubator. The day before treatment, cells were collected and seeded into 96-well plates (4,000 cells per well). On the second day, cells were treated with 3-fold serial dilution concentration of toxic payloads and ADCs. Each treatment was performed in eight triplicate data points. After the treatment of 72 hours, cell viability was assessed by CellTiter-Glo® kit (Promega) according to the manufacturer's instruction. At the end of the incubation, luminescence was measured using a SpectraMax i3x Multi Mode Detection Platform (Molecular Devices). Compound cytotoxicity was evaluated in comparison to cells treated with 0.05% PBS (ADCs) or 0.05% DMSO (toxic payload). $IC_{50}$ values were calculated by fitting viability data with a four-parameter logistic equation using GraphPad prism 5.0 software. The results are shown in Table 5.

TABLE 5

| | Cell Titer-Glo Luminescent cell viability assay | |
|---|---|---|
| Relative $IC_{50}$ | MSLN+ | |
| (nM of toxic payload/ADCs) | KLM-1 | OVCAR-3 |
| DM1 | 2.1 | 1.6 |
| MMAE | 0.3 | 0.3 |
| seco-DUBA | 0.04 | 0.02 |
| Exatecan | | 20.1 |

$IC_{50}$ values of toxic payloads and ADCs.

TABLE 5-continued

IC$_{50}$ values of toxic payloads and ADCs.

| Relative IC$_{50}$ | Cell Titer-Glo Luminescent cell viability assay | |
|---|---|---|
| | MSLN+ | |
| (nM of toxic payload/ADCs) | KLM-1 | OVCAR-3 |
| DXd | | >100 |
| DXd2 | | >1000 |
| DCBPR2002-4(DBCO-vc-MMAE) | 101.3 | 1.0 |
| DCBPR2002-4(DBCO-vc-seco-DUBA) | 19.4 | 23.9 |
| DCBPR2002-4(DBCO-s-DM1) | 13.9 | 2.6 |
| DCBPR2002-4(DBCO-PEG4-vc-PAB-MMAF) | | 1.2 |
| DCBPR2002-4(DBCO-PEG3-vc-exatecan) | | 143 |
| DCBPR2002-4(DBCO-PEG3-GGFG-exatecan) | | 130.2 |
| DCBPR2002-4(DBCO-PEG12-GGFG-exatecan) | | >100 |
| DCBPR2002-4(DBCO-PEG3-GGFG-DXd2) | | 19.7 |
| DCBPR2002-4(DBCO-PEG12-GGFG-DXd2) | | 21.1 |
| DCBPR2002-4(BCN-PEG12-GGFG-exatecan) | | 15.6 |
| DCBPR2002-4(BCN-PEG3-GGFG-exatecan) | | >96.7 |
| DCBPR2002-4(BCN-PEG12-GGFG-DXd2) | | >86.7 |
| DCBPR2002-2(DBCO-vc-MMAE)-2(DBCO-vc-seco-DUBA) | 46.0 | 43.3 |
| DCBPR2002-2(DBCO-vc-seco-DUBA)-2(DBCO-s-DM1) | 27.0 | 36.3 |
| DCBPR2002-2(DBCO-vc-MMAE)-2(DBCO-s-DM1) | 15.4 | 4.6 |

Example 41 Internalization Assay

Figure 6:
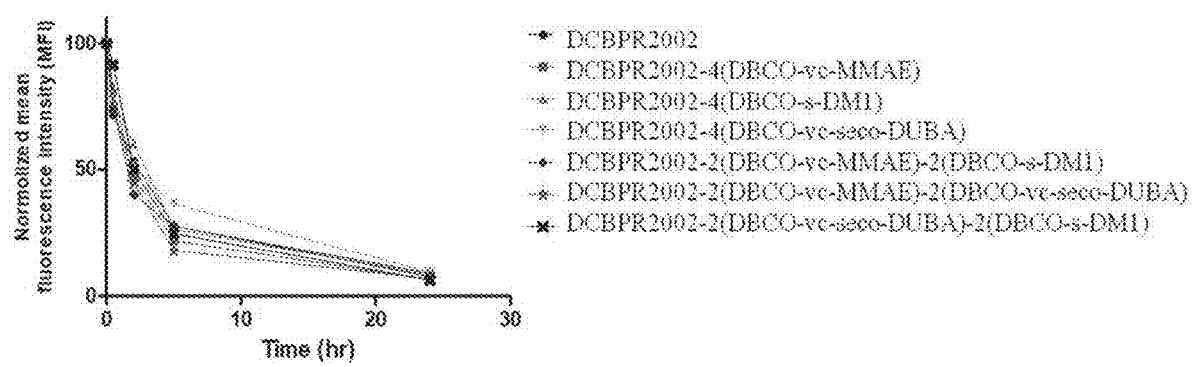
FIG. 6 shows the results of ADC internalization.

KLM-1 or OVCAR3 cells were trypsinized, and then harvested and resuspended in FAC buffer. Controls: secondary Ab anti-human IgG PE (1:200) was added to the KLM-1 or OVCAR3 cells. The cells were incubated at 4° C. for time intervals of 0, 0.5, 2, 5 and 24 hours, and then washed by 1 mL FACS buffer. The supernatant was discarded. Testing groups: KLM-1 or OVCAR3 cells were pre-incubated with 10 μg/mL tir-mannosyl anti-mesothelin ADCs in FACS buffer on ice for 60 min, washed three times with FACS buffer, and then incubated at 37° C. for time intervals of 0, 0.5, 2, 5 and 24 hours. The cells were analyzed by flow cytometry (BD LSRFortessa) and the results are shown in FIG. 6.

Example 42 In Vivo PK

This study used Meso Scale Discovery (MSD) Electrochemiluminescent (ECL) method to conduct the pharmacokinetic analysis of DCBPR2002-4(DBCO-vc-MMAE) in BALB/c mice and rat samples. The MSD assay can measure both conjugated and unconjugated antibodies. As illustrated in this example, or total antibody assay the plate is coated with goat anti-human IgG, which can capture all humanized antibodies (conjugated and unconjugated). For the conjugated antibody assay, the plate is coated with an antibody against the payload (drug), such as anti-MMAE antibody.

The mice were administered at a dose level of 3 mg/kg via the tail vein. Blood samples were then obtained at different time points for determining the concentrations of DCBPR2002-4(DBCO-vc-MMAE) in mice by MESO QuickPlex SQ 120 method. The pharmacokinetic parameters of DCBPR2002-4(DBCO-vc-MMAE) were analyzed by noncompartmental analysis using Phoenix™ for WinNonlin Program, version 6.3.

Table 6 summarizes the results for the PK studies. Total antibody MSD assay: measuring both conjugated and unconjugated antibody. Conjugated antibody MSD assay: measuring conjugated antibody only. The in vivo half live of DCBPR2002-4(DBCO-vc-MMAE) is around 87.2 hours which is because of the higher degree of linker proteolysis observed in mouse compared to that of the other species can be attributed to the enzyme carboxylesterase 1C, of which the valine-citrulline linker on our ADC is a substrate.

The in vivo pharmacokinetic study was designed for the comparison the linker-payload stability of trimannosyl-conjugated and cysteine-conjugated synthesis ADC (Adcetris). The rats were administered DCBPR2002-4(DBCO-vc-MMAE) and Adcetris at a dose level of 5 mg/kg via the tail vein. Serum samples were then obtained at different time points for determination of the concentrations of DCBPR2002-4(DBCO-vc-MMAE) and Adcetris in rats by MESO QuickPlex SQ 120 method. The pharmacokinetic parameters of DCBPR2002-4(DBCO-vc-MMAE) and Adcetris were analyzed by noncompartmental analysis using Phoenix™ for WinNonlin Program, version 6.3.

Figure 8:
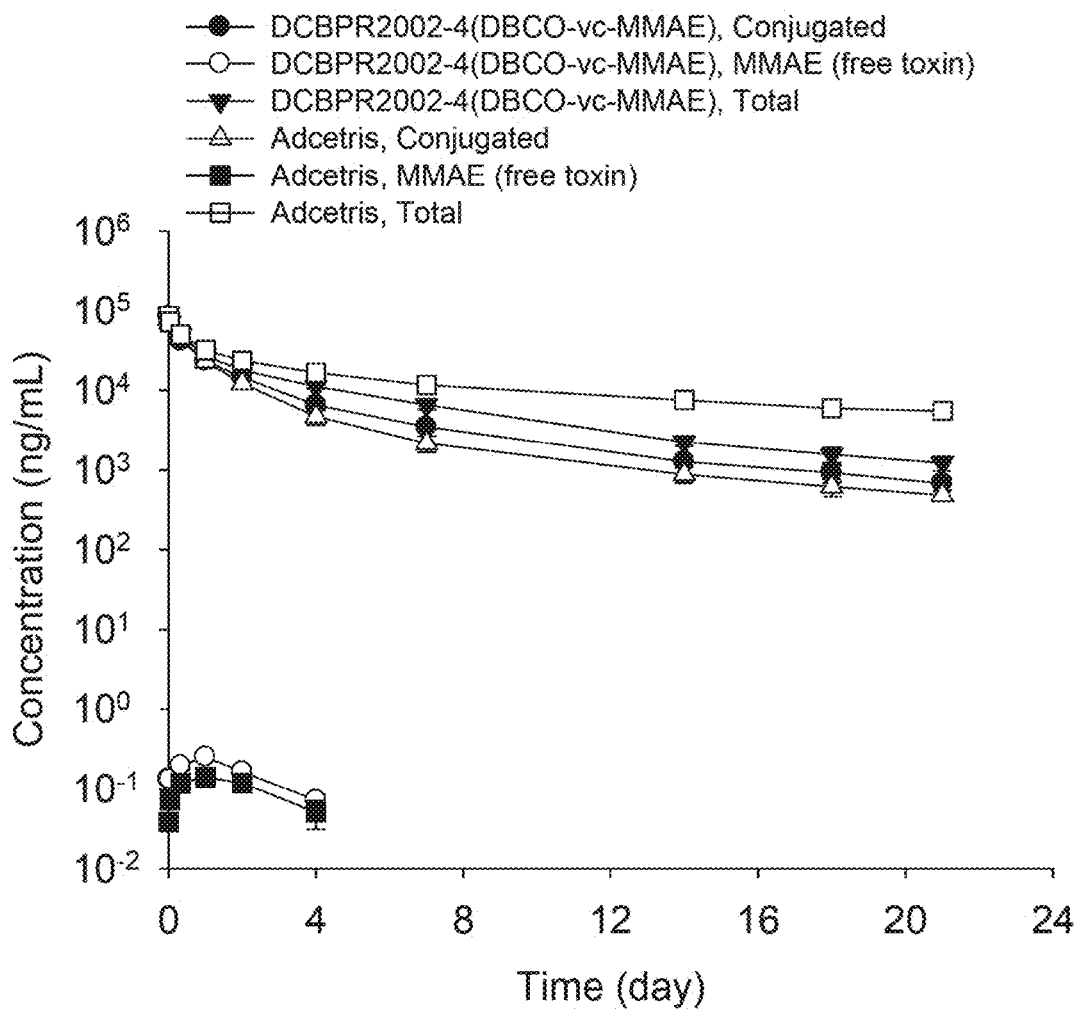
FIG. 8 shows the results for pharmacokinetic profile of ADC DCBPR2002-4(DBCO-vc-MMAE).

Table 7 summarizes the results for the PK studies. Total antibody MSD assay: measuring both conjugated and unconjugated antibody. Conjugated antibody MSD assay: measuring conjugated antibody only. The in vivo half live of DCBPR2002-4(DBCO-vc-MMAE) is 194±35.0 hrs for total antibody; the half live of conjugated antibody is 148±8.14 hours for DCBPR2002-4(DBCO-vc-MMAE) and 182±10.9 hours for Adcetris. (FIG. 8)

TABLE 6

| Group | | $C_0$ (ng/mL) | $AUC_{(0-last)}$ (ng * hr/mL) | $AUC_{(0-\infty)}$ (ng * hr/mL) | MRT (hr) | $t_{1/2}$ (hr) | CL (mL/min/Kg) | $V_{ss}$ (L/Kg) |
|---|---|---|---|---|---|---|---|---|
| DCBPR2002-4 (DBCO-vc-MMAE) (N = 3) | Total | 346 ± 11.9 | 25963 ± 6257 | 34112 ± 10415 | 299 ± 120 | 220 ± 84.3 | 0.008 ± 0.003 | 0.129 ± 0.019 |
| | Conjugated | 275 ± 2.8 | 2264 ± 49.3 | 2274 ± 49.6 | 23.4 ± 4.99 | 87.2 ± 27.4 | 0.110 ± 0.002 | 0.155 ± 0.033 |

TABLE 7

| Group | | $C_0$ (ng/mL) | $AUC_{(0-last)}$ (ng * hr/mL) | $AUC_{(0-\infty)}$ (ng * hr/mL) | MRT (hr) | $t_{1/2}$ (hr) | CL (mL/min/Kg) | $V_{ss}$ (L/Kg) |
|---|---|---|---|---|---|---|---|---|
| DCBPR2002-4(DBCO-MMAE) (N = 3) | Total | 94121 ± 1186 | 4013185 ± 216117 | 4363325 ± 298790 | 160 ± 26.3 | 194 ± 35.0 | 0.019 ± 0.001 | 0.183 ± 0.024 |
| | Conjugated | 80955 ± 2308 | 2334505 ± 158551 | 2400450 ± 157340 | 85.6 ± 2.48 | 148 ± 8.14 | 0.035 ± 0.002 | 0.179 ± 0.017 |
| Adcetris (N = 3) | Total | 87418 ± 7387 | 6500218 ± 744720 | 9154784 ± 1534447 | 405 ± 4.33 | 351 ± 10.0 | 0.009 ± 0.002 | 0.224 ± 0.035 |
| | Conjugated | 84849 ± 10597 | 3863369 ± 568713 | 4274931 ± 600961 | 185 ± 5.92 | 182 ± 10.9 | 0.020 ± 0.003 | 0.219 ± 0.033 |

Comparison of the total and conjugated antibody of the pharmacokinetic profile of DCBPR2002-4(DBCO-vc-MMAE) and Adcetris, the difference between the curve of total antibody and conjugated antibody is closed on DCBPR2002-4(DBCO-vc-MMAE) than that of Adcetris. The in vivo results demonstrated that the presented trimannosyl conjugation compared with cysteine conjugation (Adcetris) has the difference in the stability of the conjugated linker-payload.

Example 43 Xenograft Model of Anti-MSLN ADC (Pancreatic Cancer)

The aim of this study was to evaluate the in vivo anti-tumor efficacy of DCBPR2002-lysine-DBCO-vc-MMAE (DBCO-vc-MMAE linking to polypeptide of antibody through lysine activated by azide), and DCBPR2002-4 (DBCO-vc-MMAE) in KLM-1 human pancreatic cancer xenograft model in male NOD SCID mice.

Formulations respectively comprising test article DCBPR2002 lysine-DBCO-vc-MMAE, test article DCBPR2002-4(DBCO-vc-MMAE), and a corresponding vehicle were formulated by diluting the stock with a 25 mM sodium citrate buffer (pH 6.5). Each of the formulations was administered intravenously (IV) to the mice once weekly for three weeks.

The KLM-1 cells were maintained in vitro as a monolayer culture in RPMI-1640 medium supplemented with 10% fetal bovine serum at 37° C. in an atmosphere of 5% $CO_2$ in air. The tumor cells were routinely sub-cultured twice weekly by trypsin-EDTA treatment. The cells growing in an exponential growth phase were harvested and counted for tumor inoculation.

Male NOD SCID mice at age of 6-7 weeks were purchased from BioLasco Taiwan Co., LTD. and quarantined for one week. Five mice were housed in each cage. All animals were hosted in the animal facility with a 12-h light/12-h dark cycle at 19-25° C. Animals had free access to rodent pellet foods and water ad libitum.

KLM-1 cells were subcutaneously (SC) implanted ($4 \times 10^6$ cells in 1:1 PBS/matrigel mixture at 0.1 mL per mouse) into the right flank of male NOD SCID mice. When the average tumor volume had reached about 200 $mm^3$, the mice were randomly divided into 3 groups (N=6 per group). Each of the vehicle, DCBPR2002-lysine-DBCO-vc-MMAE (15 mg/kg), and DCBPR2002-4(DBCO-vc-MMAE) (15 mg/kg) was intravenously administered once weekly for 3 weeks.

The tumor volumes, body weights, mortality, and signs of overt toxicity were monitored and recorded three times weekly for 28 days. Tumor volumes ($mm^3$) were measured three times per week using calipers and calculated according to the formula: Tumor Volume=$(w^2 \times l)/2$, where w=width and l=length in diameter (mm) of the tumor. The percentages of tumor growth inhibition (TGI) were calculated using the following formula: % TGI=$[1-(T/C)] \times 100\%$, where T and C represent the mean tumor volumes of the treatment group and the control group, respectively. A TGI (%) value≥58% was considered significant anti-tumor activity. One-way ANOVA followed by Dunnett's test was applied for comparison between the vehicle and test article-treated groups. Differences are considered significant at *P<0.05. Animals were weighed three times weekly until the completion of the study.

Figure 9:
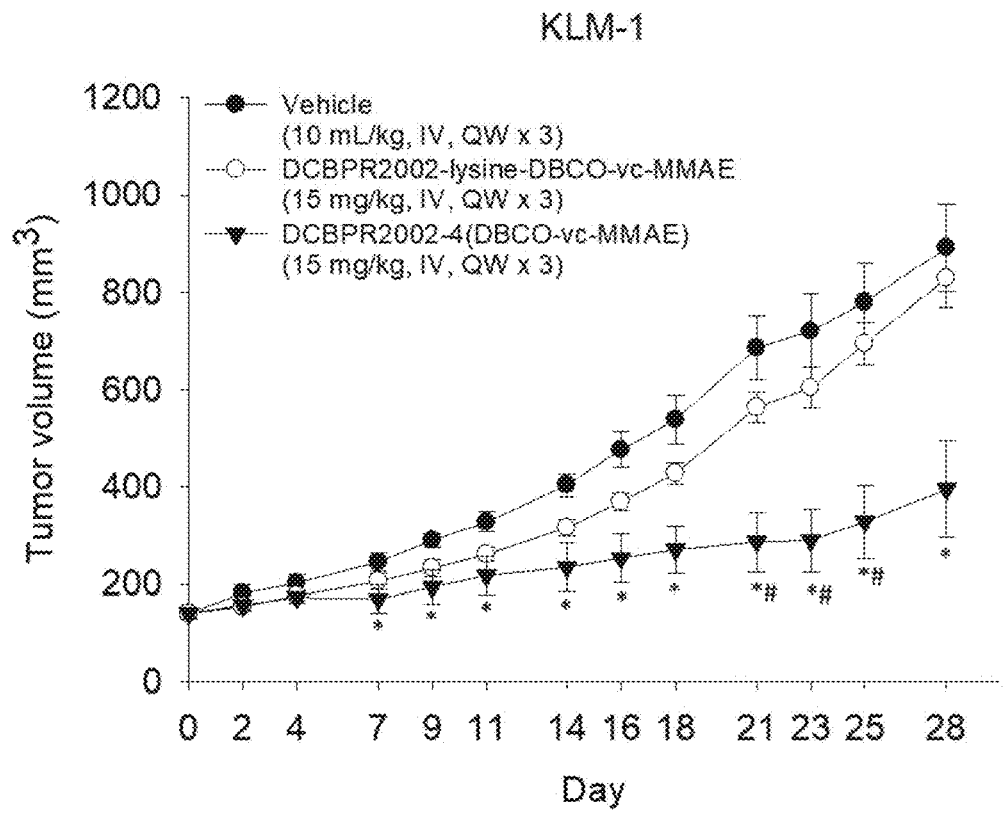
FIG. 9 shows the tumor growth curve in KLM-1 implanted male NOD SCID mice.

FIG. 9 shows the tumor growth curve in KLM-1 implanted male NOD SCID mice. Each of test articles DCBPR2002-lysine-DBCO-vc-MMAE (15 mg/kg) and DCBPR2002-4(DBCO-vc-MMAE) (15 mg/kg) was administered intravenously once weekly for 3 weeks. Tumor growth inhibition (TGI)≥58% was considered significant anti-tumor activity (#) compared to the vehicle group. One-way ANOVA followed by Dunnett's test was applied for comparison between the vehicle and test article-treated groups. Differences are considered significant at *P<0.05. DCBPR2002-4(DBCO-vc-MMAE) at 15 mg/kg significantly reduced KLM-1 tumor growth from Day 7 to Day 28. DCBPR2002-lysine-DBCO-vc-MMAE at 15 mg/kg did not show significant anti-tumor activity.

Figure 10:
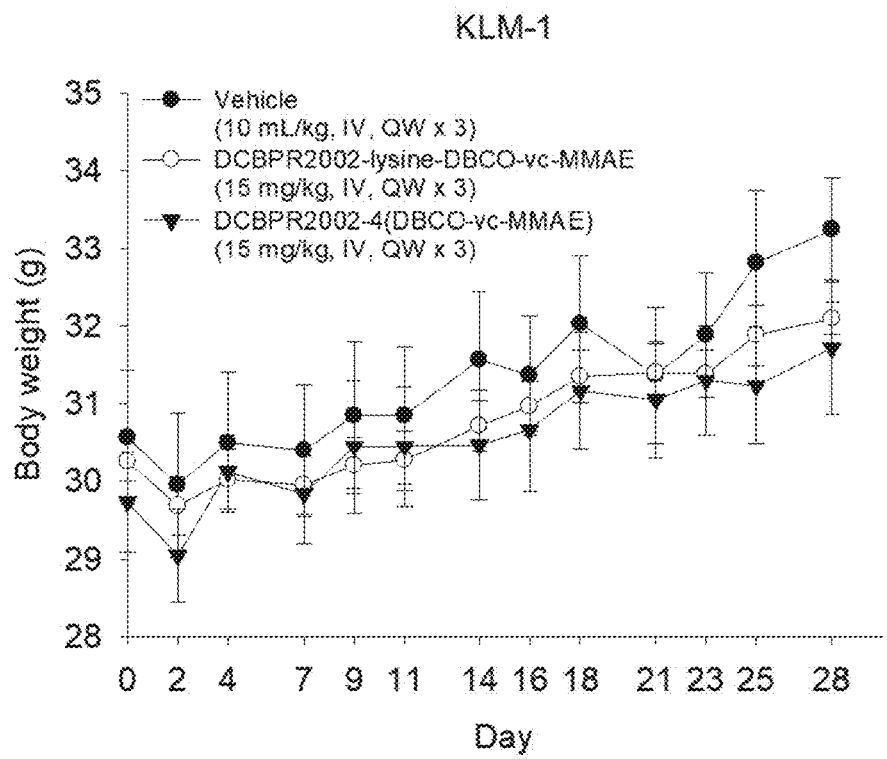
FIG. 10 shows the body weight changes in KLM-1 implanted male NOD SCID mice.

FIG. 10 shows the body weight changes in KLM-1 implanted male NOD SCID mice. Each of test articles DCBPR2002-lysine-DBCO-vc-MMAE (15 mg/kg) and DCBPR2002-4(DBCO-vc-MMAE) (15 mg/kg) was administered intravenously once weekly for 3 weeks. No body weight loss was observed throughout the experiment.

Example 44 Xenograft Model of Anti-MSLN ADC (Pancreatic Cancer)

The aim of this study was to evaluate the in vivo anti-tumor efficacy of DCBPR2002, and DCBPR2002-4(DBCOvc-MMAE) in KLM-1 human pancreatic cancer xenograft model in male NOD SCID mice.

Formulations respectively comprising test article DCBPR2002, test article DCBPR2002-4(DBCO-vc-MMAE), and a corresponding vehicle were formulated by diluting the stock with a 25 mM sodium citrate buffer (pH6.5). Each of the formulations was administered intravenously (IV) to the mice once weekly for three weeks.

The KLM-1 cells were maintained in vitro as a monolayer culture in RPMI-1640 medium supplemented with 10% fetal bovine serum at 37° C. in an atmosphere of 5% $CO_2$ in air. The tumor cells were routinely sub-cultured twice weekly by trypsin-EDTA treatment. The cells growing in an exponential growth phase were harvested and counted for tumor inoculation.

Male NOD SCID mice at age of 6-7 weeks were purchased from BioLasco Taiwan Co., LTD. and quarantined for one week. Five mice were housed in each cage. All animals were hosted in the animal facility with a 12-h light/12-h dark cycle at 19-25° C. Animals had free access to rodent pellet foods and water ad libitum.

KLM-1 cells were subcutaneously (SC) implanted ($4 \times 10^6$ cells in 1:1 PBS/matrigel mixture at 0.1 mL per mouse) into the right flank of male NOD SCID mice. When the average tumor volume had reached 200 mm$^3$, the mice were randomLy divided into 4 groups (N=6 per group). Each of the vehicle, DCBPR2002-4(DBCO-vc-MMAE) (15 and 30 mg/kg), and naked antibody (DCBPR2002, 30 mg/kg) was intravenously administered once weekly for 3 weeks.

The tumor volumes, body weights, mortality, and signs of overt toxicity were monitored and recorded three times weekly for 28 days. Tumor volumes (mm$^3$) were measured three times per week using calipers and calculated according to the formula: Tumor Volume=$(w^2 \times l)/2$, where w=width and l=length in diameter (mm) of the tumor. The percentages of tumor growth inhibition (TGI) were calculated using the following formula: % TGI=$[1-(T/C)] \times 100\%$, where T and C represent the mean tumor volumes of the treatment group and the control group, respectively. A TGI (%) value≥58% was considered significant anti-tumor activity. One-way ANOVA followed by Dunnett's test was applied for comparison between the vehicle and test article-treated groups. Differences are considered significant at *P<0.05. Animals were weighed three times weekly until the completion of the study.

Figure 11:
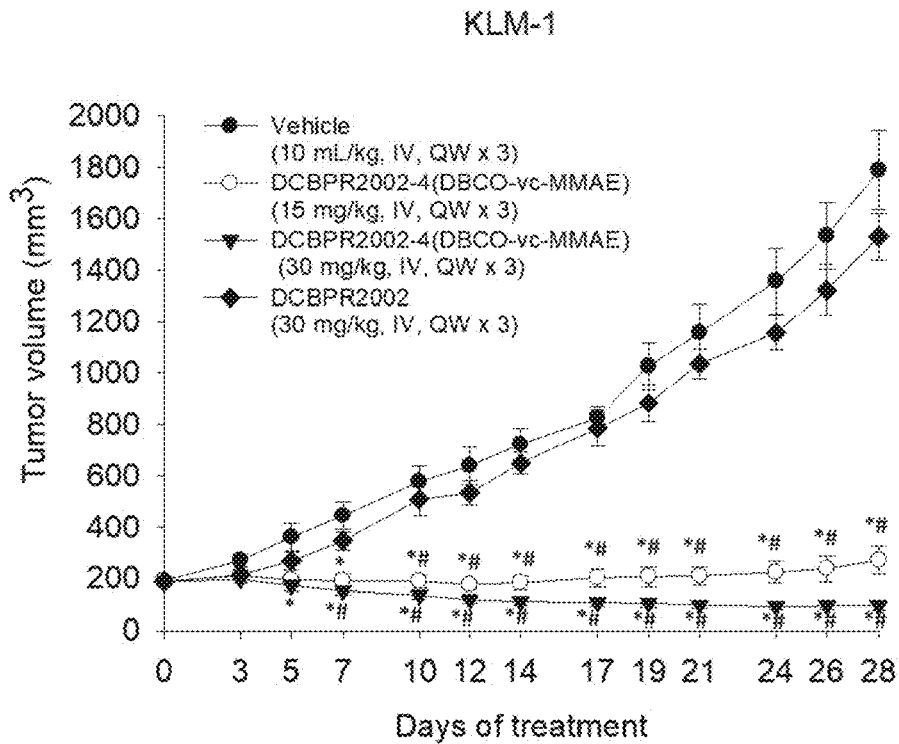
FIG. 11 shows the tumor growth curve in KLM-1 implanted male NOD SCID mice.

FIG. 11 shows the tumor growth curve in KLM-1 implanted male NOD SCID mice. Each of test articles DCBPR2002 (30 mg/kg) and DCBPR2002-4(DBCO-vc-MMAE) (15 and 30 mg/kg) was administered intravenously once weekly for 3 weeks. Tumor growth inhibition (TGI) ≥58% was considered significant anti-tumor activity (#) compared to the vehicle group. One-way ANOVA followed by Dunnett's test was applied for comparison between the vehicle and test article-treated groups. Differences are considered significant at *P<0.05. DCBPR2002-4(DBCO-vc-MMAE) at 15 and 30 mg/kg significantly reduced KLM-1 tumor growth from Day 7 to Day 28. DCBPR2002 at 30 mg/kg did not show significant anti-tumor activity.

Figure 12:
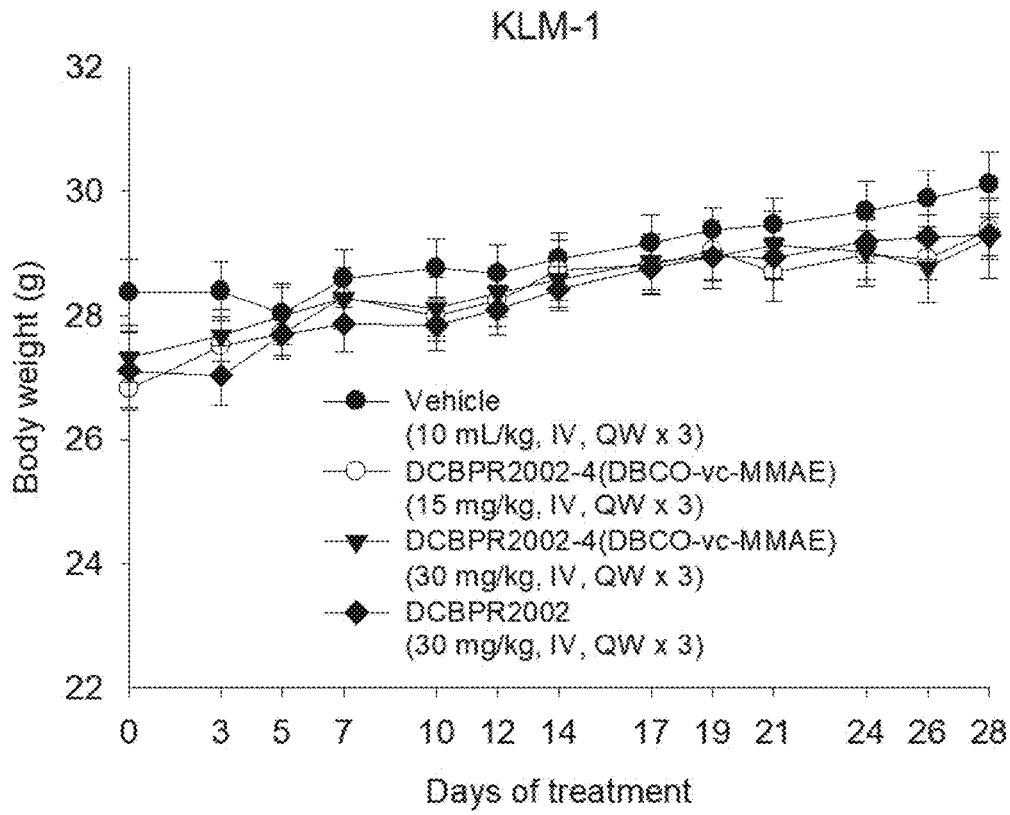
FIG. 12 shows the body weight changes in KLM-1 implanted male NOD SCID mice.

FIG. 12 shows the body weight changes in KLM-1 implanted male NOD SCID mice. Each of test articles DCBPR2002 (30 mg/kg) and DCBPR2002-4(DBCO-vc-MMAE) (15 and 30 mg/kg) was administered intravenously once weekly for 3 weeks. No body weight loss was observed throughout the experiment.

Example 45 Xenograft Model of Anti-MSLN ADC (Pancreatic Cancer)

The aim of this study was to evaluate the in vivo antitumor efficacy of DCBPR2002-4(DBCO-vc-MMAE), DCBPR2002-4(DBCO-vc-seco-DUBA), DCBPR2002-4(DBCO-s-DM1), DCBPR2002-2(DBCO-vc-MMAE)-2(DBCO-vc-seco-DUBA), DCBPR2002-2(DBCO-vc-seco-DUBA)-2(DBCO-s-DM1), and DCBPR2002-2(DBCO-vc-MMAE)-2(DBCO-s-DM1) in KLM-1 human pancreatic cancer xenograft model in male NOD SCID mice.

Formulations respectively comprising test article DCBPR2002-4(DBCO-vc-MMAE)(15 mg/kg), test article DCBPR2002-4(DBCO-vc-seco-DUBA)(15 mg/kg), test article DCBPR2002-4(DBCO-s-DM1) (15 mg/kg), test article DCBPR2002-2(DBCO-vc-MMAE)-2(DBCO-vc-seco-DUBA) (15 mg/kg), test article DCBPR2002-2 (DBCO-vc-MMAE)-2(DBCO-s-DM1) (15 mg/kg), test article DCBPR2002-2(DBCO-vc-seco-DUBA)-2(DBCO-s-DM1) (15 mg/kg), and a corresponding vehicle were formulated by diluting the stock with a 25 mM sodium citrate buffer (pH6.5). Each of the formulations was administered intravenously (IV) once weekly for three weeks.

The KLM-1 cells were maintained in vitro as a monolayer culture in RPMI-1640 medium supplemented with 10% fetal bovine serum at 37° C. in an atmosphere of 5% $CO_2$ in air. The tumor cells were routinely sub-cultured twice weekly by trypsin-EDTA treatment. The cells growing in an exponential growth phase were harvested and counted for tumor inoculation.

Male NOD SCID mice at age of 6-7 weeks were purchased from BioLasco Taiwan Co., LTD. and quarantined for one week. Five mice were housed in each cage. All animals were hosted in the animal facility with a 12-h light/12-h dark cycle at 19-25° C. Animals had free access to rodent pellet foods and water ad libitum.

KLM-1 cells were subcutaneously (SC) implanted ($4 \times 10^6$ cells in 1:1 PBS/matrigel mixture at 0.1 mL per mouse) into the right flank of male NOD SCID mice. When the average tumor volume had reached 300 mm$^3$, the mice were randomly divided into 7 groups (N=6 per group). Each of the vehicle, DCBPR2002-4(DBCO-vc-MMAE), DCBPR2002-4(DBCO-vc-seco-DUBA), DCBPR2002-4(DBCO-s-DM1), DCBPR2002-2(DBCO-vc-MMAE)-2(DBCO-vc-seco-DUBA), DCBPR2002-2(DBCO-vc-MMAE)-2(DBCO-s-DM1), DCBPR2002-2(DBCO-vc-seco-DUBA)-2(DBCO-s-DM1) was intravenously administered as 15 mg/kg once weekly for 3 weeks.

The tumor volumes, body weights, mortality, and signs of overt toxicity were monitored and recorded three times weekly for 28 days. Tumor volumes were measured three times per week using calipers and calculated according to the formula: Tumor Volume=$(w2 \times l)/2$, where w=width and l=length in diameter (mm) of the tumor. The percentages of tumor growth inhibition (TGI) were calculated using the following formula: % TGI=$[1-(T/C)] \times 100\%$, where T and C represent the mean tumor volumes of the treatment group and the control group, respectively. A TGI (%) value≥58% was considered significant anti-tumor activity. One-way ANOVA followed by Dunnett's test was applied for comparison between the vehicle and test article-treated groups. Differences are considered significant at *P<0.05. Animals were weighed three times weekly until the completion of the study.

Figure 13:
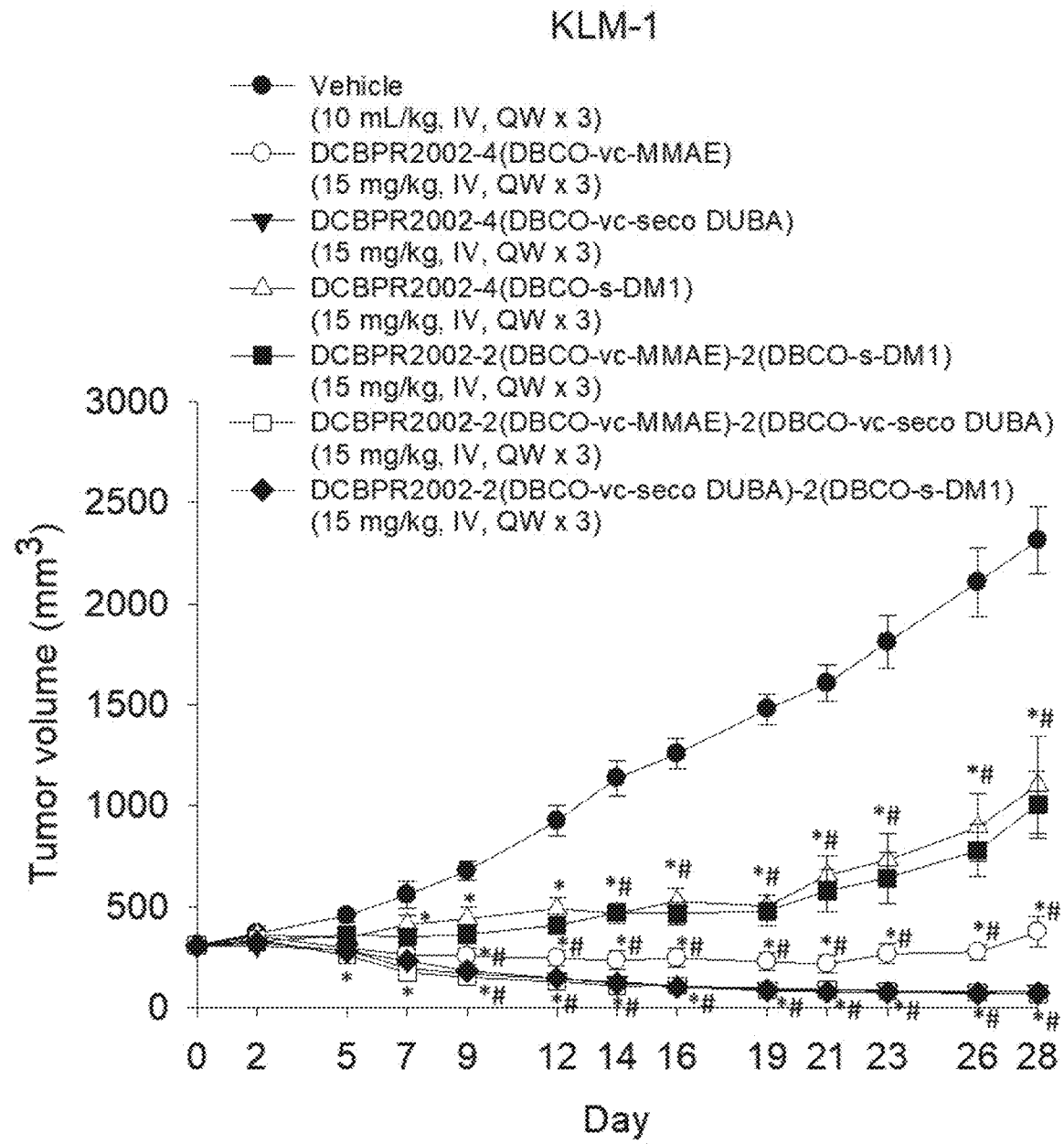
FIG. 13 shows the tumor growth curve in KLM-1 implanted male NOD SCID mice.

FIG. 13 shows the tumor growth curve in KLM-1 implanted male NOD SCID mice. Each of the test articles DCBPR2002-4(DBCO-vc-MMAE), DCBPR2002-4 (DBCO-vc-seco-DUBA), DCBPR2002-4(DBCO-s-DM1), DCBPR2002-2(DBCO-vc-MMAE)-2(DBCO-s-DM1), DCBPR2002-2(DBCO-vc-MMAE)-2(DBCO-vc-seco-DUBA), and DCBPR2002-2(DBCO-vc-seco-DUBA)-2 (DBCO-s-DM1) was intravenously administered as 15 mg/kg once weekly for 3 weeks. Tumor growth inhibition (TGI)≥58% was considered significant anti-tumor activity (#) compared to the vehicle group. One-way ANOVA followed by Dunnett's test was applied for comparison between the vehicle and test article-treated groups. Differences are considered significant at *P<0.05. All of the anti-MSLN ADCs showed significant anti-tumor activity. The ranking of efficacy potency was DCBPR2002-4 (DBCO-vc-seco-DUBA)=DCBPR2002-2(DBCO-vc-MMAE)-2(DBCO-vc-seco-DUBA)=DCBPR2002-2 (DBCO-vc-seco-DUBA)-2(DBCO-s-DM1)>DCBPR2002-4(DBCO-vc-MMAE)>DCBPR2002-2(DBCO-vc-MMAE)-2(DBCO-s-DM1)>DCBPR2002-4(DBCO-s-DM1).

Figure 14:
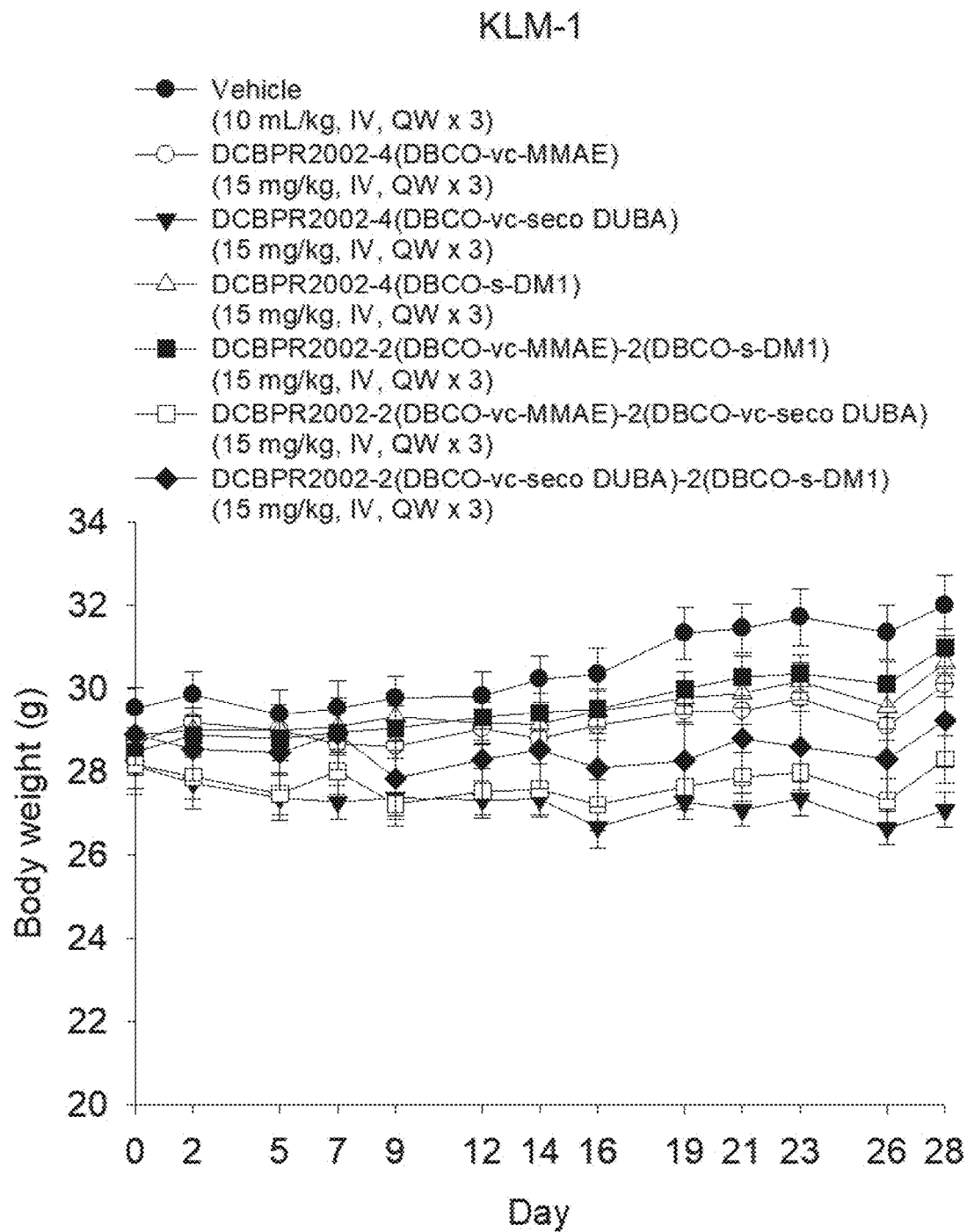
FIG. 14 shows the body weight changes in KLM-1 implanted male NOD SCID mice.

FIG. 14 shows the body weight changes in KLM-1 implanted male NOD SCID mice. Each of the articles DCBPR2002-4(DBCO-vc-MMAE), DCBPR2002-4 (DBCO-vc-seco-DUBA), DCBPR2002-4(DBCO-s-DM1), DCBPR2002-2(DBCO-vc-MMAE)-2(DBCO-s-DM1), DCBPR2002-2(DBCO-vc-MMAE)-2(DBCO-vc-seco-DUBA), and DCBPR2002-2(DBCO-vc-seco-DUBA)-2 (DBCO-s-DM1) was intravenously administered as 15 mg/kg once weekly for 3 weeks. No body weight loss was observed among the treatment groups.

Example 46 Xenograft Model of Anti-MSLN ADC (Ovarian Cancer)

The aim of this study was to evaluate the in vivo anti-tumor efficacy of DCBPR2002-4(DBCO-vc-MMAE) and DCBPR2002-4(DBCO-vc-seco-DUBA) in OVCAR-3 human ovarian cancer xenograft model in female NOD SCID mice.

Formulations respectively comprising test article DCBPR2002-4(DBCO-vc-MMAE), test article DCBPR2002-4(DBCO-vc-seco-DUBA), and a corresponding vehicle were formulated by diluting the stock with a 25 mM sodium citrate buffer (pH6.5). Each of the formulations was administered intravenously (IV) once weekly for three weeks.

The OVCAR-3 cells were maintained in vitro as a monolayer culture in RPMI-1640 medium supplemented with 20% fetal bovine serum at 37° C. in an atmosphere of 5% $CO_2$ in air. The tumor cells were routinely sub-cultured twice weekly by trypsin-EDTA treatment. The cells growing in an exponential growth phase were harvested and counted for tumor inoculation.

Female NOD SCID mice at age of 6-7 weeks were purchased from BioLasco Taiwan Co., LTD. and quarantined for one week. Five mice were housed in each cage. All animals were hosted in the animal facility with a 12-h light/12-h dark cycle at 19-25° C. Animals had free access to rodent pellet foods and water ad libitum.

OVCAR-3 cells were subcutaneously (SC) implanted ($1\times10^7$ cells in 1:1 PBS/matrigel mixture at 0.2 mL per mouse) into the right flank of female NOD SCID mice. When the average tumor volume had reached 300 mm³, the mice were randomLy divided into 4 groups (N=6 per group). Each of the vehicle, DCBPR2002-4(DBCO-vc-MMAE) (15 and 30 mg/kg), and DCBPR2002-4(DBCO-vc-seco-DUBA) (15 mg/kg) was intravenously administered once weekly for 3 weeks.

Tumor volumes were measured three times per week using calipers and estimated using the following formula: Tumor Volume=$(w^2 \times l)/2$, where w=width and l=length in diameter (mm) of the tumor. The percentages of tumor growth inhibition (TGI) were calculated using the following formula: % TGI=[1−(T/C)]×100%, where T and C represent the mean tumor volumes of the treatment group and the control group, respectively. A TGI (%) value≥58% was considered significant anti-tumor activity. One-way ANOVA followed by Dunnett's test was applied for comparison between the vehicle and test article-treated groups. Differences are considered significant at *P<0.05. Animals were weighed three times weekly until the completion of the study.

Figure 15:
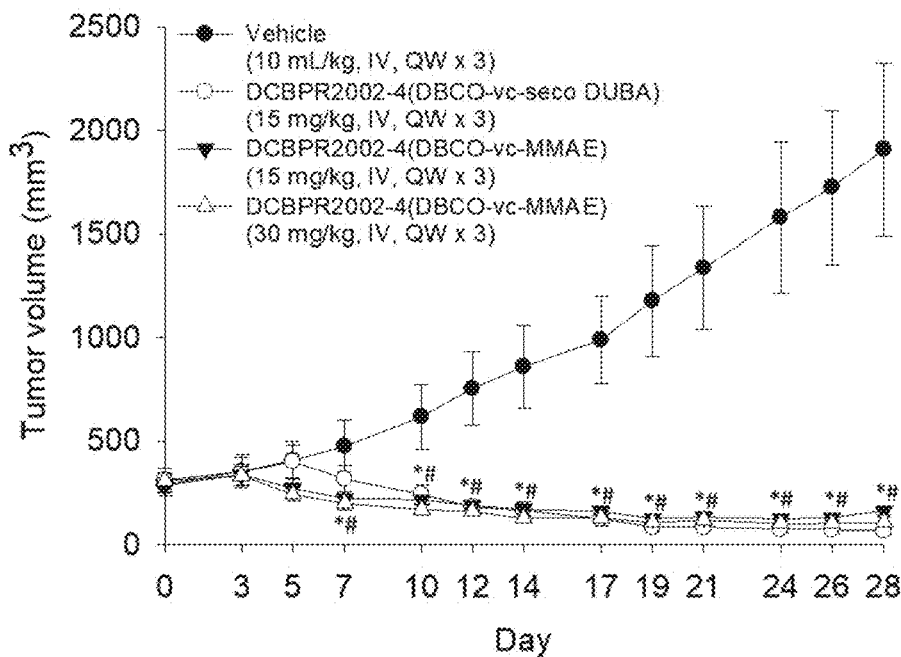
FIG. 15 shows the tumor growth curve in OVCAR-3 implanted female NOD SCID mice.

FIG. 15 shows the tumor growth curve in OVCAR-3 implanted female NOD SCID mice. Each of the test articles DCBPR2002-4(DBCO-vc-MMAE) (15 and 30 mg/kg) and DCBPR2002-4(DBCO-vc-seco-DUBA) (15 mg/kg) was intravenously administered once weekly for 3 weeks. Tumor growth inhibition (TGI)≥58% was considered significant anti-tumor activity (#) compared to the vehicle group. One-way ANOVA followed by Dunnett's test was applied for comparison between the vehicle and test article-treated groups. Differences are considered significant at *P<0.05. DCBPR2002-4(DBCO-vc-MMAE) (15 and 30 mg/kg), and DCBPR2002-4(DBCO-vc-seco-DUBA)(15 mg/kg) significantly reduced OVCAR-3 tumor growth, with a TGI (%) value of >90%, respectively.

Figure 16:
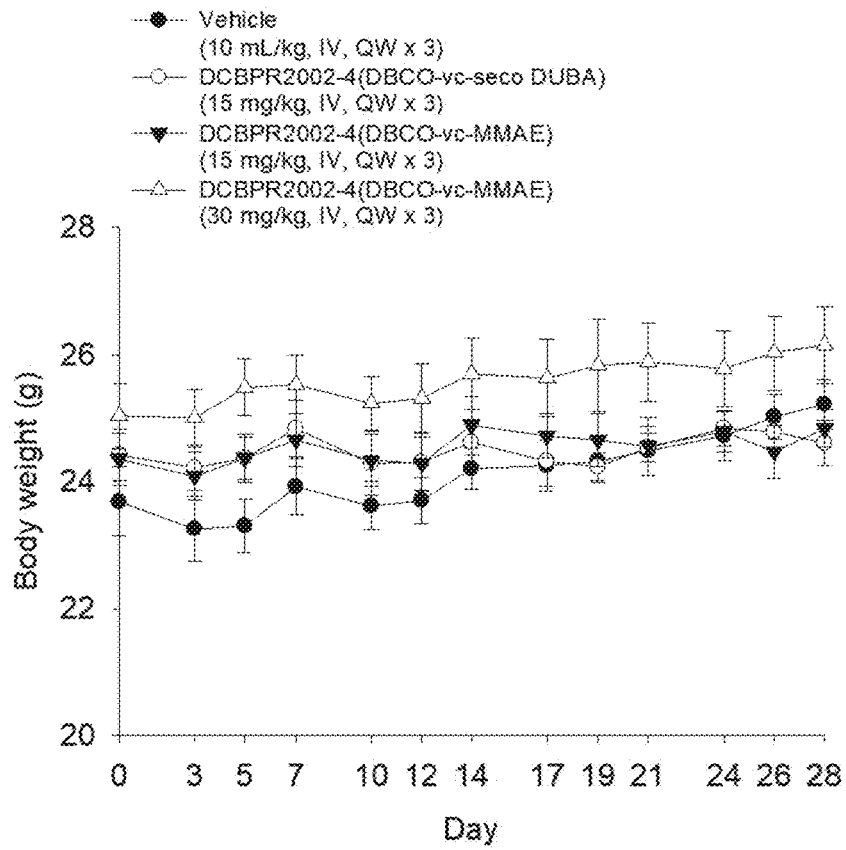
FIG. 16 shows the body weight changes in OVCAR-3 implanted female NOD SCID mice.

FIG. 16 shows the body weight changes in OVCAR-3 implanted female NOD SCID mice. Each of the test articles DCBPR2002-4(DBCO-vc-MMAE) (15 and 30 mg/kg) and DCBPR2002-4(DBCO-vc-seco-DUBA) (15 mg/kg) was intravenously administered once weekly for 3 weeks. No body weight loss was observed among the treatment groups.

Example 47 Xenograft Model of Anti-MSLN ADC (Ovarian Cancer)

The aim of this study was to evaluate the in vivo anti-tumor efficacy of DCBPR2002-4(DBCO-vc-MMAE) and DCBPR2002-TM in OVCAR-3 human ovarian cancer xenograft model in female NOD SCID mice.

Formulations respectively comprising test article DCBPR2002-4(DBCO-vc-MMAE), test article DCBPR2002-TM and a corresponding vehicle were formulated by diluting the stock with a 25 mM sodium citrate buffer (pH6.5). Each of the formulations was administered intravenously (IV) once weekly for three weeks.

The OVCAR-3 cells were maintained in vitro as a monolayer culture in RPMI-1640 medium supplemented with 20% fetal bovine serum at 37° C. in an atmosphere of 5% $CO_2$ in air. The tumor cells were routinely sub-cultured twice weekly by trypsin-EDTA treatment. The cells growing in an exponential growth phase were harvested and counted for tumor inoculation.

Female NOD SCID mice at age of 6-7 weeks were purchased from BioLasco Taiwan Co., LTD. and quarantined for one week. Five mice were housed in each cage. All animals were hosted in the animal facility with a 12-h light/12-h dark cycle at 19-25° C. Animals had free access to rodent pellet foods and water ad libitum.

OVCAR-3 cells were subcutaneously (SC) implanted ($1\times10^7$ cells in 1:1 PBS/matrigel mixture at 0.2 mL per mouse) into the right flank of female NOD SCID mice. When the average tumor volume had reached 300 mm³, the mice were randomly divided into 4 groups (N=5 per group). Each of the vehicle, DCBPR2002-4(DBCO-vc-MMAE) (5 and 15 mg/kg), and DCBPR2002-TM (15 mg/kg) was intravenously administered once weekly for 3 weeks.

Tumor volumes were measured three times per week using calipers and estimated using the following formula: Tumor Volume=$(w^2 \times l)/2$, where w=width and l=length in diameter (mm) of the tumor. The percentages of tumor growth inhibition (TGI) were calculated using the following formula: % TGI=[1−(T/C)]×100%, where T and C represent the mean tumor volumes of the treatment group and the control group, respectively. A TGI (%) value≥58% was considered significant anti-tumor activity. One-way ANOVA followed by Dunnett's test was applied for comparison between the vehicle and test article-treated groups. Differences are considered significant at *P<0.05. Animals were weighed three times weekly until the completion of the study.

Figure 17:
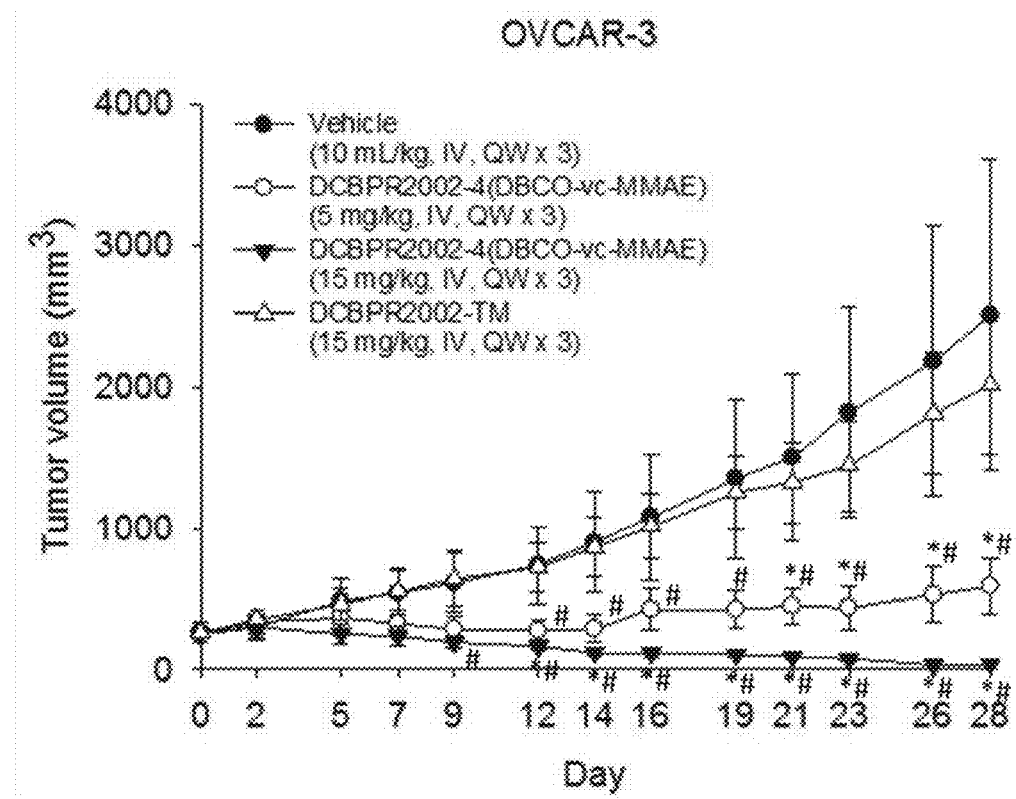
FIG. 17 shows the tumor growth curve in OVCAR-3 implanted female NOD SCID mice.

FIG. 17 shows the tumor growth curve in OVCAR-3 implanted female NOD SCID mice. Each of the test articles DCBPR2002-4(DBCO-vc-MMAE) (5 and 15 mg/kg) and DCBPR2002-TM (15 mg/kg) was intravenously administered once weekly for 3 weeks. Tumor growth inhibition (TGI)≥58% was considered significant anti-tumor activity (#) compared to the vehicle group. One-way ANOVA followed by Dunnett's test was applied for comparison between the vehicle and test article-treated groups. Differences are considered significant at *P<0.05. DCBPR2002-4(DBCO-vc-MMAE) (5 and 15 mg/kg) significantly reduced OVCAR-3 tumor growth. DCBPR2002-TM at 15 mg/kg did not show anti-tumor activity.

Figure 18:
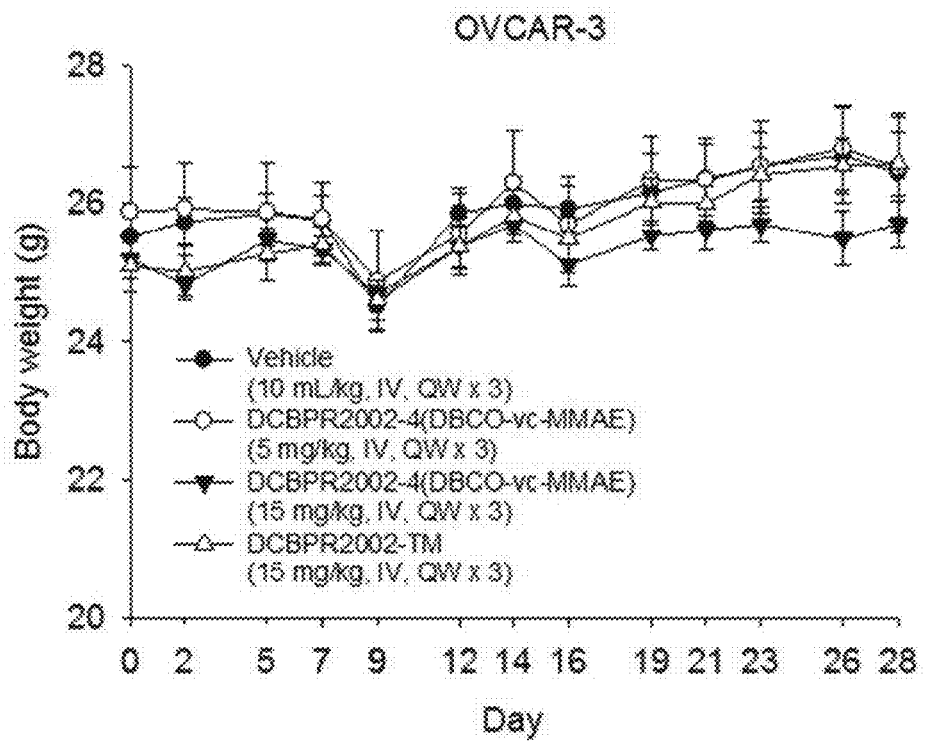
FIG. 18 shows the body weight changes in OVCAR-3 implanted female NOD SCID mice.

FIG. 18 shows the body weight changes in OVCAR-3 implanted female NOD SCID mice. Each of the test articles DCBPR2002-4(DBCO-vc-MMAE) (5 and 15 mg/kg) and DCBPR2002-TM (15 mg/kg) was intravenously administered once weekly for 3 weeks. No body weight loss was observed among the treatment groups.

Example 48 Xenograft Model of Anti-MSLN ADC (Ovarian Cancer)

The aim of this study was to evaluate the in vivo anti-tumor efficacy of DCBPR2002-4(DBCO-vc-MMAE) in OVCAR-3 human ovarian cancer xenograft model in female NOD SCID mice.

Formulations respectively comprising test article DCBPR2002-4(DBCO-vc-MMAE), and a corresponding vehicle were formulated by diluting the stock with a 25 mM sodium citrate buffer (pH6.5). Each of the formulations was administered intravenously (IV) once weekly for three weeks.

The OVCAR-3 cells were maintained in vitro as a monolayer culture in RPMI-1640 medium supplemented with 20% fetal bovine serum at 37° C. in an atmosphere of 5% $CO_2$ in air. The tumor cells were routinely sub-cultured twice weekly by trypsin-EDTA treatment. The cells growing in an exponential growth phase were harvested and counted for tumor inoculation.

Female NOD SCID mice at age of 6-7 weeks were purchased from BioLasco Taiwan Co., LTD. and quarantined for one week. Five mice were housed in each cage. All animals were hosted in the animal facility with a 12-h light/12-h dark cycle at 19-25° C. Animals had free access to rodent pellet foods and water ad libitum.

OVCAR-3 cells were subcutaneously (SC) implanted ($1×10^7$ cells in 1:1 PBS/matrigel mixture at 0.2 mL per mouse) into the right flank of female NOD SCID mice. When the average tumor volume had reached 300 mm$^3$, the mice were randomly divided into 4 groups (N=5 per group). Each of the vehicle, and DCBPR2002-4(DBCO-vc-MMAE) (5, 10, and 15 mg/kg) was intravenously administered once weekly for 3 weeks.

Tumor volumes were measured three times per week using calipers and estimated using the following formula: Tumor Volume=$(w^2×l)/2$, where w=width and l=length in diameter (mm) of the tumor. The percentages of tumor growth inhibition (TGI) were calculated using the following formula: % TGI=[1−(T/C)]×100%, where T and C represent the mean tumor volumes of the treatment group and the control group, respectively. A TGI (%) value≥58% was considered significant anti-tumor activity. One-way ANOVA followed by Dunnett's test was applied for comparison between the vehicle and test article-treated groups. Differences are considered significant at *P<0.05. Animals were weighed three times weekly until the completion of the study.

Figure 19:
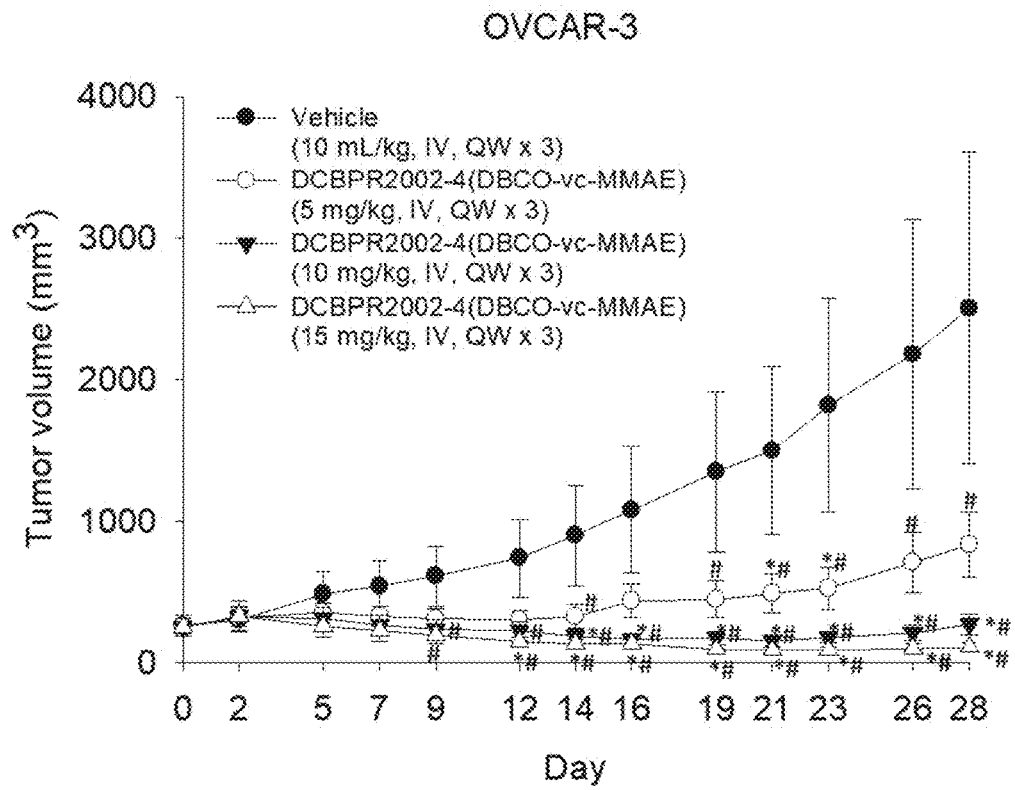
FIG. 19 shows the tumor growth curve in OVCAR-3 implanted female NOD SCID mice.

FIG. 19 shows the tumor growth curve in OVCAR-3 implanted female NOD SCID mice. Each of the test articles DCBPR2002-4(DBCO-vc-MMAE) (5, 10, and 15 mg/kg) was intravenously administered once weekly for 3 weeks. Tumor growth inhibition (TGI)≥58% was considered significant anti-tumor activity (#) compared to the vehicle group. One-way ANOVA followed by Dunnett's test was applied for comparison between the vehicle and test article-treated groups. Differences are considered significant at *P<0.05. DCBPR2002-4(DBCO-vc-MMAE) (5, 10, and 15 mg/kg) significantly reduced OVCAR-3 tumor growth with a dose-dependent manner.

Figure 20:
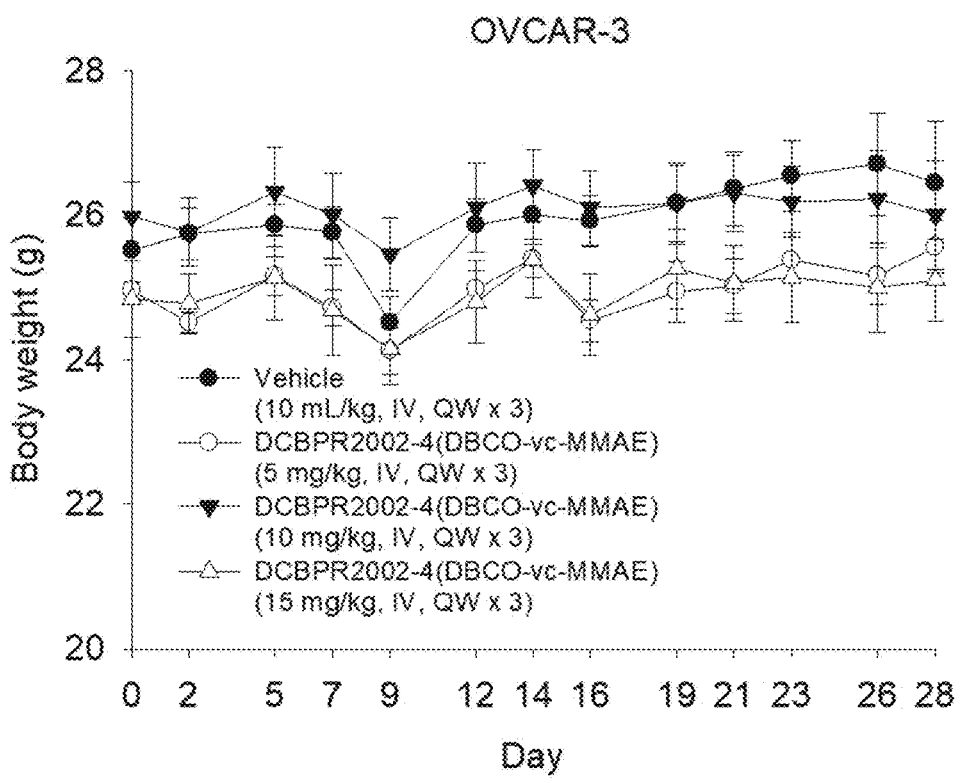
FIG. 20 shows the body weight changes in OVCAR-3 implanted female NOD SCID mice.

FIG. 20 shows the body weight changes in OVCAR-3 implanted female NOD SCID mice. Each of the test articles DCBPR2002-4(DBCO-vc-MMAE) (5, 10, and 15 mg/kg) was intravenously administered once weekly for 3 weeks. No body weight loss was observed among the treatment groups.

The above examples clearly illustrate various methods for obtaining and characterizing ADCs of the invention, as well as the effectiveness of the ADCs of the invention in treating cancers. Even though embodiments of the invention are illustrated with a limited number of examples, one skilled in the art would appreciate that other variations and modifications are possible without departing from the scope of the invention. Accordingly, the scope of protection of the invention should only be limited by the attached claims.

What is claimed is:

1. An immunoconjugate, comprising:

an antibody comprising an antigen-binding fragment that specifically binds to an epitope in mesothelin, an N-glycan binding domain and an N-glycan having a structure of formula (1);

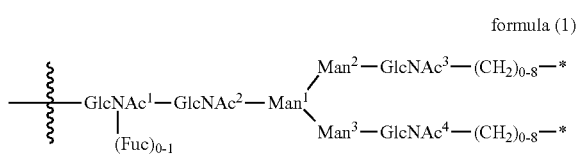

formula (1)

wherein "*" represents a bond or a protecting group;

a linker linking to each of the "*" in the N-glycan when "*" presents the bond; and a payload A and a payload B independently conjugated to the linkers; wherein the payload A and the payload B are the same or different;

wherein the antibody comprises a heavy chain variable region comprising the amino acid sequence of SEQ ID NO: 11, and a light chain variable region comprising the amino acid sequence of SEQ ID NO: 12.

2. The immunoconjugate according to claim 1, wherein the antibody is a monoclonal antibody, a humanized antibody, an antibody Fab fragment, F(ab')$_2$, Fv fragment or Fc fragment from a cleaved antibody, a scFv-Fc fragment, a minibody, a diabody, or a scFv.

3. The immunoconjugate according to claim 1, wherein the antibody comprises a heavy chain constant region, and the N-glycan binding domain is located in the heavy chain constant region.

4. The immunoconjugate according to claim 1, wherein the antibody comprises two N-glycans.

5. The immunoconjugate according to claim 1, wherein the linker is selected from the group consisting of a linear or branched alkyl, cycloalkyl, alkenyl, cycloalkenyl, alkynyl, aryl, heteroaryl, alkoxy, acyl, alkylamine, arylamine group having 2 to 20 carbon atoms, ether, ester, amide, carbamate, formula (3) to formula (7), disulfide containing linker, acid labile linker, photolabile linker, peptidase labile linker, and esterase labile linker, or combinations thereof;

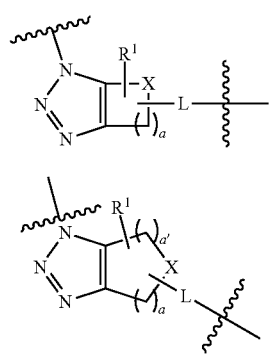

formula (3)

formula (4)

wherein in formula (3) and formula (4):

$R^1$ is independently selected from the group consisting of hydrogen, halogen, $-OR^5$, $-NO_2$, $-CN$, $-S(O)_2R^5$, a $C_1$-$C_{24}$ alkyl group, a $C_6$-$C_{24}$ (hetero)aryl group, a $C_7$-$C_{24}$ alkyl(hetero)aryl group and a $C_7$-$C_{24}$ (hetero)arylalkyl group, and wherein the alkyl group, (hetero)aryl group, alkyl(hetero)aryl group and (hetero)arylalkyl group are optionally substituted, two substituents $R^1$ may be linked together to form an annelated cycloalkyl or an annelated (hetero)arene substituent, and $R^5$ is independently selected from the group consisting of hydrogen, halogen, a $C_1$-$C_{24}$ alkyl group, a $C_6$-$C_{24}$ (hetero)aryl group, a $C_7$-$C_{24}$ alkyl(hetero)aryl group, and a $C_7$-$C_{24}$ (hetero)arylalkyl group;

X is $C(R^1)_2$, O, S or $NR^2$, wherein $R^2$ is $R^1$; a is 0, 1, 2, 3, 4, 5, 6, 7 or 8; a' is 0, 1, 2, 3, 4, 5, 6, 7 or 8; and a+a'<10; and L is selected from the group consisting of a linear or branched alkyl, cycloalkyl, alkenyl, cycloalkenyl, alkynyl, aryl, heteroaryl, alkoxy, acyl, alkylamine, arylamine group having 2 to 20 carbon atoms, ether, ester, amide, carbamate, carbonate, disulfide containing linker, acid labile linker, photolabile linker, peptidase labile linker, and esterase labile linker, or combinations thereof;

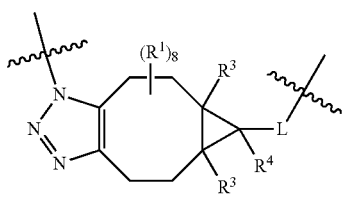

formula (5)

wherein in formula (5), $R^1$ is independently selected from the group consisting of hydrogen, halogen, $-OR^5$, $-NO_2$, $-CN$, $-S(O)_2R^5$, a $C_1$-$C_{24}$ alkyl group, a $C_6$-$C_{24}$ (hetero)aryl group, a $C_7$-$C_{24}$ alkyl(hetero)aryl group and a $C_7$-$C_{24}$ (hetero)arylalkyl group, and wherein the alkyl group, (hetero)aryl group, alkyl(hetero)aryl group and (hetero)arylalkyl group are optionally substituted, two substituents $R^1$ may be linked together to form an annelated cycloalkyl or an annelated (hetero)arene substituent, and $R^5$ is independently selected from the group consisting of hydrogen, halogen, a $C_1$-$C_{24}$ alkyl group, a $C_6$-$C_{24}$ (hetero)aryl groups, $C_7$-$C_{24}$ alkyl(hetero)aryl groups and $C_7$-$C_{24}$ (hetero)arylalkyl groups;

L is selected from the group consisting of a linear or branched alkyl, cycloalkyl, alkenyl, cycloalkenyl, alkynyl, aryl, heteroaryl, alkoxy, acyl, alkylamine, arylamine group having 2 to 20 carbon atoms, ether, ester, amide, carbamate, carbonate, disulfide containing linker, acid labile linker, photolabile linker, peptidase labile linker, and esterase labile linker, or combinations thereof;

$R^3$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups; and $R^4$ is selected from the group consisting of hydrogen, halogen, a $C_1$-$C_{24}$ alkyl group, a $C_6$-$C_{24}$ (hetero)aryl group, a $C_7$-$C_{24}$ alkyl(hetero)aryl group, a $C_7$-$C_{24}$ (hetero)arylalkyl group, the alkyl group optionally being interrupted by one of more hetero-atoms selected from the group consisting of O, N and S, wherein the alkyl group, (hetero)aryl group, alkyl(hetero)aryl group and (hetero)arylalkyl group are independently optionally substituted; and

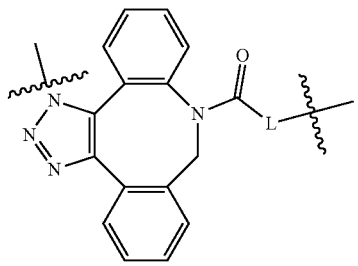

formula (6)

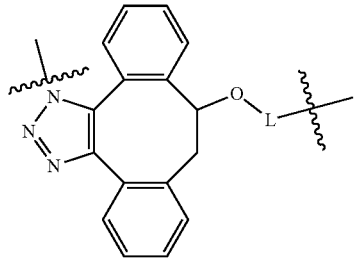

formula (7)

wherein in formula (6) and formula (7),

L is selected from the group consisting of a linear or branched alkyl, cycloalkyl, alkenyl, cycloalkenyl, alkynyl, aryl, heteroaryl, alkoxy, acyl, alkylamine, arylamine group having 2 to 20 carbon atoms, ether, ester, amide, carbamate, carbonate, disulfide containing linker, acid labile linker, photolabile linker, peptidase labile linker, and esterase labile linker, or combinations thereof.

6. The immunoconjugate according to claim 1, wherein the payload A and the payload B are independently a therapeutic agent, or a label.

7. The immunoconjugate according to claim 6, wherein the therapeutic agent is antimetabolites, alkylating agents, alkylating-like agents, DNA minor groove alkylating agents, anthracyclines, antibiotics, calicheamicins, antimitotic agents, topoisomerase inhibitors, proteasome inhibitors, radioisotopes, or isotope-chelating agents.

8. The immunoconjugate according to claim 6, wherein the therapeutic agent is monomethyl auristatin E (MMAE), monomethyl auristatin F (MMAF), maytansinoids, duocarmycin-hydroxy benzamide azaindole (DUBA), diethylenetriamine-N,N,N',N'',N'''-pentaacetate (DTPA), exatecan, or Dxd2.

9. The immunoconjugate according to claim 6, wherein the label is a fluorescent label, a chromophoric label, an electron-dense label, a chemiluminescent label, a radioactive label, an enzymatic label, or a positron emitter.

10. The immunoconjugate according to claim 1, wherein the protecting group is azide.

11. A pharmaceutical composition comprising the immunoconjugate according to claim 1 and a pharmaceutically acceptable carrier.

12. A method for treating cancer in a subject in need thereof comprising administering to the subject a therapeutically effective amount of the immunoconjugate according to claim 1.

13. The method according to claim 12, wherein the cancer is a mesothelin-expressing cancer.

14. The method according to claim 12, wherein the cancer is ovarian cancer, mesothelioma, pancreatic cancer, non-small-cell lung cancer, esophageal cancer, gastric cancer, biliary cancer, colorectal cancer, endometrial cancer, or breast cancer.

15. The method according to claim 12, wherein the cancer is ovarian cancer.

* * * * *

SEQUENCE LISTING

```
<160> NUMBER OF SEQ ID NOS: 16

<210> SEQ ID NO 1
<211> LENGTH: 10
<212> TYPE: PRT
<213> ORGANISM: mouse

<400> SEQUENCE: 1

Gly Tyr Ser Phe Thr Gly Tyr Thr Met Asn
1               5                   10
```

```
<210> SEQ ID NO 2
<211> LENGTH: 17
<212> TYPE: PRT
<213> ORGANISM: mouse

<400> SEQUENCE: 2

Leu Ile Thr Pro Tyr Asn Gly Ala Ser Ser Tyr Asn Gln Lys Phe Arg
1               5                   10                  15
Gly

<210> SEQ ID NO 3
<211> LENGTH: 10
<212> TYPE: PRT
<213> ORGANISM: mouse

<400> SEQUENCE: 3

Gly Gly Tyr Asp Gly Arg Gly Phe Asp Tyr
1               5                   10

<210> SEQ ID NO 4
<211> LENGTH: 10
<212> TYPE: PRT
<213> ORGANISM: mouse

<400> SEQUENCE: 4

Ser Ala Ser Ser Ser Val Ser Tyr Met His
1               5                   10

<210> SEQ ID NO 5
<211> LENGTH: 7
<212> TYPE: PRT
<213> ORGANISM: mouse

<400> SEQUENCE: 5

Asp Thr Ser Lys Leu Ala Ser
1               5

<210> SEQ ID NO 6
<211> LENGTH: 9
<212> TYPE: PRT
<213> ORGANISM: mouse

<400> SEQUENCE: 6

Gln Gln Trp Ser Lys His Pro Leu Thr
1               5

<210> SEQ ID NO 7
<211> LENGTH: 119
<212> TYPE: PRT
<213> ORGANISM: mouse

<400> SEQUENCE: 7

Gln Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
                20                  25                  30

Thr Met Asn Trp Val Lys Gln Ser His Gly Lys Ser Leu Glu Trp Ile
            35                  40                  45

Gly Leu Ile Thr Pro Tyr Asn Gly Ala Ser Ser Tyr Asn Gln Lys Phe
        50                  55                  60

Arg Gly Lys Ala Thr Leu Thr Val Asp Lys Ser Ser Ser Thr Ala Tyr
```

```
             65                  70                  75                  80
Met Asp Leu Leu Ser Leu Thr Ser Glu Asp Ser Ala Val Tyr Phe Cys
                    85                  90                  95

Ala Arg Gly Gly Tyr Asp Gly Arg Gly Phe Asp Tyr Trp Gly Gln Gly
                100                 105                 110

Thr Thr Val Thr Val Ser Ser
            115

<210> SEQ ID NO 8
<211> LENGTH: 107
<212> TYPE: PRT
<213> ORGANISM: mouse

<400> SEQUENCE: 8

Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Gly Arg Phe Ser Gly Ser
    50                  55                  60

Gly Ser Gly Asn Ser Tyr Ser Leu Thr Ile Ser Ser Val Glu Ala Glu
65                  70                  75                  80

Asp Asp Ala Thr Tyr Tyr Cys Gln Gln Trp Ser Lys His Pro Leu Thr
                85                  90                  95

Phe Gly Ala Gly Thr Lys Leu Glu Ile Lys Arg
                100                 105

<210> SEQ ID NO 9
<211> LENGTH: 119
<212> TYPE: PRT
<213> ORGANISM: Artificial Sequence
<220> FEATURE:
<223> OTHER INFORMATION: Artificial antibody

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Gly Leu Glu Trp Val
        35                  40                  45

Ala Leu Ile Thr Pro Tyr Asn Gly Ala Ser Ser Tyr Asn Gln Lys Phe
    50                  55                  60

Arg Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Asp Gly Arg Gly Phe Asp Tyr Trp Gly Gln Gly
                100                 105                 110

Thr Leu Val Thr Val Ser Ser
            115

<210> SEQ ID NO 10
<211> LENGTH: 107
<212> TYPE: PRT
<213> ORGANISM: Artificial Sequence
```

<220> FEATURE:
<223> OTHER INFORMATION: Artificial antibody

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Lys His Pro Leu Thr
                85                  90                  95

Phe Gly Gln Gly Thr Lys Val Glu Ile Lys Arg
            100                 105

<210> SEQ ID NO 11
<211> LENGTH: 119
<212> TYPE: PRT
<213> ORGANISM: Artificial Sequence
<220> FEATURE:
<223> OTHER INFORMATION: Artificial antibody

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Thr Met Asn Trp Val Arg Gln Ala Pro Gly Gln Gly Leu Glu Trp Met
        35                  40                  45

Gly Leu Ile Thr Pro Tyr Asn Gly Ala Ser Ser Tyr Asn Gln Lys Phe
    50                  55                  60

Arg Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Tyr Asp Gly Arg Gly Phe Asp Tyr Trp Gly Gln Gly
            100                 105                 110

Thr Leu Val Thr Val Ser Ser
        115

<210> SEQ ID NO 12
<211> LENGTH: 107
<212> TYPE: PRT
<213> ORGANISM: Artificial Sequence
<220> FEATURE:
<223> OTHER INFORMATION: Artificial antibody

<400> SEQUENCE: 12

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30

His Trp Tyr Gln Gln Lys Pro Gly Gln Ala Pro Arg Leu Leu Ile Tyr
        35                  40                  45

```
Asp Thr Ser Lys Leu Ala Ser Gly Ile Pro Ala Arg Phe Ser Gly Ser
         50                  55                  60
Gly Ser Gly Thr Asp Phe Thr Leu Thr Ile Ser Ser Leu Glu Pro Glu
 65                  70                  75                  80
Asp Phe Ala Val Tyr Tyr Cys Gln Gln Trp Ser Lys His Pro Leu Thr
                 85                  90                  95
Phe Gly Gln Gly Thr Lys Val Glu Ile Lys Arg
                100                 105
```

<210> SEQ ID NO 13
<211> LENGTH: 108
<212> TYPE: PRT
<213> ORGANISM: Homo sapiens

<400> SEQUENCE: 13

```
Asp Ile Gln Met Thr Gln Ser Pro Ser Ser Leu Ser Ala Ser Val Gly
  1               5                  10                  15
Asp Arg Val Thr Ile Thr Cys Arg Ala Ser Gln Asp Val Asn Thr Ala
                 20                  25                  30
Val Ala Trp Tyr Gln Gln Lys Pro Gly Lys Ala Pro Lys Leu Leu Ile
             35                  40                  45
Tyr Ser Ala Ser Phe Leu Glu Ser Gly Val Pro Ser Arg Phe Ser Gly
         50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln His Tyr Thr Thr Pro Pro
                 85                  90                  95
Thr Phe Gly Gln Gly Thr Lys Val Glu Ile Lys Arg
                100                 105
```

<210> SEQ ID NO 14
<211> LENGTH: 120
<212> TYPE: PRT
<213> ORGANISM: Homo sapiens

<400> SEQUENCE: 14

```
Glu Val Gln Leu Val Glu Ser Gly Gly Gly Leu Val Gln Pro Gly Gly
  1               5                  10                  15
Ser Leu Arg Leu Ser Cys Ala Ala Ser Gly Phe Thr Phe Ser Asp Thr
                 20                  25                  30
Tyr Ile His Trp Val Arg Gln Ala Pro Gly Lys Gly Leu Glu Trp Val
             35                  40                  45
Ala Arg Ile Tyr Pro Thr Asn Gly Tyr Thr Arg Tyr Ala Asp Ser Val
         50                  55                  60
Lys Gly Arg Phe Thr Ile Ser Arg Asp Asp Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Trp Gly Gly Asp Gly Phe Tyr Ala Met Asp Val Trp Gly Gln
                100                 105                 110
Gly Thr Leu Val Thr Val Ser Ser
            115                 120
```

<210> SEQ ID NO 15
<211> LENGTH: 106
<212> TYPE: PRT
<213> ORGANISM: Homo sapiens

```
<400> SEQUENCE: 15

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Phe
                85                  90                  95

Gly Gln Gly Thr Lys Val Glu Ile Lys Arg
                100                 105

<210> SEQ ID NO 16
<211> LENGTH: 120
<212> TYPE: PRT
<213> ORGANISM: Homo sapiens

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Gly Gly Asp Gly Phe Tyr Ala Met Asp Val Trp Gly Gln
                100                 105                 110

Gly Thr Leu Val Thr Val Ser Ser
            115                 120
```